US00RE39464E

(19) United States
(12) Reissued Patent
Cook et al.

(10) Patent Number: US RE39,464 E
(45) Date of Reissued Patent: Jan. 9, 2007

(54) OLIGONUCLEOLOTIDES HAVING SITE SPECIFIC CHIRAL PHOSPHOROTHIOATE INTERNUCLEOSIDE LINKAGES

(75) Inventors: Phillip Dan Cook, Fallbrook, CA (US); Muthiah Manoharan, Weston, MA (US)

(73) Assignee: ISIS Pharmaceuticals Inc., Carlsbad, CA (US)

(21) Appl. No.: 10/925,348

(22) Filed: Aug. 24, 2004

Related U.S. Patent Documents

Reissue of:

(64) Patent No.: 6,440,943
Issued: Aug. 27, 2002
Appl. No.: 09/352,058
Filed: Jul. 14, 1999

U.S. Applications:

(63) Continuation-in-part of application No. 09/115,027, filed on Jul. 14, 1998, now Pat. No. 6,242,589.

(51) Int. Cl.
*A61K 31/70* (2006.01)
*G01N 33/53* (2006.01)

(52) U.S. Cl. ..... 514/43; 536/22.1; 536/23.1; 536/24.3; 536/24.31; 536/24.32; 536/24.33; 435/7.2

(58) Field of Classification Search ..... 514/43; 536/22.1, 23.1, 24.3, 24.31, 24.32, 24.33; 435/7.2
See application file for complete search history.

(56) References Cited

U.S. PATENT DOCUMENTS 3,687,808 A * 8/1972 Merigan et al. ..... 435/91.3
4,415,732 A * 11/1983 Caruthers et al. ..... 536/26.5
4,458,066 A * 7/1984 Caruthers et al. ..... 536/25.34
4,469,863 A * 9/1984 Ts'o et al. ..... 536/24.5
4,476,301 A * 10/1984 Imbach et al. ..... 536/25.2
4,500,707 A * 2/1985 Caruthers et al. ..... 536/25.34
4,668,777 A * 5/1987 Caruthers et al. ..... 536/26.5
4,689,320 A * 8/1987 Kaji ..... 514/44
4,725,677 A * 2/1988 Koster et al. ..... 536/25.34
4,806,463 A * 2/1989 Goodchild et al. ..... 435/5
4,816,571 A * 3/1989 Andrus et al. ..... 536/25.3
4,973,679 A * 11/1990 Caruthers et al. ..... 536/26.71
5,004,810 A * 4/1991 Draper ..... 536/24.5
5,023,243 A * 6/1991 Tullis ..... 514/44
5,034,506 A * 7/1991 Summerton et al. ..... 528/391
5,132,418 A * 7/1992 Caruthers et al. ..... 536/25.3
RE34,069 E * 9/1992 Koster et al. ..... 536/25.34
5,166,195 A * 11/1992 Ecker ..... 514/44
5,166,315 A * 11/1992 Summerton et al. ..... 528/406
5,177,196 A * 1/1993 Meyer et al. ..... 536/22.1
5,185,444 A * 2/1993 Summerton et al. ..... 544/81
5,188,897 A * 2/1993 Suhadolnik et al. ..... 428/402.2
5,194,428 A * 3/1993 Agrawal et al. ..... 514/44
5,212,295 A * 5/1993 Cook ..... 536/26.7
5,214,134 A * 5/1993 Weis et al. ..... 536/25.3
5,216,141 A * 6/1993 Benner ..... 536/27.13
5,235,033 A * 8/1993 Summerton et al. ..... 528/391
5,242,906 A * 9/1993 Pagano et al. ..... 514/44
5,248,670 A * 9/1993 Draper et al. ..... 514/44
5,264,423 A * 11/1993 Cohen et al. ..... 514/44
5,264,562 A * 11/1993 Matteucci ..... 536/23.1
5,264,564 A * 11/1993 Matteucci ..... 536/23.1
5,276,019 A * 1/1994 Cohen et al. ..... 514/44
5,278,302 A * 1/1994 Caruthers et al. ..... 536/24.5
5,286,717 A * 2/1994 Cohen et al. ..... 514/44
5,321,131 A * 6/1994 Agrawal et al. 536/25.34jf124c

FOREIGN PATENT DOCUMENTS

WO WO 94/08003 * 4/1994
WO WO 96/37504 * 11/1996
WO WO 96/39154 * 12/1996
WO WO 99/05160 * 2/1999

OTHER PUBLICATIONS

Albert, P.R. et al., "Antisense knockouts:molecular scalpels for the dissection of signal transduction", Trends Pharmacol. Sci., 1994, 15, 250–254.*

Berkow et al. (eds.), The Merck, Manual of Diagnosis and Therapy, Rahway, N.J., 1987, 15th Edition, 2263–2277, 2283–2292, 2301–2310.*

Bernhard et al., "Direct Evidence Linking Expression of Matrix Metalloproteinase 9 (92–kDa gelatinase/collagenase) to the metastatic phenotype in transformed rat embryo cells," Proc. Natl. Acad. Sci. USA, 1994, 91, 4293–4297.*

Birkedal–Hansen, "Proteolytic Remodeling of Extracellular Matrix," *Curr. Op. Cell Biol.,* 1995, 7, 728–735.*

Boggemeyer et al., "Borrelia Burgdorferi Upregulates the Adhesion Molecules E–selecin. P–Selectin. ICAM–1 and VCAM–1 on Mouse Endothelioma Cells in vitro." *Cell Adhes. Commun.*, 1994, 2, 145–157.*

Cook, P.D., "Medicinal chemistry of antisense oligonucleotides—future opportunities", *Anti–Cancer Drug Design*, 1991, 6, 585–607.*

Crooke, S.T. et al., "Pharmacokinetic Properties of Several Novel Oligonucleotide Analogs in mice", *J. Pharmacol. Exp. Therapeutics*, 1996, 277, 923–937.*

Crooke, S.T. et al., "Progress in Antisense Oligonucleotide Therapeutic", *Ann. Rev. Pharmacol. Toxicol.* 1996, 36, 107–129.*

Dean, N.M. et al., "Inhibition of protein kinase C–αexpression in mice after systemic administration of posphorthioate antisense oligodeoxynucledotides", *Proc. Natl. Acad. Sci.,* 1994, 91, 11762–11766.*

DeLisser et al., "Molecular and Functional Aspects of PECAM–1/CD31," *Immunol. Today*, 1994, 15(10), 490–494.*

*Primary Examiner*—James O. Wilson
*Assistant Examiner*—Howard V. Owens, Jr.
(74) *Attorney, Agent, or Firm*—ISIS Patent Department Woodcock Washburn LLP

(57) ABSTRACT

Novel chiral compounds that mimic and/or modulate the activity of wild-type nucleic acids are disclosed. In general, the compounds are phosphorothioate oligonucleotides wherein the 5', and the 3'-terminal internucleoside linkages are chirally Sp and internal internucleoside linkages are chirally Rp.

62 Claims, 7 Drawing Sheets

U.S. PATENT DOCUMENTS

| | | | | | |
|---|---|---|---|---|---|
| 5,399,676 | A | * | 3/1995 | Froehler | 536/23.1 |
| 5,405,938 | A | * | 4/1995 | Summerton et al. | 528/406 |
| 5,405,939 | A | * | 4/1995 | Suhadolnik et al. | 530/322 |
| 5,434,257 | A | * | 7/1995 | Matteucci et al. | 536/24.3 |
| 5,442,049 | A | * | 8/1995 | Anderson et al. | 536/24.5 |
| 5,453,496 | A | * | 9/1995 | Caruthers et al. | 536/24.5 |
| 5,455,233 | A | * | 10/1995 | Spielvogel et al. | 514/44 |
| 5,457,189 | A | * | 10/1995 | Crooke et al. | 536/24.5 |
| 5,466,677 | A | * | 11/1995 | Baxter et al. | 514/44 |
| 5,470,967 | A | * | 11/1995 | Huie et al. | 536/24.3 |
| 5,476,925 | A | * | 12/1995 | Letsinger et al. | 536/23.1 |
| 5,489,677 | A | * | 2/1996 | Sanghvi et al. | 536/22.1 |
| 5,506,212 | A | * | 4/1996 | Hoke et al. | 514/44 |
| 5,512,668 | A | * | 4/1996 | Stec et al. | 536/25.33 |
| 5,514,577 | A | * | 5/1996 | Draper et al. | 435/238 |
| 5,514,788 | A | * | 5/1996 | Bennett et al. | 536/23.1 |
| 5,519,126 | A | * | 5/1996 | Hecht | 536/24.3 |
| 5,523,389 | A | * | 6/1996 | Ecker et al. | 536/23.1 |
| 5,536,821 | A | * | 7/1996 | Agrawal et al. | 536/22.1 |
| 5,541,306 | A | * | 7/1996 | Agrawal et al. | 536/22.1 |
| 5,541,307 | A | * | 7/1996 | Cook et al. | 536/23.1 |
| 5,550,111 | A | * | 8/1996 | Suhadolnik et al. | 514/44 |
| 5,561,225 | A | * | 10/1996 | Maddry et al. | 536/23.1 |
| 5,563,253 | A | * | 10/1996 | Agrawal et al. | 536/22.1 |
| 5,571,799 | A | * | 11/1996 | Tkachuk et al. | 514/47 |
| 5,580,767 | A | * | 12/1996 | Cowsert et al. | 435/375 |
| 5,582,972 | A | * | 12/1996 | Lima et al. | 435/6 |
| 5,582,986 | A | * | 12/1996 | Monia et al. | 435/6 |
| 5,587,361 | A | * | 12/1996 | Cook et al. | 514/44 |
| 5,591,600 | A | * | 1/1997 | Ecker | 435/69.1 |
| 5,591,623 | A | * | 1/1997 | Bennett et al. | 435/375 |
| 5,591,720 | A | * | 1/1997 | Anderson et al. | 514/44 |
| 5,596,086 | A | * | 1/1997 | Matteucci et al. | 536/22.1 |
| 5,599,797 | A | * | 2/1997 | Cook et al. | 514/44 |
| 5,602,240 | A | * | 2/1997 | De Mesmaeker et al. | 536/23.1 |
| 5,607,923 | A | * | 3/1997 | Cook et al. | 514/44 |
| 5,608,046 | A | * | 3/1997 | Cook et al. | 536/23.1 |
| 5,610,289 | A | * | 3/1997 | Cook et al. | 536/25.34 |
| 5,618,704 | A | * | 4/1997 | Sanghvi et al. | 435/91.5 |
| 5,620,963 | A | * | 4/1997 | Cook et al. | 514/44 |
| 5,623,070 | A | * | 4/1997 | Cook et al. | 536/27.6 |
| 5,625,050 | A | * | 4/1997 | Beaton et al. | 536/24.1 |
| 5,633,360 | A | * | 5/1997 | Bischofberger et al. | 536/22.1 |
| 5,658,891 | A | * | 8/1997 | Draper et al. | 514/44 |
| 5,661,134 | A | * | 8/1997 | Cook et al. | 514/44 |
| 5,663,312 | A | * | 9/1997 | Chaturvedula | 536/22.1 |
| 5,670,633 | A | * | 9/1997 | Cook et al. | 536/23.1 |
| 5,677,437 | A | * | 10/1997 | Teng et al. | 536/23.1 |
| 5,677,439 | A | * | 10/1997 | Weis et al. | 536/23.1 |
| 5,681,747 | A | * | 10/1997 | Boggs et al. | |
| 5,681,944 | A | * | 10/1997 | Crooke et al. | 536/24.5 |
| 5,691,461 | A | * | 11/1997 | Ecker et al. | 536/24.32 |
| 5,734,041 | A | * | 3/1998 | Just et al. | 536/25.31 |
| 6,060,456 | A | * | 5/2000 | Arnold, Jr. et al. | 514/44 |
| 6,111,094 | A | * | 8/2000 | Bennett et al. | |
| 6,242,589 | B1 | * | 6/2001 | Cook et al. | |

OTHER PUBLICATIONS

Dimock et al., "An efficient multigram synthesis of monomers for the preparation of novel oligonucleotides containing isosteric non–phosphorous backbones", *Nucleosides &Nucleotides*, 1997, 16(7–9), 1629–1632.*

Downward, "The ras Superfamily of Small GTP–binding proteins," *TIBS,* 15, 1990, 469–472.*

Englicsh, U. et al., "Chemically Modified Oligonucleotides as Probes and Inhibitors", *Angew. Chem. Int. Ed. Eng.,* 1991, 30, 613–629.*

Griffiths, C.E.M. et al., "Keratinocyte Intercellular Adhesion Molecule–1 (ICAM–1) Expression Preceedes Derman T Lymphocyte Infiltration in Allegric Contact Dermatitis (*Rhus dermatitis* )", *Am. J. Pathology.,* 1989, 135, 1045–1053.*

Gum et al., "Stimulation of 92–kDa Gelatinase B Promoter Activity by ras Is Mitogen–activated Protein Kinase Kinase 1–independent and Requires Multiple Transcription Factor Binding Sites Including Closely Spaced PEA3/ets and AP–1 Sequences," *J. Biol. Chem.,* 1996, 271(18), 10672–10680.*

Guzavez et al., "Synthesis of $^{14}$C–Radiolabeled Oligonucleotides with a Novel Phosphoramidite Reagent", *Bioorg. Med. Chem. Lett.* 1998, 8, 1123–1126.*

Hakugawa et al., "The Inhibitory Effect of Anti–Adhesion Molecule Antibodies on Eosinophil Infiltration in Cutaneous Late Phase Response in Balb/c Mice Sensitized with Oval–bumin (OVA)," *J. Dermatol.,* 1997, 24, 73–79.*

Hegemann, L. et al. "Biochemical Pharmacology of Protein Kinase C and its Relevance for Dermatology", *Pharmacology of the Skin,* Mukhtar, H. (ed.), CRC Press, Boca Raton, 1992, Ch.22, 357–268.*

Himelstein et al., "Metalloproteinases in Tumor Progression: The Contribution of MMP–9," *Invasion & Metastsis,* 1994–95, 14, 246–258.*

Ho, V.C. et al., "Treatment of severe lichen planus with cyclosporine", *J. Am. Acad. Dermatol.,* 1990, 22, 64–68.*

Hua et al., "Inhibition of Matrix Metalloproteinase 9 Expression by a Ribozyme Blocks Metastasis in a Rat Sarcoma Model System," *Cancer Res.*, 1996, 56, 5279–5284.*

Hurtenback et al. "Prednisolone Reduces Experimental Arthritis and Inflammatory Tissue Destruction in Scid Mice Infected with Borrelia Burgdorferi," *Int. J. Immunopharmac*, 1996, 18(5), 281–288.*

Iyer, R.P. et al., "The Automated Synthesis of Sulfur–Containing Oligodeoxyribonucleotides Using 3H–1, 2–Benzodithiol–3–one 1,1–Dioxide as a Sulfur–Transfer Reagent", *J. Org. Chem.*, 1990, 55, 4693–4699.*

Kabanov, A.V., "A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330.*

Katocs, A.S. et al., "Biological Testing", *Remington's Pharmaceutical Sciences*, 18th Ed., Gennaro (ed.). Mack Publishing Co., Easton, PA. 1990. Ch. 27, 484–494.*

Kerr et al., "Growth Factors Regulate Transin Gene Expression by c–fos–Dependent and c–fos–Independent Pathways," *Science*, 1988, 242, 1424–1427.*

Kerr et al., "TGF–β1 Inhibition of Transin/Stromelysin Gene Expression is Mediated Through a Fos Binding Sequence," *Cell*, 1990, 61, 267–278.*

Kroschwitz, J.I., "Polynucleotides", *Concise Encyclopedia of Polymer Science and Engineering*, 1990, John Wiley & Sons, New York, 858–859.*

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*, 1989, 86, 6553–6556.*

Lisby, S. et al., "Intercellular adhesion molecule–1 (ICAM–1) expression correlated to inflammation", *Br. J. Dermatol.*, 1989, 120, 479–484.*

Litwin et al., "Novel Cytokine–independent Induction of Endothelial Adhesion Molecules Regulated by Platelet/Endothelial Cell Adhesion Molecule (CD31)," *J. Cell Biol.*, 1997, 13911), 219–228.*

Manoharan, M. et al., "Lipidic Nucleic Acids", *Tetrahedron Letts.*, 1995, 36, 3651–3654.*

Manoharan M. et al., "Cholic Acid–Oligonucleotide Conjugates for Antisense Applications", *Bioorganic Med. Chem. Letts*. 1994, 4, 1053–1060.*

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.*

Manoharan, M. et al., "Chemical Modifications to Improve Uptake and Bioavailability of Antisense Oligonucleotides", *Annals NY Acad. Sciences*, 1992, 660, 306–309.*

Manoharan M. et al., "Oligonucleotide Conjugates: Alteration of the Pharmacokinetic Properties of Antisense Agents", *Nucleosides and Nucleotides*, 1995, 14, 969–973.*

Martin P., "Ein neuer Zugang zu 2–40 –O–Alkylribonucleosiden und Eigenschaften deren Oligonucleotide", *Helvetica Chemica Acta*, 1995, 78, 486–504.*

Mishra, R.K. et al., "Improved leishmanicidal effect of phosphorotioate antisense oligonucleotides by LDL–medicated delivery", *Biochim. Et Biophysica*. 1995, 1264, 229–237.*

Newman, "Perspective Series: Cell Adhesion in Vascular Biology," *The Biology of PECAM–1J. Clin.Invest.*, 1997, 99(1), 3–7.*

Nies, A.S. et al., "Principles of Therapeutics", *Goodman & Gilman's The Pharmacological Basis of Therapeutics*, 9th Ed., Hardman et al. (eds.), McGraw–Hill, New York, NY, 1996. Ch. 3, 43–62.*

Oberhauser, B. et al., "Effective incorporation of 2'–O–methyl–oligonucleotides into liposomes and enhanced cell association through modification with thiocholesterol", *Nucl. Acids Res.*, 1992, 20, 533–538.*

Regezi et al., "Vascular adhesion molecules in oral lichen planus", *Oral Surg. Oral Med. Oral Pathol.*, 1996, 81, 682–690.*

Ruoslahti, "How Cancer Spreads," *Sci. Am.*, 1996, 72–77.*

Saison–Behmoaras, T. et al., "Short modified antisense oligonucleotides directed against Ha–ras point mutation induce selective cleavage of the mRNA and inhibit T24 cells proliferation", *EMBO J.*, 1991, 10, 1111–1118.*

Sanghvi et al., "Concept, Discovery and Development of MMI Linkage: Story of a Novel Linkage for Antisense Contructs", *Nucleosides & Nucleotides*, 1997, 16(7–9), 907–916.*

Sanghvi, Y.S., "Heterocyclic Base Modifications in Nucleic acids and their Applications in Antisense Oligonucleotides", *Antisense Research and Applications*, Crooke et al. (Eds.), CRC Press, Boco Raton, 1993, Chapter 15, 273–288.*

Secrist, J.A. et al., "Synthesis and Biological Activity of 4'–Thionucleosides", *10th International Rowntable: Nucleosides. Nucleotides and their Biological Applications*Sep. 16–20 1992, Abstract 21, Park City, Utah, 40.*

Shea, R.G. et al., "Synthesis, hybridization properties and antiviral activity of lipid–oligodeoxynucletide conjugates", *Nucl. Acids Res.*, 1990, 18, 3777–3783.*

Shiohara et al., "Fixed drug Eruption: Expression of Epidermal Keratinocyte Intercellular Adhesion Molecule–1 (ICAM–1)", *Arch. Dermatol.*, 1989, 125, 1371–1376.*

Stetler–Stevenson et al., "Tumor Cell Interactions with the Extracellular Matrix During Invasion and Metastasis, " *Annu. Rev. Cell Biol.*, Palade, G.E. et al. (eds.), 1993, 9, 541–573.*

Svinarchuk, F.P. et al., "Inhibition of HIV proliferation in MT–4 cells by antisense oligonucleotide conjugated to lipophilic groups", *Biochimie*, 1993, 79, 49–54.*

Swayze et al., "The Synthesis of N,N'–O–Trisubstituted Hydroxylamines via a Mild Reductive Aklylation Procedure: An Improved Synthesis of the MMI Backbone", *Synlett*, 1997, 859–861.*

Swayze et al., "The Synthesis of the Sixteen Possible 2'–O–Methyl MMI Dimer Phosphoramidites: Building Blocks for the Synthesis of Novel Antisense Oligonucleotides", *Nucleosides & Nucleotides*, 1997, 16(7–9), 971–972.*

U.S. Congress, Office of Technology Assessment, "The State–of–the–art in Genetic Screening", *Genetic Monitoring and Screening in the Workplace*, OTA–BA–455, U.S. Government Printing Office, Washington, D.C., 1990, Ch. 5, 75–99.*

Wahlestedt, C. et al., "Antisense oligodeoxynucleotides to NMDA–R1 receptor channel protect cortical neurons from excitotoxicity and reduce focal ischaemic infarctions", *Nature*, 1993, 363, 260–263.*

Wahlestedt, C. et al., "Modulation of Anxiety and Neuropeptide Y–Y1 Receptors by Antisense Oligodeoxynucleotides", *Science*, 1993, 259, 528–531.*

Ausubel, F.M. et al. (Eds.), *Current Protocols in Molecular Biology*, Current Publications, 1993.*

Sambrook, J. et al. (Eds.), *Molecular Cloning, A Laboratory Manual*, Second Ed., Cold Spring Harbor Laboratory Press, 1989.*

Green and Wuts, *Protective Groups in Organic Synthesis*, 2d edition, John Wiley & Sons, New York, 1991.*

Agrawal et al. (eds.), "Methods of Molecular Biology", in *Protocols for Oligonucleotide Conjugates*, Agrawal, S. (ed.), Humana Press, New Jersey, 1994, vol. 26, 1–72.*

Alul, R.H. et al., "Oxalyl–CPG: a labile support for synthesis of sensitive oligonucleotide derivatives", *Nucl. Acid Res.*, 1991, 19, 1527–1532.*

Bachelin et al., "Structure of a stereoregular phosphorothioate DNA/RNA duplex," *Nat. Struct. Biol.*, 1998, 5(4), 271–276.*

Baker, B.F. et al., "2'–O–(2–Methoxy)ethyl–modified Anti–intercellular Adhesion Molecule 1 (ICAM–1) Oligonucleotides Selectively Increase the ICAM–1 Translation Initiation Complex in Human Umbilical Vein Endothelial Cells". *J. Biol. Chem.*, 1997, 272, 11994–12000.*

Beaucage, S.L. et al., "Advances in the Synthesis of Oligonucleotides by the Phosphoramidite Approach", *Tetrahedron*, 1992, 48, 2223–2311.*

Brown, T. et al., "A New Base–stable Linker for Solid–Phase Oligonucleotide Synthesis," *J.Chem. Soc. Chem. Comm.*, 1989, 891–893.*

Burgers, P.M.J. et al., "A Study of the Mechanism of DNA Polymerase I from *Escherichia coli* with Diastereometric Phosphorothioate Analogs of Deoxyadenosine Triphosphate", *J. Biol. Chem.*, 1979, 254, 6889–6893.*

Crooke, S.T. et al., "Kinetic characteristics of *Escherichia coli* RNase H1: cleavage of various antisense oligonucleotide–RNA duplexes", *Biochem. J.*, 1995, 312, 599–608.*

Damha, M.J. et al., "An improved procedure for derivatization of controlled–pore glass beads for solid–phase oligonucleotide synthesis", *Nucl. Acids Res.*, 1990, 18, 3813–3821.*

Delgado, C. et al., "The Uses and Properties of PEG–Linked Proteins", *Crit. Rev. in Therapeutic Drug Carrier Sys.*, 1992, 9, 249–304.*

Efimov, V.A. et al., "New efficient sulfurizing reagents for the preparation of oligodeoxyribonucleotide phosphorothioate analogues", *Nucl. Acids Res.*, 1995, 23, 4029–4033.*

Eliel, E.L. et al., "Asymmetric Syntheses Based on 1,3–Oxathianes. 1. Scope of the Reactions," *J. Am. Chem. Soc.*, 1984, 106(10), 2937–2942.*

Eliel, E.L. et al., "Neighboring Group Participiption by Oxygen in the Solvolysis of Acyclic γ–Alkoxy Substituted ρ–Toluensesulfonates," *J. Org. Chem.*, 1985, 50, 2707–2711.*

Eliel, E.L. et al., "Neighboring Group Participation by Sulfur Involving Four–Membered–Ring Intermediates (RS–4)," *J. Am. Chem. Soc.*, 1985, 107(10), 2946–2952.*

Eliel, E.L. et al. "Highly Stereoselective Syntheses Involving N–Alkyl–4,4,7α–trimethyl–trans–octahydro–1,3–benzoxazine Intermediates," *J. Org. Chem.*, 1990, 55, 2114–2119.*

Eliel, E.L. et al., "Asymmetric Synthesis of (R)–(+)–Ethylmethyl–n–Propylcarbinol in High Enantiometric Purity. A 1,3–Oxathiane Detrived from (+)–Pulegone as Chiral Adjuvant," *Terra Lett.*, 1981, 22(30), 2855–2858.*

Froehler, B.C., "Oligodeoxynucleotides Synthesis: H–Phosphonate Approach," in *Protocols for Oligonuceleotides and Analogs: Synthesis and Properties*, Agrawal S. (ed.), Humana Press, 1993, Ch. 4, 63–80.*

Gait, M. J. ed., "An Introduction to Modern Methods of DNA Synthesis," *Oligonucleotide Synthesis, A Practical Approach*, IRL Press, Oxford, 1985, IRL Press, Oxford, Ch. 1, 1–22.*

Griffiths, A.D. et al., "Stereospecificity of nucleases towards phosphorothioate–substituted RNA: stereochemistry of transcription by T7 RNA polymerase," *Nucl. Acids Res.*, 1987, 15(10), 4145–4162.*

Hacia, J.G. et al., "Phosphorothioate Oligonucleotide–Directed Triple Helix Formation," *Biochem.*, 1994, 33, 5367–5369.*

Hamm, M. L. et al., "Incorporation of 2'–Deoxy–2'–mercaptocytidine into Oligonucleotides via Phosphoramidite Chemistry," *J. Org. Chem*, 1997, 62, 3415–3420.*

He, X–C. et al., "Highly Enantioselective Syntheses of α–Hydroxyacids Using N–Benzyl–4,4,7αTrimethyl–Trans–Octahydro–1,3–Benzoxazine as a Chiral Adjuvant," *Tetrahedron*, 1987, 43(21), 4979–4987.*

Iyer, R.P. et al., "3H–1,2–Benzodithiole–3–one, 1.1–Dioxide as an Improved Sulfurizing Reagent in the Solid–Phase Synthesis of Oligodeoxyribonucleoside Phosphorothioates", *J. Am. Chem, Soc.*, 1990, 112, 1253–1254.*

Jin, Y. et al., "Stereoselective Synthesis of Dithymidine Phosphorothioates Using Xylose Derivatives as Chiral Auxiliaries," *J. Org. Chem.*, 1998, 63, 3647–3654.*

Jung, M.E., "New Gem– and Vic–Disubstituent Effects on Cyclizations," *Synlett*, 1999, S1, 843–846.*

Kamer, P.C.J. et al., "An Efficient Approach Toward the Synthesis of Phosphorotioate Diesters via the Schonberg Reaction", *Tetrahedron Letts*, 1989, 30, 6757–6760.*

Koziolkiewicz, M. et al., "Stability of Stereoregular Oligo–(nucleoside Phosphorothioate)s in Human Plasma: Diastereoselectiviy of Plasma 3'–Exonuclease," *Antisense Nucl. Acid Drug Dev.*, 1997, 7, 43–48.*

Koziolkewicz, M. et al., "Stereodifferentiation—the effect of P chirality of oligo(nucleoside phosphorothioates) on the activity of bacterial RNase H," *Nucl. Acids Res.*, 1995, 23(24), 5000–5005.*

Koziolkiewicz. M. et al., "Enzymatic Assignment of Diastereomeric Purity of Stereodefined Phosphorothioate Oligonucleotides," *Antisense Nucl. Acid Drug Dev.*, 1999, 9, 171–181.*

Koziolkewicz, M. et al., "Stability of Stereoregular Oligo–(nucleoside phosphorothioate) s in Human Cells: Diastereoselectivity of Cellular 3'–Exonuclease," *Nucleosides & Nucleoides*, 1997, 16(7–9), 1677–1682.*

Lackey, D.B. et al., "Biochemical synthesis of chirally pure Rp oligonucleotide phosphorothioates," *Biotechnol Lett.*, 1997, 19(5), 475–478.*

Lima, W.F. et al., "Binding Affinity and Specificity of *Escherichia coli* Rnas H1: Impact on the Kinetics of Catalysis of Antisense Oligonucleotide–RNA Hybrids," *Biochemistry*, 1997, 36, 390–398.*

Ludwig, J. et al., "Rapid and Efficient Synthesis of Nucleoside 5'–O–(1–Thiotriphosphates), 5'–Triphosphates and 2',3'–Cycloposphorothioates Using 2'Chloro–4H–1,3,2–benzodioxaphosphorin–4–one", *J. Org. Chem.*, 1989, 54, 631–635.*

Lynch et al., "Asymmetric Synthesis Based on 1,3–Oxathianes. 2. Syntheses of Chiral Ternary α–Hydroxy Aldehydes, α–Hydroxy Acids, Glycols (RR'C(OH)$CH_2$OH), and Carbinols (RR'C(OH)$CH_3$ ) in High Enantiomeric Purity," *J. Am. Chem. Soc.*, 1984, 106, 2943–2948.*

Minshull, J. et al., "The use of single–stranded DNA and RNase H to promote quantitative 'hybrid arrest of translation' of mRNA/DNA hybrids in reticulocyte lysate cell–free translations", *Nucl. Acids. Res.*, 1986, 14., 6433–6451.*

Ouchi, T. et al., "Synthesis and Antitumor Activity of Poly (Ethylene Glycol)s Linked to 5'–Fluorouracil via a Urethane or Urea Bond", *Drug Des. & Disc.*, 1992, 9, 93–105.*

Polushin, N. N. et al., "Synthesis of Oligonucleotides Containing 2'–Azido–and 2'–Amino–2'–deoxyuridine Using Phosphotriester Chemistry," *Tetrahedron Letts.*, 1996, 37(19), 3227–3230.*

Rao, M.W. et al., "Dibenzoyl Terrasulphide—A Rapid Sulphur Transfer Agent in the Synthesis of Phosphorothioate Analogues of Oligonucleotides", *Tetrahedron Letts.*, 1992, 33, 4839–4842.*

Ravasio, N. et al., "Selective Hydrogenations Promoted by Copper Catalysts 1. Chemoselectivity, Regioselectivity, and Stereoselectivity in the Hydrogenation of 3–Substituted Steroids", *J. Org. Chem.*, 1991, 56, 4329–4333.*

Sierzchala, A. et al., "Oxathiaphospholane Method of Stereocontrolled Synthesis of Diribonucleoside 3', 5'–Phosphorotiates," *J. Org. Chem.*, 1996, 61, 6713–6716.*

Slim, G. et al., "Configurationally defined phosphorotioate–containing oligoribonucleotides in the study of the mechanism of cleavage of hammerhead ribozymes," *Nucl. Acids Res.*, 1991, 19(6), 1183–1188.*

Stec, W.J. et al., "Deoxyribonucleoside 3'–O–(2–Thio– and 2–Oxo–"spiro"–4,4–pentamethylene–1,3,2–oxathiaophosholane)s: Monomers for Stereocontrolled Synthesis of Oligo(deoxyribonucleoside phosphorothioate)s and Chimeric PS/PO Oligonucleotides," *J. Am. Chem. Soc.*, 1998, 120, 7156–7167.*

Stec, W.J. et al., "Stereocontrolled Synthesis of Oligo-(nucleoside phosphorothioate)s", *Angew: Chem. Int. Ed. Engl.*, 1994, 33, 709–722.*

Stec, W.J. et al., "Bis (O,O–Diisopropoxy Phosphinothioyl) Disulfide—A Highly Efficient Sulfurizing Reagent for Cost–Effective Synthesis of Oligo(Nucleoside Phosphorothioate)s", *Tetrahedron Letts*, 1993, 34, 5317–5320.*

Stec, W.J. et al., "Diastereomers of Nucleoside 3'–O(2–THio–1,3,2–ozathia(selena)phospholanes): Building Blocks for Stereocontrolled Syntheis of Oligo(nucleoside Phosphorothioate)s,"*J. Am. Chem. Soc.*, 1995, 117(49), 12019–12029.*

Tang, J. et al., "Enzymatic Synthesis of Stereoregular (all Rp) Oligonucleotide Phosphorothioate and its Properties," *Nuceosides & Nucleotides*, 1995, 14(3–5), 985–990.*

Thomson, J. B. et al., "Synthesis and Properties of Diuridine Phosphate Analogues Containing Thio and Amino Modifications," *J. Org. Chem.*, 1996, 61, 6273–6281.*

Vu, H. et al, "Internucleotide Phosphite Sulfurization with Tetraethylthiuram Disulfide. Phosphorothioate Oligonucleotide Synthesis via Phosphoramidite Chemistry", *Tetrahedron Letts.*, 1991, 32, 3005–3008.*

Wang, J.C. et al., "A Stereoselective Synthesis of Dinucleotide PhosphorothioateTriesters through a Chiral Indol–ox–azaphosphorine Intermediate," *Terra. Lett.*, 1997, 38(5), 705–708.*

Wang, J.C. et al., "A Stereoselective Synthesis of Dinucleotide Phosphorothioates Using Chiral Indol–oxazaphosphorine Intermediates," *Tetra. Lett.*, 1997, 38(22), 3797–3800.*

Wright. P. et al., "Large Scale Synthesis of Oligonucleotides via phosphoramidite Nucleosides and a High–loaded Polystyrene Support", *Tetrahedron Letts.*, 1993, 34, 3373–3376.*

Xu, Q. et al., "Efficient introduction of phosphorothioates into RNA oligonucleotides by 3–ethoxy–1,2,4–dithiazoline–5–one (EDITH)", *Nucl. Acids Res.*, 1996, 24, 3643–3644.*

Xu, Q. et al., "Use of 1,2,4–dithiazolidine (DtsNH) and 3–ethoxy–1,2,4–dithiazoline–5–one(Edith) for synthesis of phosphorothioate–containing oligodeoxyribonucleotides", *Nucl. Acids. Res.*, 1996, 24, 1602–1607.*

Koziolkiewicz, M. et al., "Effect of P–chirality of oligo(deoxyribonucleoside phosphorothioate)s on the activity of terminal deoxyribonucleotidyl transferase," *FEBS Letters*, Aug. 28, 1998, 434(1–2), 77–82.*

Lesnikowski, Z. et al., "Studies on stereospecific formation of P–chiral internucleotide linkage, Synthesis of (RP, RP)–and (SP,SP)–thymidylyl(3, 5)thymidyly(3.5)thymidineDI(0,0–phosphorothioate) usingf 2–nitrobenzyl group as a new S–protection," *Tetrahedron Letters*,1989, 30(29), 3821–3824.*

Stec, W. et al., "Novel route to oligodeoxyribonucleoside phosphorothioates stereocontrolled synthesis of P–chiral oligodeoxyribonucleoside phosphorothioates," *Nucleic Acids Research*, 1991, 19(21), 5883–5888.*

Torrence, P.F., "The Chemistry and biochemistry of purine- and pyrimidine nucleoside antiviral and antitumor agents." *Drugs and the Pharmaceuticals Sciences*, 1984, 24, 113–176.*

* cited by examiner

Rp isomer

Sp isomer

OLIGONUCLEOLOTIDES HAVING SITE SPECIFIC CHIRAL PHOSPHOROTHIOATE INTERNUCLEOSIDE LINKAGES

Matter enclosed in heavy brackets [ ] appears in the original patent but forms no part of this reissue specification; matter printed in italics indicates the additions made by reissue.

CROSS REFERENCE TO RELATED APPLICATIONS

This patent application is a continuation-in-part of application Ser. No. 09/115,027, filed Jul. 14, 1998, now U.S. Pat. No. 6,242,589 entitled "Phosphorothioate Oligonucleotides Having Modified Internucleotide Linkages", the content of which is incorporated herein by reference in its entirety.

FIELD OF THE INVENTION

This invention relates to the design and synthesis of nuclease resistant phosphorothioate oligonucleotides which are useful for therapeutics, diagnostics and as research reagents. Phosphorothioate oligonucleotides are provided in which all of the internucleoside linkages are chiral. Such compounds are resistant to nuclease degradation and are capable of modulating the activity of DNA and RNA.

BACKGROUND OF THE INVENTION

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect can be obtained with minimal side effects. It is therefore a general object of such therapeutic approaches to interfere with or other-wise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as therapeutic agents in human clinical trials against various disease states, including use as antiviral agents.

In addition to such use as both indirect and direct regulators of proteins, oligonucleotides also have found use in diagnostic tests. Such diagnostic tests can be performed using biological fluids, tissues, intact cells or isolated cellular components. As with gene expression inhibition, diagnostic applications utilize the ability of oligonucleotides to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides are also widely used as research reagents. They are useful for understanding the function of many other biological molecules as well as in the preparation of other biological molecules. For example, the use of oligonucleotides as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides, both natural and synthetic, are employed as primers in such PCR technology.

Oligonucleotides are also used in other laboratory procedures. Several of these uses are described in common laboratory manuals such as Molecular Cloning, A Laboratory Manual. Second Ed., J. Sambrook, et al., Eds., Cold Spring Harbor Laboratory Press. 1989; and Current Protocols In Molecular Biology. F. M. Ausubel, et al., Eds., Current Publications, 1993. Such uses include as synthetic oligonucleotide probes, in screening expression libraries with antibodies and oligomeric compounds. DNA sequencing, in vitro amplification of DNA by the polymerase chain reaction, and in site-directed mutagenesis of cloned DNA. See Book 2 of Molecular Cloning. A Laboratory Manual, supra. See also "DNA-protein interactions and The Polymerase Chain Reaction" in Vol. 2 of Current Protocols In Molecular Biology, supra.

A number of chemical modifications have been introduced into oligonucleotides to increase their usefulness in diagnostics, as research reagents and as therapeutic entities. Such modifications include those designed to increase binding to a target strand (i.e. increase melting temperatures, Tm), to assist in identification of an oligonucleotide OR an oligonucleotide-target complex, to increase cell penetration, to stabilize against nucleases and other enzymes that degrade or interfere with the structure or activity of the oligonucleotides, to provide a mode of disruption (terminating event) once sequence-specifically bound to a target, and to improve the pharmacokinetic properties of the oligonucleotide.

The complementarity of oligonucleotides has been used for inhibition of a number of cellular targets. Complementary oligonucleotides are commonly described as being antisense oligonucleotides. Various-reviews describing the results of these studies have been published including Progress In Antisense Oligonucleotide Therapeutics, Crooke, S. T., and Bennett. C. F., Annu. Rev. Pharmacol. Toxicol., 1996, 36, 107–129. These oligonucleotides have proven to be powerful research tools and diagnostic agents. Certain oligonucleotides that have been shown to be efficacious are currently in human clinical trials.

The pharmacological activity of oligonucleotides, like other therapeutics, depends on a number of factors that influence the effective concentration of these agents at specific intracellular targets. One important factor for oligonucleotides is the stability of the species in the presence of nucleases. It is unlikely that unmodified, naturally-occurring oligonucleotides will be useful therapeutic agents because they are rapidly degraded by nucleases. The limitations of available methods for modification of the phosphate backbone of unmodified oligonucleotides have led to a continuing and long felt need for other modifications which provide resistance to nucleases and satisfactory hybridization properties for antisense oligonucleotide diagnostics and therapeutics.

Oligonucleotides having phosphorothioate modified backbones have shown therapeutic effects against numerous targets. This success is due in part to the increased nuclease resistance of the phosphorothioate backbone relative to the naturally occurring phosphodiester backbone. The phosphorothioate linkage unlike the phosphodiester linkage has 2 enantiomers, $R_P$ and $S_P$. It has been shown that a 3'-$R_P$ linkage is labile to at least one exonuclease in the cytosol of HUVEC cells (Kiziolkiewicz et al. Nucleosides and Nucleotides, 1997, vol. 16, pp. 1677–1682). See also Koziolkiewicz et al., Antisense Nucleic Acid Drug Dev., 1997, 7, 43–48; Koziolkiewicz, Maria, Gendaszewska. Edyta, Maszewska, Maria, Stability of Stereoregular Oligo (nucleoside phosphorothioate)s in Human Cells; Diastereoselectivity of Cellular 3'-Exonuclease, Nucleosides Nucleotides 1997, 16(7–9) 1677–1682.

A specific feature of oligonucleotides as drugs is that they must be stable in vivo long enough to be effective. Consequently, much research has been focused on enhancing the stability of oligonucleotide therapeutics while maintaining their specific binding properties. Recently, several groups have reported that chiral phosphorothioate oligonucleotide analogs have enhanced binding properties (Rp isomer) to the target RNA as well as significant stabilization to exonucleases (Sp isomer) (See Koziolkiewicz et al., Antisense & Nucleic acid drug development, 1997, 7, 43–8; Burgers et al., J. Biol. Chem., 1979, 254, 6889–93; and Griffiths et al., Nucleic Acids Research, 1987, 15, 41452–62).

Presently, there is no method to prepare P-chiral oligonucleotides in large scale. Current methods include synthesis and chromatographic isolation of stereoisomers of the chiral building blocks. (Stec et al., Angers: Chem. Int. Ed. Engl., 1994, 33, 709; Stec et al., J. Am. Chem. Soc., 1995, 117, 12019; and Stec W. J., Protocols for Oligonucleotides and Analogs: Synthesis and Properties, edited by Sudhir Agrawal, p. 63–80, (1993, Humana Press) and references cited therein). This method suffers from the non-stereospecific synthesis of the synthon. Recently, Just and coworkers presented the use of a chiral auxiliary to form dinucleotide phosphorothioate triesters in 97% ee (Wang, J. C., and Just G., Tetrahedron Letters, 1997, 38, 705–708). However, there was reported difficulty in removing the chiral auxiliary protecting group at phosphorous. This method has yet to be tested for convenient large scale automated synthesis.

Stereoregular phosphorothioate analogs of pentadecamer 5'-d(AGATGTTTGA GCTCT)-3' were synthesized by the oxathiaphospholane method (Koziolkiewicz et al., Nucleic Acids Res., 1995, 23, 5000–5005). There diastereomeric purity was assigned by means of enzymic degradation with nuclease P1 and independently, with snake venom phosphodiesterase. DNA-RNA hybrids formed by phosphorothioate oligonucleotides (PS-oligos) with the corresponding complementary pentadecarbonucleotide were treated with bacterial RNase H. The DNA-RNA complex containing the PS-oligo of [all-RP] configuration was found to be more susceptible to RNase H-dependent degradation of the pentadecarbonucleotide compared with hybrids containing either the [all-SP] counterpart or the so called 'random mixture of diastereomers of the pentadeca(nucleoside phosphorothioate). This stereodependence of RNase H action was also observed for a polyribonucleotide (475 nt) hybridized with these phosphorothioate oligonucleotides. The results of melting studies of PS-oligo-RNA hybrids allowed a rationalization of the observed stereodifferentiation in terms of the higher stability of heterodimers formed between oligoribonucleotides and [all-RP]-oligo(nucleoside phosphorothioates), compared with the less stable heterodimers formed with [all-SP]-oligo(nucleoside phosphorothioates) or the random mixture of diastereomers.

(S)-1-(indol-2-yl)-propan-2-ol was used as a chiral auxiliary to form a dinucleotide phosphorothioate triester in 97% ee (Wang et al., Tetrahedron Lett., 1997, 38, 705–708).

A stereoselective preparation of dinucleotide phosphorothioates with a diastereomeric excess of >98%, using hydroxy(indolyl)butyronitrile 1 as chiral auxiliaries, is reported (Wang et al., Tetrahedron Lett., 1997, 38, 3797–3800).

1,2-O-Cyclopentylidene-5-deoxy-5-isopropylamino-D-xylofuranose and its enantiomer were used as chiral auxiliaries to form, respectively, Sp and Rp dithymidine phosphorothioates in 98% diastereomeric excess, using phosphoramidite methodologies and 2-bromo-4.5-dicyanoimidazole as catalyst (Jin et al., J. Org. Chem., 1998, 63, 3647–3654).

Oligonucleotide phosphorothioates were synthesized using prokaryotic DNA polymerase and oligonucleotide template/primer (Lackey et al., Biotechnol. Lett., 1997, 19, 475–478). The method facilitates the recovery of DNA polymerase and template/primer and is successful at the milligram scale. Thus, reusable template/primers were designed to specify the synthesis of an oligonucleotide (GPs0193) complementary to a sequence in exon 7 of the human immunodeficiency virus genome. Extension of the 3'-terminus by DNA polymerase utilizing dNTPS(Rp+Sp) substrates produced the specified oligonucleotide phosphorothioate with the chirally pure (Rp) stereochem. The biochemical synthesis was essentially complete within 60 min (compared with 24 h for automated solid phase synthesis). and produced <5% intermediate length oligonucleotide products, corresponding to a stepwise yield of >99.7% for the addition of each nucleotide.

Phosphorothioate oligodeoxyribonucleotides were tested for their ability to recognize double-helical DNA in two distinct triple helix motifs (Hacia et al., Biochemistry, 1994, 33, 5367–5369). Purine-rich oligonucleotides containing a diastereomeric mixture of phosphorothioate or stereoregular (all Rp) phosphorothioate linkages are shown to form triple-helical complexes with affinities similar to those of the corresponding natural phosphodiester oligonucleotides. In contrast, pyrimidine-rich phosphorothioate oligonucleotides containing a mixture of diastereomeric or stereoregular (all Rp) linkages do not bind to double-helical DNA with measurable affinity. These observations have implications for triple helix structure and for biological applications.

An enzymatic protocol has been established for the synthesis of Stereoregular (all Rp) oligodeoxyribonucleotide phosphorothioates. A 25-mer oligodeoxynucleotide phosphorothioate has been synthesized and studied for biophysical and biochemical properties (Tang et al., Nucleosides and Nucleotides, 1995, 14, 985–990).

Stability of oligo(nucleoside phosphorothioate)s (PS-oligos) in HUVEC (human umbilical vein endothelial cells) has been studied (Koziolkiewicz et al., Nucleosides and Nucleotides, 1997, 16, 1677–1682). Cytosolic fraction of HUVEC possesses 3'-exo-nucleolytic activity which is responsible for degradation of natural and PS-oligomers. The enzyme is Rp-specific, i.e. it cleaves internucleotide phosphorothioate function of Rp- and not Sp-configuration at phosphorus atom.

Enzymatic hydrolysis of stereoregular oligodeoxyribonucleoside phosphorothioates (PS-oligos) synthesized via the oxathiaphospholane method has been used for assignment of their diastereomeric purity (Koziolkiewicz et al., Antisense Nucleic Acid Drug Dev., 1999, 9, 171–181). For this purpose, two well-known enzymes of established diastereoselectivity, nuclease P1 and snake venom phosphodiesterase (svPDE) have been used. However, because of some disadvantageous properties of svPDE, a search for other [Rp]-specific endonucleases was undertaken. Extracellular bacterial endonuclease isolated from Serratia marcescens accepts PS-oligos as substrates and hydrolyzes phosphorothioate bonds of the [Rp] configuration, whereas internucleotide [Sp]-phosphorothioates are resistant to its action. Cleavage experiments carried out with the use of unmodified and phosphorothioate oligonucleotides of different sequences demonstrate that the Serratia nuclease is more selective in recognition and hydrolysis of oligodeoxyribonucleotides than previously reported. The substrate specificity exhibited by the enzyme is influenced not only by the nucleotide sequence at the cleavage site but also by the length and base sequence of flanking sequences. The Serratia nuclease can be useful for analysis of diastereomeric purity of stereodefined phosphorothioate oligonucleotides, but because of its sequence preferences, the use of this enzyme in conjunction with svPDE is more reliable.

The first NMR solution structure of a DNA/RNA hybrid containing stereoregular Rp-phosphorothioate modifications of all DNA backbone linkages is presented.

The complex of the enzymically synthesized phosphorothioate DNA octamer (all-Rp)-d(GCGTCAGG) and its complementary RNA r(CCUGACGC) had an overall conformation within the A-form family (Bachelin et al., Nat. Struct. Biol., 1998, 5, 271–276). Most helical parameters and the sugar puckers of the DNA strand assume values intermediate between A- and B-form. The close structural similarity with the unmodified DNA/RNA hybrid of the same sequence may explain why both the natural and the sulfur-substituted complex can be recognized and digested by RNase H.

New monomers, 5'-O-DMT-deoxyribonucleoside 3'-O-(2-thio-"spiro"-4,4-penta-methylene-1,3,2-oxathiaphospholane)s, were prepared and used for the stereo-controlled synthesis of PS-Oligos via the oxathiaphospholane approach (Stec et al., J. Am. Chem. Soc., 1998, 120, 7156–7167). These monomers and their 2-oxo analogs were used for the synthesis of "chimeric" constructs (PS/PO-Oligos) possessing phosphate and P-stereo-defined phosphorothioate inter-nucleotide linkages. The yield of a single coupling step is approximately 92–95%, and resulting oligomers are free of nucleobase- and sugar-phosphorothioate backbone modifications. Thermal dissociation studies showed that for hetero-duplexes formed by [Rp]-, [Sp]-, or [mix]-PS/PO-T10 with dA12, dA30, or poly(dA), for each template, the melting temperatures as well as free Gibbs' energies of dissociation process, are virtually equivalent. Stereochemical evidence derived form crystallographic analysis of one of the oxathiaphospholane monomers strongly supports the participation of pentacoordinate intermediates in the mechanism of the oxathiaphospholane ring-opening condensation.

The DBU-assisted 1,3,2-oxathiaphospholane ring opening condensation of the separate diastereomers of 5'-O-DMT-2'-O-TBDMS-ribonucleoside-3'-O-(2-thiono-1,3,2-oxathiaphospholane)s with 2'-TBDMSi-protected ribonucleoside bound to the solid support via the 3'-oxygen occurs with 96–100% stereospecificity and gives, after deprotection, [Rp]- or [SP]-diribonucleoside 3',5'-phosphorothioates I (B=adenine, cytosine, guanine, uracil) in 65–97% yield (Sierzcha-la et al., J. Org. Chem. 1996,61, 6713–6716). Attempts to improve these yields by increasing either the coupling time or DBU concentration were unsuccessful. The absolute configuration at phosphorus of the dimers (1) was assigned by treatment with the stereospecific nucleases snake venom PDE or nuclease P 1. Discrimination of [Rp]- vs [Sp]-diastereomers of the following dimer by nuclease P1 is much less profound than that observed for dideoxyribonucleoside 3',5'-phosphorothioates.

I

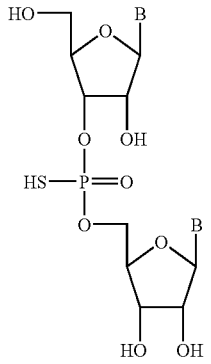

Diastereomerically pure 5'-O-DMT nucleoside 3'-O-(2-thio-1,3.2-oxathiaphospholanes) (B=T, Adebz, Cytbz) were used for the synthesis of stereo-regular phosphorothioates (Stet et al., J. Am. Chem. Soc., 1995, 117, 12019–12029). The oxathiaphospholane ring-opening condensation requires the presence of strong organic base, preferably DBU. The yield of a single coupling step is ca. 95% and resulting S-Oligos are free of nucleobase- and sugar-phosphorothioate backbone modifications. The diastereomeric purity of products was estimated on the basis of diastereoselective degradation with Nuclease P1 and a mixture of snake venom phosphodiesterase and Serratia marcescens endonuclease. Thermal dissociation studies of heteroduplexes phosphorothioates/DNA and phosphorothioates/RNA showed that their stability is stereochemical- and sequence-dependent.

I

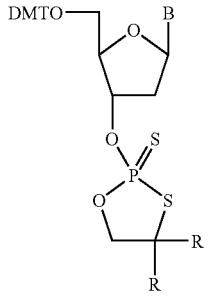

It has been previously reported that four membered cyclic sulfur compounds are kinetically and thermodynamically facile compounds to form (Eliel et al., J. Am. Chem. Soc., 1985, 107, 2946–2952). A combination of product and rate studies including Hammett LFER for k and ks for p-substituted 3-(arylthio)-3-methyl-1-Bu tosylates and the solvent and salt effects on product ratio indicate that anchimeric assistance in the solvolysis of branched 3-(alkylthio) and (3-arylthio)propyl tosylates is real and that a marked Thorpe-lngold effect is evident. This observation led us to design compounds shown in FIGS. 2 to 7 as chiral auxillaries to synthesize chiral phosphorothioates. In a similar publication the neighboring group participation of oxygen in the solvolysis of acyclic-alkoxy substituted p-toluenesulfonates was illustrated (Eliel et al., J. Org. Chem, 1985, 50, 2707–2711). Methanolysis of $PhCH_2OCRR1CR2R3CHR4OTs$ (R=Me, R1–R4=H; R=R1=Me, R2–R4=H, R=R1=R4=Me, R2=R3=H; R=R1=R3=R4=H, R2=Me; R=R1=R4=H, R2=R3=Me; $Ts=O_2SC_6H_4Me-p$) proceeds with partial rearrangement. implying neighboring-group participation, only when there are geminal Me groups in the 2- or 3-position (R2=R3=Me or R=R 1=Me).

In a recent review article entitled "New gem- and vic-disubstituent effects on cyclizations". (Jung, Michael E., Synlett, 1999, 843–846 a summary of several new gem-disubstituent effects on cyclisations are illustrated, e.g., the gem-dialkoxy, -dicarboalkoxy, and -dithioalkoxy effects, have been discovered. In addition they have also observed a new vicinal disubstituent effect. A novel ring size effect of ketals on radical cyclizations has been investigated. In a similar article by the same author it was disclosed that while reaction of the bromoalkene with a 5-membered ketal I (R=Br, n=1) with tributyltin hydride gave only the acyclic product I (R=H, n=1), reaction of the corresponding bromoalkene with a 6-membered ketal I (R=Br, N=2) gave good yields of the cyclobutane II, in a novel ketal ring size effect. Also the gem-dicarboalkoxy effect was operative in these systems, e.g., cyclization of the bromo alkene triester, (E)-$MeO_2CCH{:}CHCH_2C(CO_2Et)2CH_2OC(:S)OPh$, afforded reasonable yields of the cyclobutane III.

I

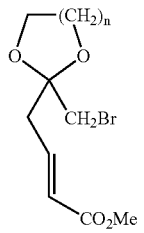

II

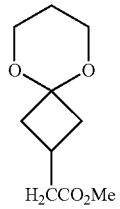

III

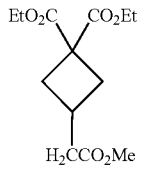

In accordance with this theory, the structures 3, 8, 14, 18, 20, and 25 all have geminal disubstituents. Use of this concept to synthesize chiral phosphorothioates with the concurrent formation of 4-membered cyclic thio compounds is novel.

Oligonucleotides that have chiral Sp phosphorothioate internucleotide linkages at the 3'-terminus are disclosed in International Application WO 99/05160, published by the PCT Feb. 4, 1999.

SUMMARY OF THE INVENTION

The present invention provides nuclease resistant phosphorothioate oligonucleotides which are useful for therapeutics, diagnostics and as research reagents. In preferred embodiments, the invention provides oligomeric compounds comprising a plurality of covalently-bound nucleosides, which have the formula:

$$5\text{-}T_1\text{—}(Nu\text{—}Sp)_n\text{—}(Nu\text{—}Lp)_m\text{—}(NU\text{—}Sp)_p Nu\text{—}T_2\text{-}3'$$

wherein:

$T_1$ and $T_2$ are each, independently, hydroxyl, a protected hydroxyl, a covalent attachment to a solid support, a nucleoside, an oligonueleoside, a nucleotide, an oligonucleotide, a conjugate group or a 5' or 3' substituent group;

each Sp is a chiral Sp phosphorothioate internucleoside linkage;

each Lp is, independently, a chiral Rp phosphorothioate internucleoside linkage, a racemic phosphorothioate internucleoside linkage or an internucleoside linkage other than a chiral phosphorothioate internucleoside linkage.;

each n and m is, independently, from 1 to 100;

each p is from 0 to 100, where the sum of n, m and 1) is from 3 to about 200;

each $N_u$ independently, has the formula:

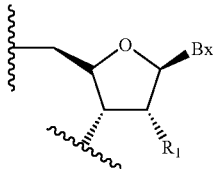

wherein:

Bx is a heterocyclic base moiety; and $R_1$ is H, hydroxyl, a protected hydroxyl, a 2'-substituent group or a protected 2'-substituent group.

In some preferred embodiments, each $R_1$ is H or hydroxyl. In further preferred embodiments. $R_1$ is $C_1$–$C_{10}$ O-alkyl or $C_1$–$C_{10}$ substituted O-alkyl, with 2'-O-methoxyethyl or 2'-O-methyl being moire preferred.

In some preferred embodiments, each Nu is, independently, adenosine, guanosine, uridine, 5-methyluridine, cytidine, 5-methylcytidine or thymine.

In some more preferred embodiments, p is 1 or 2. In further more preferred embodiments, n and p are each 1 and m is from 3 to about 20.

In some preferred embodiments, $T_1$ and $T_2$ are, independently, hydroxyl or a protected hydroxyl. In further preferred embodiments, each Lp is an Rp phosphorothioate internucleoside linkage. In still further preferred embodiments, at least one Lp is a racemic phosphorothioate internucleoside linkage. In still further preferred embodiments, at least one Lp is an internucleoside linkage other than a chiral phosphorothioate internucleoside linkage.

In some preferred embodiments, $R_1$ is a 2'-substituent group or a protected 2'-substituent group other than H, hydroxyl or a protected hydroxyl.

The present invention also provides compounds having the formula:

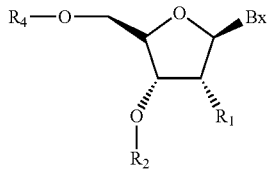

wherein:

Bx is a heterocyclic base moiety;

$R_4$ is a hydroxyl protecting group;

$R_1$ is H, hydroxyl, a protected hydroxyl, a 2'-substituent group or a protected 2'-substituent group; and $R_2$ is an Sp chiral auxiliary group.

In some preferred embodiments, the chiral auxiliary group has one of formulas I, II, III, IV, V or VI:

I

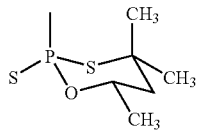

II

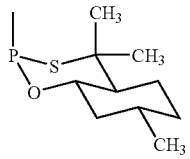

III

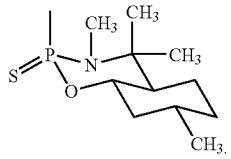

IV

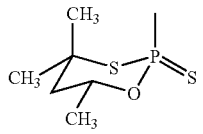

V

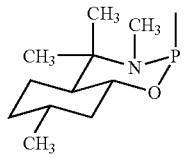

VI

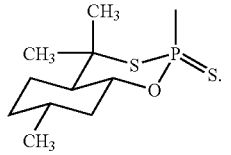

In further preferred embodiments, Bx is adenosine, guanosine, uridine, 5-methyluridine, cytidine, 5-methylcytidine or thymine.

In further preferred embodiments, each $R_1$ is H or hydroxyl. In still further preferred embodiments, $R_1$ is $C_1$–$C_{10}$ O-alkyl or $C_1$–$C_{10}$ substituted O-alkyl, with 2'-O-methoxyethyl or 2'-O-methyl being more preferred.

In some preferred embodiments, at least one $R_1$ is 2'-O-methoxyethyl or 2'-O-methyl. In further preferred embodiments. R1 is a 2'-substituent group or a protected 2'-substituent group other than H, hydroxyl or a protected hydroxyl.

The present invention also provides pharmaceutical compositions comprising one or more compounds of the invention, and an acceptable pharmaceutical carrier.

The present invention also provides methods for preparing an oligomeric compound of formula:

$$5'\text{-}T_1\text{—}(Nu\text{—}Sp)_n\text{—}(Nu\text{—}Lp)_m\text{—}(NU\text{—}Sp)_p\text{—}Nu\text{—}T\text{-}0\text{-}2\text{-}3'$$

wherein:

each $T_1$ and $T_2$ is, independently, hydroxyl, a protected hydroxyl, a covalent attachment to a solid support, a nucleoside, an oligonucleotide, a nucleotide or an oligonucleotide, a conjugate group or a 5' or 3' substituent group;

each Sp is an Sp phosphorothioate internucleoside linkage;

each Lp is, independently, an Rp phosphorothioate internucleoside linkage, a racemic phosphorothioate internucleoside linkage or an internucleoside linkage other than a chiral phosphorothioate internucleoside linkage;

each n and m is, independently, from 1 to 100;

each p is from 0 to 100 where the sum of n, m and p is from 3 to about 200;

each $N_u$ independently, has the formula:

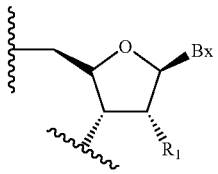

wherein:

Bx is a heterocyclic base moiety; and $R_1$ is H, hydroxyl, a protected hydroxyl, a 2'-substituent group or a protected 2'-substituent group;

comprising the steps of:

(a) providing a compound of formula:

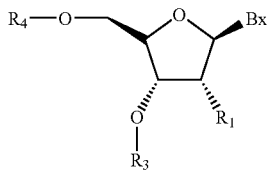

wherein:

$R_4$ is a labile hydroxyl protecting group;

$R_3$ is a covalent attachment to a solid support;

(b) deblocking said labile hydroxyl protecting group to form a deblocked hydroxyl group;

(c) optionally treating said deblocked hydroxyl group with a further compound having the formula:

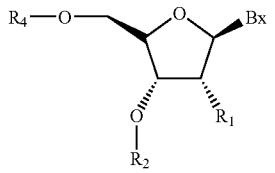

wherein:

$R_2$ is an Sp chiral auxiliary group;

and a condensing reagent to form an extended compound:

(d) optionally repeating steps (b) and (c);

(e) treating said deblocked hydroxyl group with a compound having the formula:

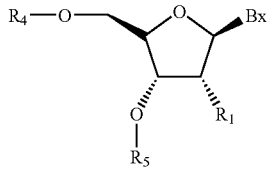

wherein:

$R_5$ is an Rp chiral auxiliary group or an activated phosphorus group;

and a condensing reagent to form a further extended compound;

(f) optionally repeating steps (e) and (f) to add further nucleosides;

(g) deblocking said labile hydroxyl protecting group to form a deblocked hydroxyl group;

(h) treating said deblocked hydroxyl group with a further compound having the formula:

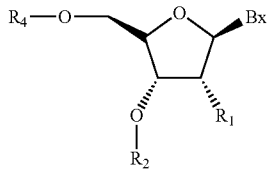

wherein:

$R_2$ is an Sp chiral auxiliary group;

and a condensing reagent to form a protected oligomeric compound; and (i) optionally repeating steps (h) and (i) to add at additional nucleosides thereby forming a further protected oligomeric compound.

Preferably, the method further comprises the step of deblocking the product of step (i).

In some preferred embodiments of the methods of the invention, the Sp chiral auxiliary group has one of formulas I, II or III:

I

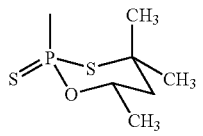

-continued

II

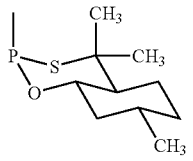

III

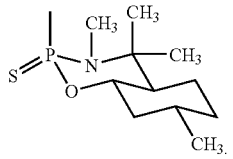

or one of formulas IV, V or VI:

IV

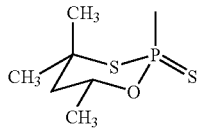

V

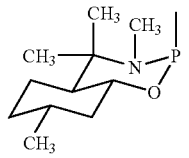

VI

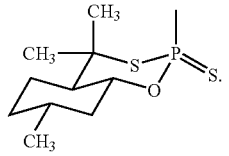

More preferred embodiments of the methods of the invention, further comprise one or more capping steps, which include treatment with a capping agent. Preferably, such capping steps are performed after a coupling step, e.g., one or more of steps c, d, e, f, h, and/or i.

In some preferred embodiments, the methods of the invention further comprising one or more oxidation steps: said oxidation steps comprising treatment with an oxidizing agent. In some preferred embodiments, such oxidiation steps are performed after a coupling step, e.g., one or more of steps c, d, e, f, h, and/or i.

In some preferred embodiments of the methods of the invention, said labile hydroxyl protecting group is dimethoxytrityl, monomethoxy trityl, trityl or 9-phenylxanthene. In further preferred embodiments of the methods of the invention, said heterocyclic base moiety is a purine or a pyrimidine, which is preferably, independently, adenosine, guanosine, uridine, 5-methyluridine, cytidine, 5-methylcytidine or thymine.

In some preferred embodiments of the compounds and methods of the invention, the sum of n, m, and p is from 5 to about 50, with 8 to about 30 being more preferred, and with 10 to about 25 being even more preferred In further preferred embodiments of the methods of the invention, $T_1$ and $T_2$ are, independently hydroxyl or a protected hydroxyl.

In still further preferred embodiments of the methods of the invention, each Lp is a racemic phosphorothioate internucleoside linkage.

In still further preferred embodiments of the methods of the invention, at least one Lp is a racemic phosphorothioate internucleoside linkage.

In some more preferred embodiments, of the methods of the invention, n and p are each 1 and m is from 3 to about 20. In further more preferred embodiments n and p are each 2 and m is from 3 to about 20.

In further preferred embodiments, p is 0.

In some preferred embodiments, at least one R, is a 2'-substituent group or a protected 2'-substituent group other than H, hydroxyl or a protected hydroxyl.

In further preferred embodiments, the activated phosphorus group is a phosphoramidite, an H-phosphonate or a phosphate triester.

In still further preferred embodiments, the covalent attachment to a solid support is a sarcosinyl-succinonyl linker.

In further preferred embodiments, compounds are provided having the formula:

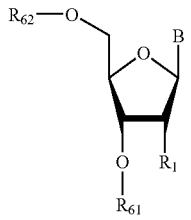

wherein:

$R_{62}$ is H or a hydroxyl protecting group;

$R_1$ is H, hydroxyl, a protected hydroxyl, a 2'-substituent group or a protected 2'-substituent group;

B is a heterocyclic base moiety; and $R_{62}$ is a chiral auxiliary selected from formulas I–V:

I

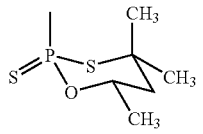

II

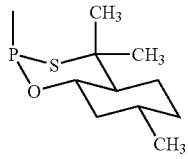

III

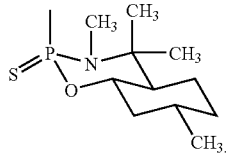

IV

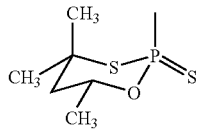

-continued

V

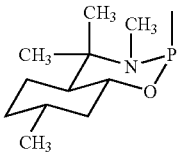

VI

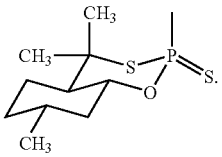

Also provided in accordance with the invention are compounds having the formula:

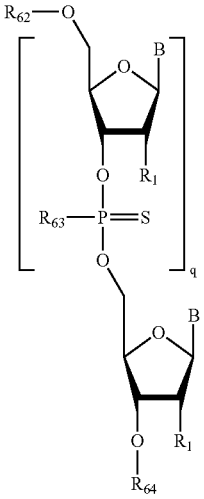

wherein:

q is 0 to about 50;

$R_{62}$ is H or a hydroxyl protecting group;

$R_1$ is H, hydroxyl, a protected hydroxyl, a 2'-substituent group or a protected 2'-substituent group;

$R_{64}$ is H, a hydroxyl protecting group, or a linker to a solid support;

$R_{63}$ is a radical selected from the group consisting of

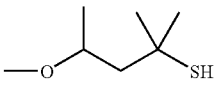

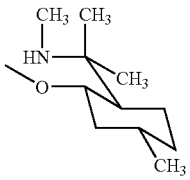

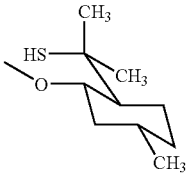

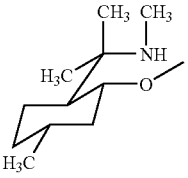

and

-continued

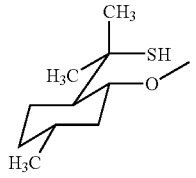

In some preferred embodiments, each $R_1$ is H or hydroxyl. In further preferred embodiments, $R_1$ is $C_1$–$C_{10}$ O-alkyl or $C_1$–$C_{10}$ substituted O-alkyl, with 2'-O-methyl being preferred.

In some preferred embodiments. B is independently, adenine, guanidine, uridine, 5-methyluridine, cytidine, 5-methylcytidine or thymine.

In further preferred embodiments, q is 5 to about 50, with 8 to about 30 being preferred, and 10 to about 25 being more preferred. In some particularly preferred embodiments, q is 0 or 1.

Also provided by the present invention are methods of modulating the production or activity of a protein in an organism, comprising contacting said organism with a compound of the invention, and methods of treating an organism having a disease characterized by the undesired production of a protein, comprising contacting said organism with a compound of the invention.

The present invention further provides methods of assaying a nucleic acid, comprising contacting a solution suspected to contain said nucleic acid with a compound of the invention.

DETAILED DESCRIPTION OF THE INVENTION

Figure 1:
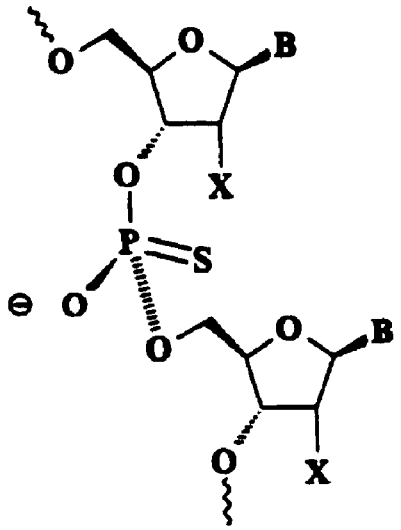
FIG. 1 shows the structure of an Rp and an Sp chiral phosphorothioate internucleotide linkage.
Figure 1:
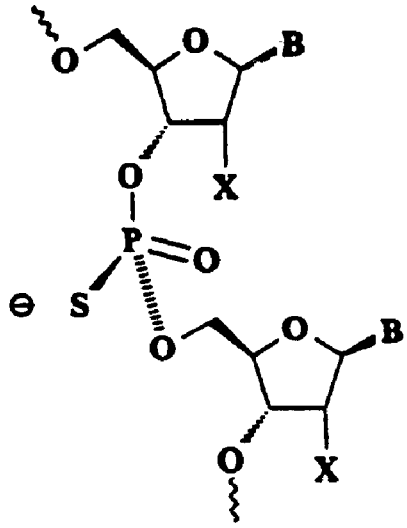
Figure 2:
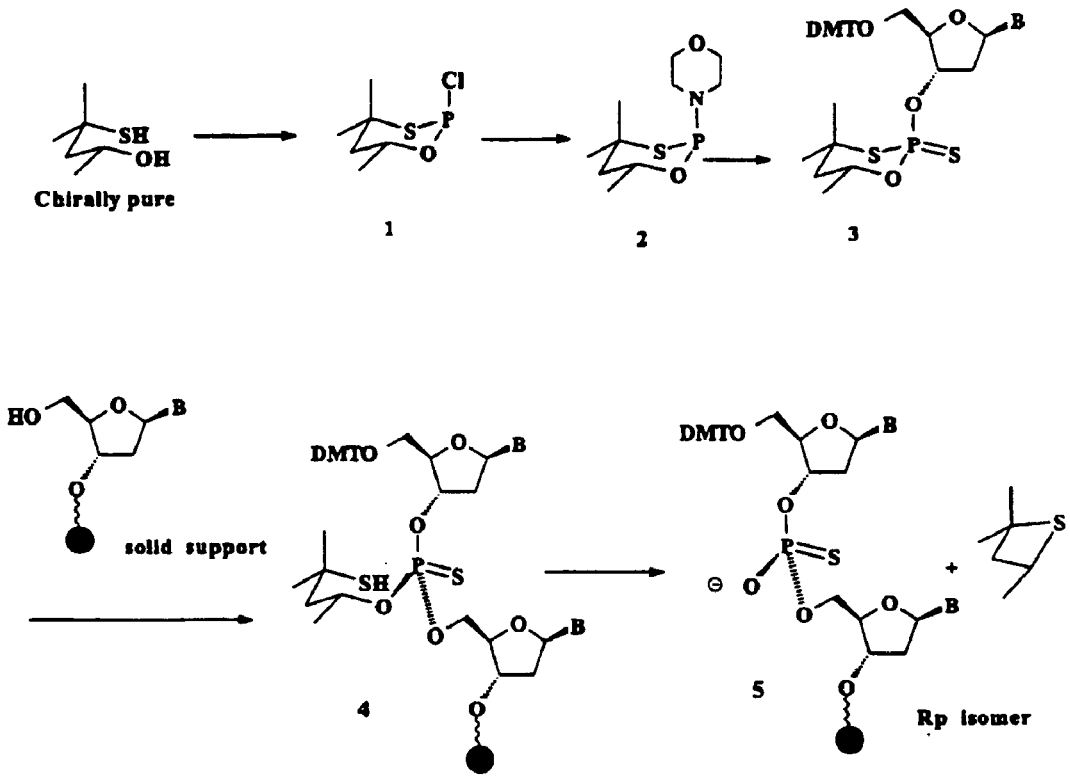
FIG. 2 shows the chiral adjuvant (R)-4-mercapto-4-methyl-2-pentanol and the chiral building block derived therefrom which leads to Rp chiral phosphorothioate internucleotide linkages.
Figure 3:
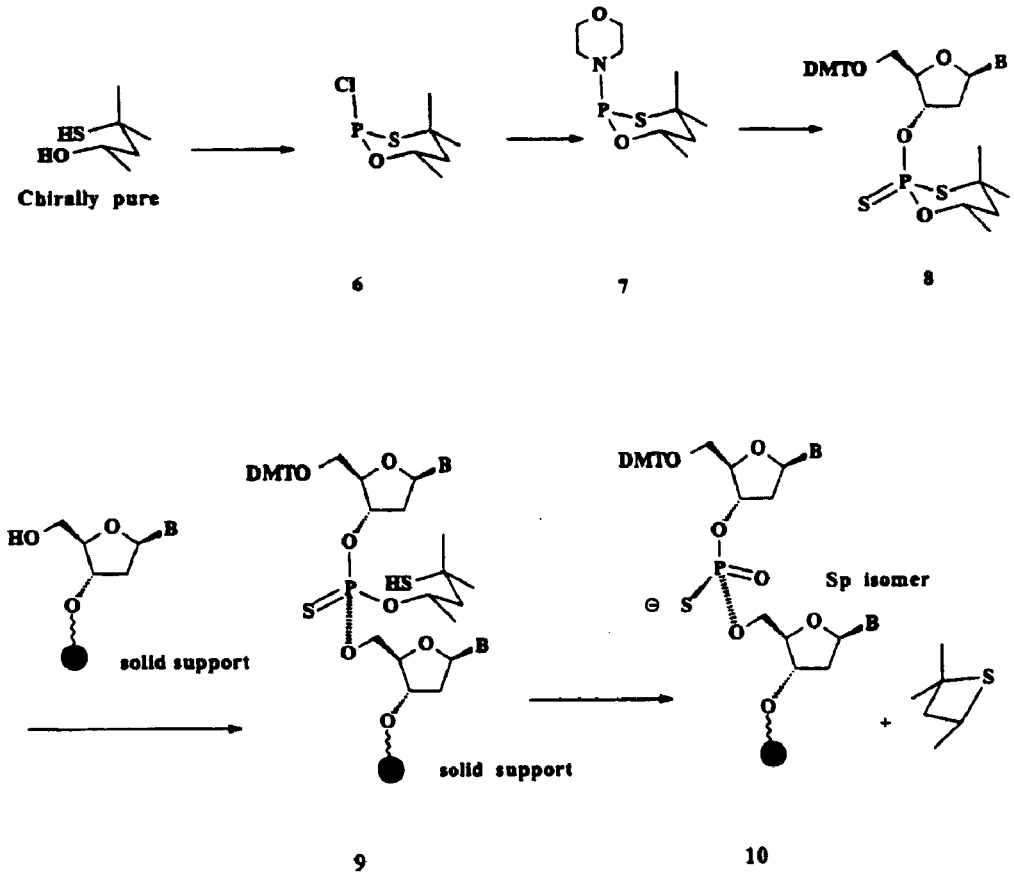
FIG. 3 shows the chiral adjuvant (S)-4-mercapto-4-methyl-2-pentanol and the chiral building block derived therefrom which leads to Sp chiral phosphorothioate internucleotide linkages.
Figure 4:
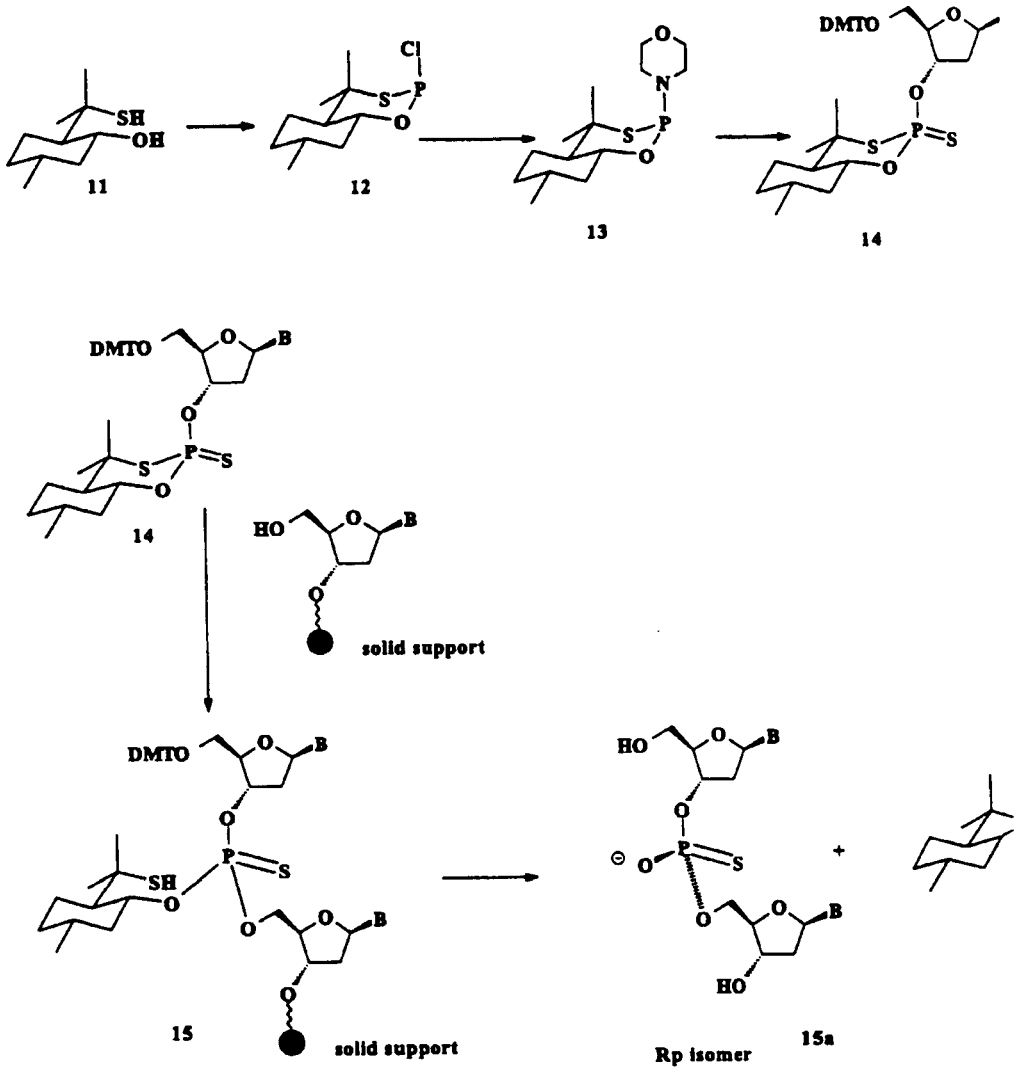
FIG. 4 shows (+)-5-methyl-2-(1-methyl-1-thioethyl) cyclohexanol, which is obtained from (+)-pulegone, and the chiral building block derived therefrom which leads to Rp chiral phosphorothioate internucleotide linkages.
Figure 5:
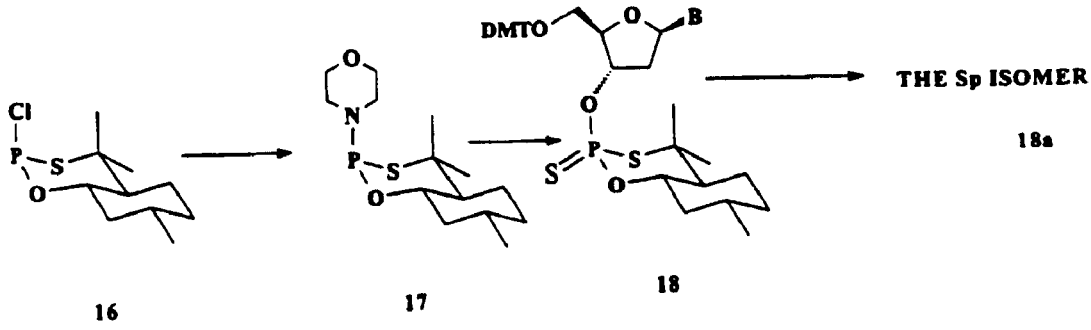
FIG. 5 shows (−)-5-methyl-2-(1-methyl-1-thioethyl) cyclohexanol, which is obtained from (−)-pulegone, and the chiral building block derive therefrom which leads to Sp chiral phosphorothioate internucleotide linkages.
Figure 6:
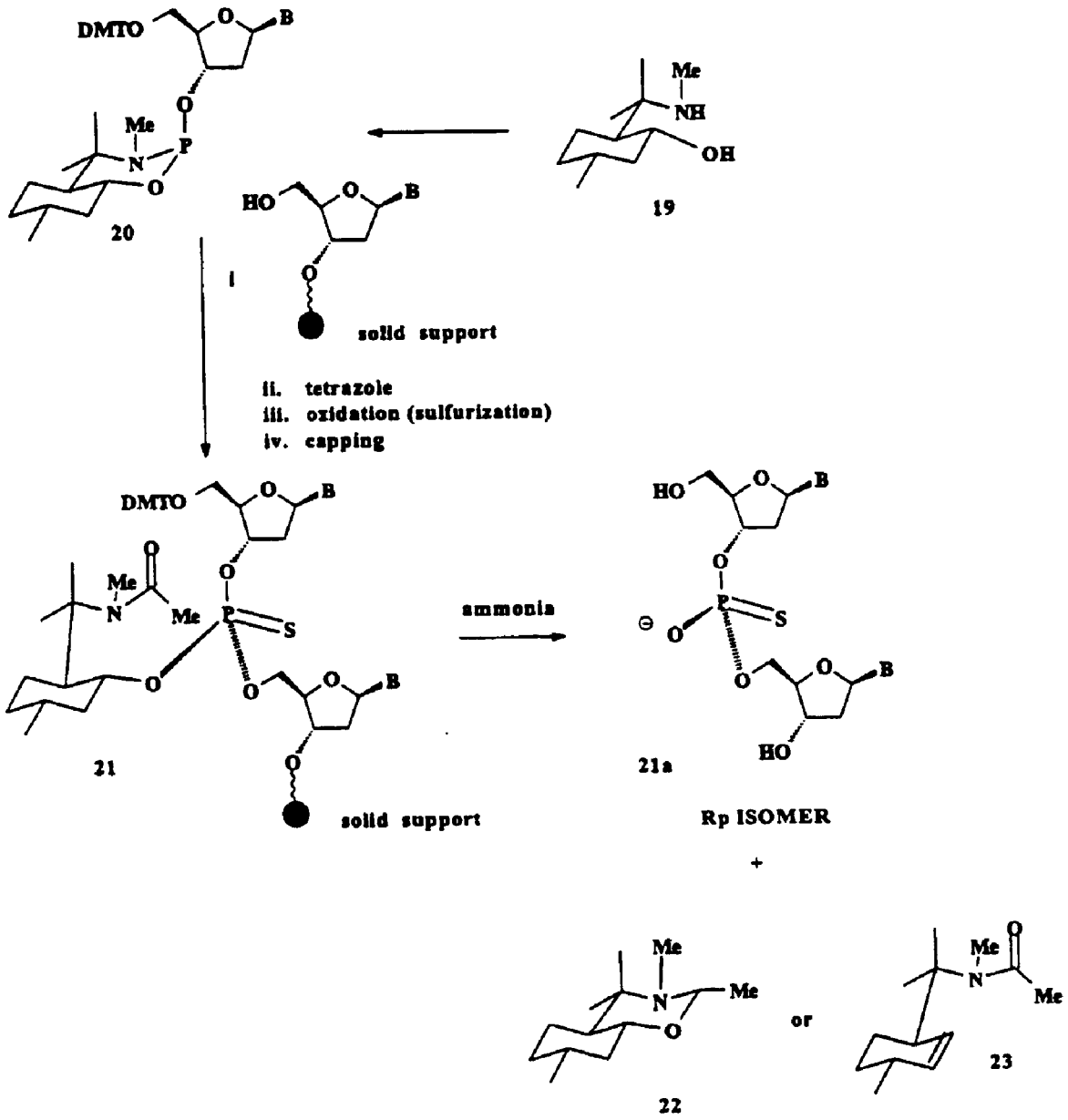
FIG. 6 shows 5C-methyl-2t-[(1-methyl-1-benzylamino) ethyl]-cyclohexan-1t-ol which is obtained from (+)-pulegone, and the chiral building block derived therefrom which leads to Rp chiral phosphorothioate internucleoside linkages.
Figure 7:
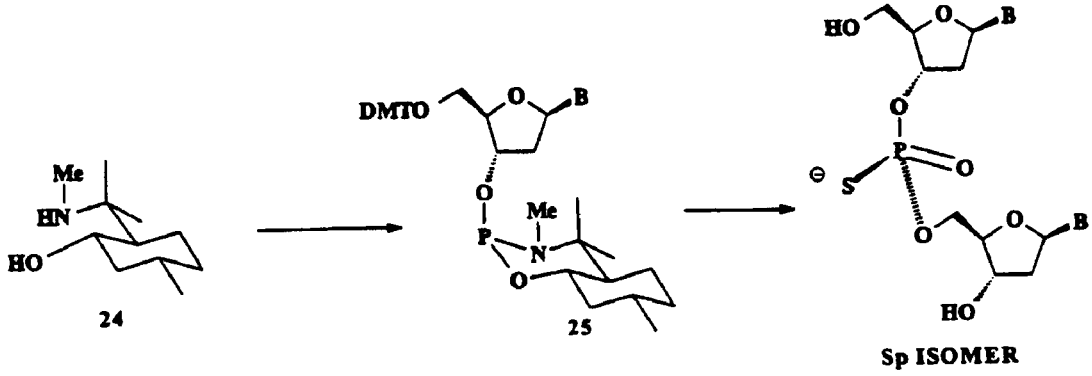
FIG. 7 shows 5C-methyl-2t-[(1-methyl-1-benzylamino) ethyl]-cyclohexan-1t-ol which is obtained from (−)-pulegone, and the chiral building block derive therefrom which leads to Sp chiral phosphorothioate internucleotide linkages.

The present invention provides oligomeric compounds having a first 5'-region that has at least one chiral Sp internucleoside linkage, and a second region that has chiral Rp internucleoside linkages, racemic phosphorothioate internucleoside linkages or internucleoside linkages other than chiral or racemic phosphorothioate internucleoside linkages. The present invention further provides oligomeric compounds having 3 regions where the first and second are as described above, and the third region has one or more Sp phosphorothioate internucleoside linkages. Also provided in accordance with the present invention are methods for the preparation of such oligomeric compounds having 2 or 3 regions. The presence of Sp geometry at the 5'-end of the oligomeric compound (2 regions) or at the wings of the oligomeric compound (e.g. at the 3' and 5' ends of 3-region compounds) reduces the susceptibility of the compound to exonuclease degradation. The presence of Rp geometry in the second region increases the affinity of the compound to complementary nucleic acid.

In one aspect of the invention chimeric compounds are prepared having Rp and Sp internucleoside linkages of high chiral purity (i.e., "chiral Sp". "chiral Rp" "Sp" or "Rp" linkages). High chiral purity as used here is meant to indicate a percentage of the indicated enantiomer of 90% or greater. The preparation of timers and oligomers having Sp internucleoside linkages is described in U.S. Pat. Nos. 5,212,295, 5,587,361 and 5,599,797, the contents of which are incorporated herein by reference.

As will be recognized, this invention concerns oligonucleotides that exhibit increased stability relative to their naturally occurring counterparts. Extracellular and intracellular nucleases generally do not recognize (and, therefore, do not bind to) the compounds of the invention.

The present invention further includes methods of preparing oligomeric compounds having at least one Sp internucleoside linkage at the 5' and at the 3' ends. In preferred embodiments the oligomeric compounds have one or more Sp internucleoside linkages at the 5' and at the 3' ends and the internal internucleoside linkages are all Rp phosphorothioate linkages. Such oligomeric compounds are prepared by treating a solid support bound monomer with monomers having reactive phosphorus moieties that give defined stereochemistry at the resultant internucleoside linkages. The first monomer or monomers are selected to give Sp internucleotide linkages. The next section is prepared to have Rp or racemic internucleoside link-ages with the final section prepared as the first section to one or more Sp internucleoside linkages. The monomers are prepared as illustrated in the examples below.

Gem dialkyl substitutents located in selected chiral auxiliary groups favor product formation with the release of 4-membered oxathiane, 6-membered oxazine or amide structures. These compounds can be conveniently synthesized from (+)-pulegone and (−)-pulegone ((R)-4-mercapto-4-methyl-2-pentanol and (S)-4-mercapto-4-methyl-2-pentanol).

In some preferred embodiments, methods are provided for preparing an oligomeric compound of formula:

$$5'\text{-}T_1\text{—(Nu Sp)}_n\text{—(Nu—Lp)}_m\text{—(Nu-Sp)}_p\text{— Nu—}T_2\text{-}3'$$

wherein:

each $T_1$ and $T_2$ is, independently, hydroxyl, a protected hydroxyl, a covalent attachment to a solid support, a nucleoside, an oligonucleotide, a nucleotide or an oligonucleotide, a conjugate group or a 5' or 3' substituent group;

each Sp is an Sp phosphorothioate internucleoside linkage;

each Lp is, independently, an Rp phosphorothioate internucleoside linkage, a racemic phosphorothioate internucleoside linkage or an internucleoside linkage other than a chiral phosphorothioate internucleoside linkage;

each n and m is, independently, from 1 to 100;

each p is from 0 to 100 where the sum of n, m and p is from 3 to about 200;

each $N_u$, independently, has the formula:

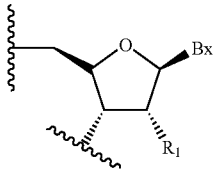

wherein:

Bx is a heterocyclic base moiety; and $R_1$ is H, hydroxyl, a protected hydroxyl, a 2'-substituent group or a protected 2'-substituent group;

comprising the steps of:

(a) providing a compound of formula:

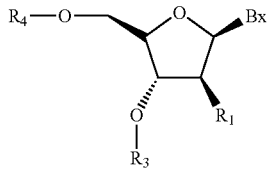

wherein:

$R_4$ is a labile hydroxyl protecting group;

$R_3$ is a covalent attachment to a solid support;

(b) deblocking said labile hydroxyl protecting group to form a deblocked hydroxyl group;

(c) optionally treating said deblocked hydroxyl group with a further compound having the formula:

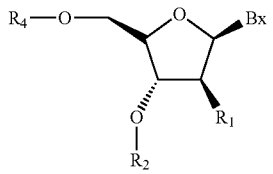

wherein:

$R_4$ is an Sp chiral auxiliary group;

and a condensing reagent to form an extended compound;

(d) optionally repeating steps (b) and (c);

(e) treating said deblocked hydroxyl group with a compound having the formula:

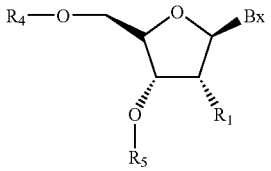

wherein:

$R_5$ is an Rp chiral auxiliary group or an activated phosphorus group;

and a condensing reagent to form a further extended compound;

(f) optionally repeating steps (e) and (f) to add further nucleosides;

(g) deblocking said labile hydroxyl protecting group to form a deblocked hydroxyl group;

(h) treating said deblocked hydroxyl group with a further compound having the formula:

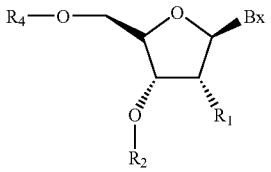

wherein:

$R_2$ is an Sp chiral auxiliary group;

and a condensing reagent to form a protected oligomeric compound; and (i) optionally repeating steps (h) and (i) to add at additional nucleosides thereby forming a further protected oligomeric compound.

In the methods of the invention, the coupling of nucleosidic monomeric units is preceded by deblocking (of the 5'-terminal hydroxyl (i.e., removal of the 5'-protecting group) of the growing chain. Such "deblocking" cut be accomplished using a variety reagents known to those in the art. One suitable reagent is a dichloromethane solution of 2% dichloroacetic acid (v/v), or toluene solution of 3% dichloroacetic acid (v/v).

It is preferred that the present invention include one or more capping steps in between couplings of successive nucleosidic monomers. The capping step can be performed either prior to or after an oxidation step, and are preferably performed after a coupling step, e.g., one or more of steps c, d, e, f, h, and/or i. Such a capping step is generally known to be beneficial by preventing shortened oligomer chains, by blocking chains that have not reacted in the coupling cycle. One representative capping reagent used for capping is acetic anhydride. Other suitable capping reagents and methodologies can be found in U.S. Pat. No. 4,816,571, issued Mar. 28, 1989, hereby incorporated by reference in its entirety.

In some preferred embodiments, the methods of the invention further comprising one or more oxidation steps; said oxidation steps comprising treatment with an oxidizing agent. Choice of oxidizing agent will determine whether the resulting linkage will be, for example, a phosphodiester, phosphorothioate, or phosphorodithioate linkage. In some preferred embodiments, oxidizing steps are performed after a coupling step, e.g., one or more of steps c, d, e, f, h, and/or i.

Oxidizing agents used to produce phosphorothioate: and/or phosphorodithioate linkages (also known as "sulfurizing reagents") include Beaucage reagent (see e.g. Iyer, R. P., et. al., J. Chem. Soc., 1990, 112, 1253–1254, and Iyer, R. P., et. al., J. Org. Chem., 1990, 55, 4693–4699); tetraethylthiuram disulfide (see e.g., Vu, H., Hirschbein, B. L., Tetrahedron Lett., 1991, 32, 3005–3008); dibenzoyl tetrasulfide (see e.g., Rao, M. V., et.al., Tetrahedron Lett., 1992, 33, 4839–4842); di(phenylacetyl)disulfide (see e.g., Kamer, P. C. J., Tetrahedron Lett., 1989, 30, 6757–6760), Bis(O,O-diisopropoxy phosphinothioyl)disulfide (see Stec et al., Tetrahedron Lett., 1993, 34, 5317–5320); 3-ethoxy-1,2,4-dithiazoline-5-one (see Nucleic Acids Research, 1996 24, 1602–1607, and Nucleic Acids Research, 1996 24, 3643–3644); Bis(p-chlorobenzenesulfonyl)disulfide (see NucleicAcids Research, 1995 23,4029–4033); sulfur, sulfur in combination with ligands like triaryl, trialkyl, triaralkyl, or trialkaryl phosphines. The foregoing references are hereby incorporated by reference in their entirety.

Useful oxidizing agents used to form the phosphodiester or phosphorothioate linkages include iodine/tetrahydrofuran/water/pyridine or hydrogen peroxide/water or tert-butyl hydroperoxide or any peracid like m-chloroperbenzoic acid. In the case of sulfurization the reaction is performed under anhydrous conditions with the exclusion of air, in particular oxygen whereas in the case of oxidation the reaction can be performed under aqueous conditions.

Solid supports are substrates which are capable of serving as the solid phase in solid phase synthetic methodologies, such as those described in Caruthers U.S. Pat. Nos. 4,415,732; 4,458,066; 4,500,707; 4,668,777;

4,973,679, and 5,132,418: and Koster U.S. Pat. Nos. 4,725,677 and Re. 34,069. Linkers are known in the art as short molecules which serve to connect a solid support to functional groups (e.g., hydroxyl groups) of initial synthon molecules in solid phase synthetic techniques. Suitable linkers are disclosed in, for example, Oligonucleotides And Analogues A Practical Approach, Ekstein, F. Ed., IRL Press, N.Y. 1991. Chapter 1, pages 1–23.

Solid supports according to the invention include those generally known in the art to be suitable for use in solid phase methodologies, including, for example, controlled pore glass (CPG), oxalyl-controlled pore glass (see, e.g., Alul, et al., Nucleic Acids Research 1991, 19, 1527, hereby incorporated by reference in its entirety). TentaGel Support—an aminopolyethyleneglycol derivatized support (see, e.g., Wright, et al., Tetrahedron Letters 1993, 34, 3373, hereby incorporated by reference in its entirety) and Poros—a copolymer of polystyrene/divinylbenzene.

In some preferred embodiments of the methods of the invention, the Sp chiral auxiliary group has one of formulas I, II or III:

I

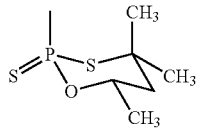

II

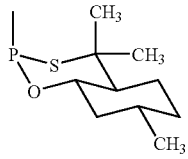

-continued

III

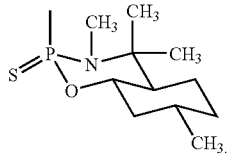

or one of formulas IV, V or VI:

IV

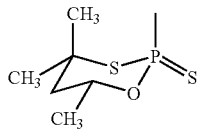

V

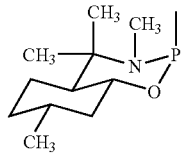

VI

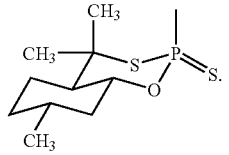

Upon completion of addition of monomeric synthons, the completed oligomer is cleaved from the solid support. The cleavage step, which can precede or follow deprotection of protected functional groups, will in preferred embodiments yield a compound devoid of protecting groups, and chiral auxiliaries. Suitable cleavage reagents include those that are known in the an such as, for example, $NH_4OH$ (2890) at 50° C. for 2 hours.

Oligonucleotides according to the present invention that are hybridizable to a target nucleic acid preferably comprise from about 5 to about 50 nucleosides. It is more preferred that such compounds comprise from about 8 to about nucleosides, with 10 to about 25 nucleosides being particularly preferred. As used herein, a target nucleic acid is any nucleic acid that can hybridize with a complementary nucleic acid-like compound. Further in the context of this invention, "hybridization" shall mean hydrogen bonding, which may be Watson-Crick. Hoogsteen or reversed Hoogsteen hydrogen bonding between complementary nucleobases. "Complementary" as used herein, refers to the capacity for precise pairing between two nucleobases. For example, adenine and thymine are complementary nucleobases which pair through the formation of hydrogen bonds. "Complementary" and "specifically hybridizable," as used herein, refer to precise pairing or sequence complementarity between a first and a second nucleic acid-like oligomers containing nucleoside subunits. For example, if a nucleobase at a certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases which can hydrogen bond with each other.

Thus, "specifically hybridizable" and "complementary" are terms which are used to indicate a sufficient degree of complementarity such that stable and specific binding occurs between a compound of the invention and a target RNA molecule. It is understood that an oligomeric compound of the invention need not be 100% complementary to its target RNA sequence to be specifically hybridizable. An oligomeric compound is specifically hybridizable when binding of the oligomeric compound to the target RNA molecule interferes with the normal function of the target RNA to cause a loss of utility, and there is a sufficient degree of complementarity to avoid non-specific binding of the oligomeric compound to non-target sequences under conditions in which specific binding is desired, i.e. under physiological conditions in the case of in vivo assays or therapeutic treatment, or in the case of in vitro assays, under conditions in which the assays are performed.

As used herein the term "chiral auxiliary" is meant to include groups that function as a protecting groups for phosphorus linkages during the course of the synthesis of oligomeric phosphorothioates. Chiral auxiliaries will give either Sp or Rp chirality for the respective internucleoside linkage in the final oligomeric compound. Accordingly, chiral auxiliaries are allowed to remain on the growing chain, and are removed at the end of the iterative synthetic regime. Removal of chiral auxiliaries can be conveniently accomplished in a single treatment after the completion of the iterative synthesis. Preferred chiral auxiliaries are shown as used to prepare monomers of the invention in the figures (see compounds 3, 8, 14, 18, 20 and 25).

Representative heterocyclic base moieties useful in the compounds and methods described herein include adenine, guanine, cytosine, uridine, and thymine, as well as other non-naturally occurring and natural nucleobases such as xanthine, hypoxanthine. 2-aminoadenine, 6-methyl and other alkyl derivatives of adenine and guanine, 2-propyl and other alkyl derivatives of adenine and guanine. 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in Antisense Research and Application, Ed. S. T. Crooke and B. Lebleu. CRC Press, 1993, in Englisch et al., Angewandte Chemie, International Edition, 1991, 30, 613–722 (see especially pages 622 and 623, and in the Concise Encyclopedia of Polymer Science and Engineering, J. I. Kroschwitz Ed., John Wiley & Sons, 1990, pages 858–859, Cook, Anti-Cancer Drug Design 1991, 6, 585–607, each of which are hereby incorporated by reference in their entirety). The term "nucleosidic base" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole.

Preferred heterocyclic base moieties include adenine, $N^6$-benzoyladenine, cytosine, $N^4$-benzoylcytosine, 5-methylcytosine, $N^4$-benzoyl-5-methylcytosine, thymine, uracil, guanine. $N^2$-isobutyrylguanine and 2-aminoadenine.

Further naturally- and non-naturally-occurring heterocyclic base moieties include those disclosed in U.S. Pat. No. 3,687,808 (Merigan et al.), in chapter 15 by Sanghvi, in Antisense Research and Application, Ed. S. T. Crooke and B. Lebleu, CRC Press, 1993, in Englisch et al., Angewandte Chemie, International Edition, 1991, 30, 613–722 (see, especially pages 622 and 623, and in the Concise Encyclopedia of Polymer Science and Engineering, J. I. Kroschwitz, Ed., John Wiley & Sons, 1990, pages 858–859, Cook, P. D., Anti-Cancer Drug Design, 1991, 6, 585–607, each of which is hereby incorporated by reference in its entirety. The term "heterocyclic base moiety" is further intended to include heterocyclic ring systems that can serve as nucleosidic bases including certain 'universal bases' that are not nucleosidic bases in the most classical sense but serve as nucleosidic bases. Especially mentioned as a universal base is 3-nitropyrrole.

In general, the term "hetero" denotes an atom other than carbon, preferably but not exclusively N, O, or S. Accordingly, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

As used herein, the terms "2'-substituent group" or "5' or 3' substituent group" includes groups attached to the 2'-position of the ribofuranosyl moiety with or without an oxygen atom. Sugar substituent groups amenable to the present invention include, but are not limited to, fluoro. O-alkyl, O-alkylamino, O-alkylalkoxy, protected O-alkylamino, O-alkylaminoalkyl, 6-alkyl imidazole and polyethers of the formula $(O\text{-alkyl})_m$, wherein m is 1 to about 10. Preferred among these polyethers are linear and cyclic polyethylene glycols (PEGS), and (PEG)-containing groups, such as crown ethers and those which are disclosed by Ouchi et al., Drug Design and Discovery 1992, 9, 93; Ravasio et al., J. Org. Chem, 1991, 56, 4329; and Delgardo et, al., Critical Reviews in Therapeutic Drug Carrier Systems 1992, 9, 249, each of which is hereby incorporated by reference in its entirety. Further sugar modifications are disclosed in Cook, P. D., Anti-Cancer Drug Design, 1991, 6, 585–607, Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled "Oligomeric Compounds having Pyrimidine Nucleotide(s) with 2' and 5' Substitutions," hereby incorporated by reference in its entirety.

Additional sugar substituent groups amenable to the present invention include 2'-SR and 2'-NR, groups, wherein each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons is disclosed by Hamm et al., J. Org. Chem., 1997, 62, 3415–3420, 2'-NR nucleosides are disclosed by Goettingen, M., J. Org. Chem., 1996, 61, 6273–6281; and Polushin et al., Tetrahedron Lett., 1996, 37, 3227–3230. Further representative sugar substituent groups amenable to the present invention include those having one of formula XI or XII:

$$-(Z_0-(CH_2)_{q1})_{R1}-(Q)_{R1}-E \qquad \text{XI}$$

-continued

XII

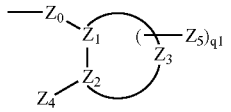

wherein:

$Z_0$ is O, S or NH;

E is $C_1$–$C_{10}$ alkyl, N ($Q_1$) (Q2) or N═C ($Q_1$) ($Q_2$)

each $Q_1$ and $Q_2$ is, independently. H, $C_1$–$C_{10}$ alkyl, substituted alkyl, dialkylaminoalkyl, a nitrogen protecting group, a tethered or untethered conjugate group, a linker to a solid support;

or $Q_1$ and $Q_2$, together, are joined in a nitrogen protecting group or a ring structure that can include at least one additional heteroatom selected from N and O;

$q^1$ is from 1 to 10:

$q^2$ is from 1 to 10;

$q^3$ is zero or 1;

$q^4$ is zero, 1 or 2;

$q^5$ is 1 to 10;

each M, is, independently, H, $C_1$–$C_8$ alkyl. $C_1$–$C_8$ haloalkyl, C(═NH)N(H)$M_2$, C(═O)N(H)$M_2$ or OC(═O)N(H)$M_2$;

$M_2$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic; and $Z_4$ is $OM_1$, $SM_1$ or N($M_1$)$_2$;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms. N ($Q_1$) ($Q_2$), $OQ_1$, halo, $SQ_1$ or CN.

Representative 2'-O-sugar substituent groups of formula XI are disclosed in U.S. Pat. No. 6,172,209 which is hereby incorporated by reference in its entirety.

Representative cyclic 2'-O-sugar substituent groups of formula XII are disclosed in U.S. patent application Ser. No. 09/123,108, filed Jul. 27, 1998, entitled "RNA Targeted 2'-Modified Oligonucleotides that are Conformationally Preorganized." hereby incorporated by reference in its entirety.

Sugars having O-substitutions on the ribosyl ring are also amenable to the present invention. Representative substitutions for ring O include, but are not limited to, S. $CH_2$, CHF. and $CF_2$, See, e.g., Secrist et al., Abstract 21. Program & Abstracts, Tenth International Roundtable, Nucleosides, Nucleotides and their Biological Applications, Park City, Utah, Sep. 16–20, 1992, hereby incorporated by reference in its entirety.

Additional modifications may also be made at other positions on the oligonucleotide, particularly the 3' position of the sugar on the 3' terminal nucleotide and the 5'-position of 5' terminal nucleotide. For example, one additional modification of the oligonucleotides of the present invention involves chemically linking to the oligonucleotide one or more moieties or conjugates which enhance the activity, cellular distribution or cellular uptake of the oligonucleotide. Such moieties include, but are not limited to, lipid moieties such as a cholesterol moiety (Letsinger et al., Proc. Natl. Acad. Sci. USA, 1989, 86, 6553), cholic acid (Manoharan et al., Bioorg. Med. Chem. Len., 1994. 4, 1053), a thioether, e.g., hexyl-5-tritylthiol (Manoharan et al., Ann. N.Y. Acad. Sci., 1992, 660. 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEES Lett., 1990, 259, 327; Svinarchuk et al., Biochimie, 1993. 75, 49), a phospholipid, e.g., di-hexadecyl-rac-glycerol or triethylammonium-1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), adamantane acetic acid (Manoharan et al., Tetrahedron Len., 1995, 36, 3651), a palmityl moiety (Mishra et al., Biochim. Biophys. Acta, 1995, 1264, 229), or an octadecylamine or hexylamino-carbonyl-oxycholesterol moiety (Crooke et al., J. Pharmacol Exp. Ther., 1996, 277, 923).

The monomers of the present invention can include appropriate activated phosphorus groups such as activated phosphate groups and activated phosphate groups. As used herein, the terms activated phosphate and activated phosphite groups refer to activated monomers or oligomers that are reactive with a hydroxyl group of another monomeric or oligomeric compound to form a phosphorus-containing internucleotide linkage. Such activated phosphorus groups contain activated phosphorus atoms in P''' or $P^V$ valency states. Such activated phosphorus atoms are known in the art and include, but are not limited to, phosphoramdite, H-phosphonate and phosphate triesters. A preferred synthetic solid phase synthesis utilizes phosphoramidites as activated phosphates. The phosphoramidites utilize P''' chemistry. The intermediate phosphite compounds are subsequently oxidized to the $P^V$ state using known methods to yield, in a preferred embodiment, phosphodiester or phosphorothioate internucleoside linkages. Additional activated phosphates and phosphites are disclosed in Tetrahedron Report Number 309 (Beaucage and Iyer. Tetrahedron, 1992, 48. 2223–2311).

Functional groups including those located on heterocyclic base moieties and 2'-sugar substituent groups are routinely blocked with protecting (blocking groups) during synthesis and subsequently deblocked. In general, a blocking group renders a chemical functionality of a molecule inert to specific reaction conditions and can later be removed from such functionality in a molecule without substantially damaging the remainder of the molecule. See, Green and Wuts, Protective Groups in Organic Synthesis, 2d edition. John Wiley & Sons, New York, 1991. For example, amino groups can be blocked with nitrogen protecting groups such as phthalimido. 9-fluorenylmethoxycarbonyl (FMOC), triphenylmethylsulfenyl, t-BOC or benzyl groups. Carboxyl groups can be protected as acetyl groups. Representative hydroxyl protecting groups are described by Beaucage et al., Tetrahedron 1992, 48, 2223. Preferred hydroxyl protecting groups are acid-labile groups, such as the trityl, monomethoxytrityl, dimethoxytrityl, trimethoxytrityl, 9-phenylxanthin-9-yl (Pixyl) and 9-(p-methoxyphenyl) xanthin-9-yl (MOX). Chemical functional groups can also be "blocked" by including them in a precursor form. That an azido group can be considered a "blocked" form of an arsine as the azido group is easily converted to the amine. Further representative protecting groups utilized in oligonucleotide synthesis are discussed in Agrawal et al., Protocols for Oligonucleotide Conjugates, Eds., Humana Press, New Jersey, 1994, Vol. 26, pp. 1–72.

The term "nucleoside" as used in connection with this invention refers to a unit made up of a heterocyclic base and its sugar. The term "nucleotide" refers to a nucleotide having a phosphate group on its 3' or 5' sugar hydroxyl group.

As used herein, the term "oligonucleotide" is intended to include both naturally occurring and non-naturally occurring (i.e., "synthetic") oligomers of linked nucleosides. Although such linkages generally are between the 3' carbon of one nucleoside and the 5' carbon of a second nucleoside (i.e., 3'–5' linkages), other linkages (such as 2'–5' linkages) can be formed.

Naturally occurring oligonucleotides are those which occur in nature; for example ribose and deoxyribose phosphodiester oligonucleotides having adenine, guanine, cytosine, thymine and uracil nucleobases. As used herein, non-naturally occurring oligonucleotides are oligonucleotides that contain modified sugar, internucleoside linkage and/or nucleobase moieties. Such oligonucleotide analogs are typically structurally distinguishable from, yet functionally interchangeable with, naturally occurring or synthetic wild type oligonucleotides. Thus, non-naturally occurring oligonucleotides include all such structures which function effectively to mimic the structure and/or function of a desired RNA or DNA strand, for example, by hybridizing to a target.

As used herein, the term "alkyl" includes, but is not limited to., straight chain, branched chain and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety. Substituent groups include, but are not limited to, alkyl, alkenyl, alkynyl, aryl, hydroxyl, alkoxy, alcohol, benzyl. phenyl, nitro, thiol, thioalkoxy, thioalkyl, trifluoromethyl, halo, nitrile, trifluoromethoxy and azido. As used herein, the term "lower alkyl" is intended to mean an alkyl group having 10 or fewer carbons.

Alkenyl groups according to the invention are to straight chain, branch chain, and cyclic hydrocarbon groups containing at least one carbon-carbon double bond, and alkynyl groups are to straight chain, branch chain, and cyclic hydrocarbon groups containing at least one carbon-carbon triply bond. Alkenyl and alkynyl groups of the present invention can be substituted.

Aryl groups are substituted and unsubstituted aromatic cyclic moieties including but not limited to phenyl, naphthyl, anthracyl, phenanthryl, pyrenyl, and xylyl groups. Alkaryl groups are those in which an aryl moiety links an alkyl moiety to a core structure, and aralkyl groups are those in which an alkyl moiety links an aryl moiety to a core structure.

As used herein, the term "oligonucleoside" includes oligomers or polymers containing two or more nucleoside subunits having a non-phosphorous linking moiety. Oligonucleosides according to the invention have a ribofuranose moiety attached to a nucleobase through a glycosyl bond. An oligonucleotide/nucleoside for the purposes of the present invention is a mixed backbone oligomer having at least two nucleosides covalently bound by a non-phosphate linkage and at least one phosphorous containing covalent bond with a nucleotide, wherein at least one of the monomeric nucleotide or nucleoside units is a 2'-O-substituted compound prepared using the process of the present invention. An oligonucleotide/nucleoside can additionally have a plurality of nucleotides and nucleosides coupled through phosphorous containing and/or non-phosphorous containing linkages.

As used herein, the term "aralkyl" denotes alkyl groups which bear aryl groups, for example, benzyl groups. The term "alkaryl" denotes aryl groups which bear alkyl groups, for example, methylphenyl groups. As used herein, the term "aryl" denotes aromatic cyclic groups including, but not limited to, phenyl, naphthyl, anthracyl, phenanthryl and pyrenyl. Preferred aryl and aralkyl groups include, but are not limited to, phenyl, benzyl, xylyl, naphthyl, toluyl, pyrenyl, anthracyl, azulyl, phenethyl, cinnamyl, benzhydryl, and mesityl. Typical substituents for substitution include, but are not limited to, hydroxyl, alkoxy, alcohol, benzyl, phenyl, nitro, thiol, thioalkoxy, halogen, or alkyl, aryl, alkenyl, or alkynyl groups.

As used herein, the term "alkanoyl" has its accustomed meaning as a group of formula —C(═O)-alkyl. A preferred alkanoyl group is the acetyl group.

Phosphorothioate oligonucleotides having chirally pure intersugar linkages which are synthesized according to methods of the present invention may be analyzed in a number of ways. For example, configuration analysis of resulting sequence specific phosphorothioate oligonucleotides having subtantially chirally pure all-Sp or all-Rp intersugar linkages may be determined by the use of [31P] NMR chemical shifts. Such chemical shifts have been used to identify the Rp epimer of a phosphorothioate di-nucleotide. See Ludwig and Eckstein. J. Org. Chem., 631–635(1989).

Methods of the present invention are useful for preparing oligomeric compounds having in addition to chiral Sp internucleoside linkages other chiral and achiral internucleoside linkages. As defined in this specification, other chiral and achiral internucleoside linkages are meant to include those that retain a phosphorus atom in the backbone and those that do not have a phosphorus atom in the backbone. For the purposes of this specification, and as sometimes referenced in the art, modified oligonucleotides that do not have phosphorus atoms in their internucleoside linkages can also be considered to be oligonucleosides.

Preferred modified oligonucleoside linkages include, for example, phosphorothioates, chiral phosphorothioates, phosphorodithioates, phosphotriesters. aminoalkylphosphotriesters, methyl and other alkyl phosphonates including 3'-alkylene phosphonates and chiral phosphonates, phosphonates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that each the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131: 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application, and each of which is herein incorporated by reference.

Preferred modified oligonucleoside linkages that do not include a phosphorus atom therein include alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH, component parts.

Representative United States patents that reach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257, 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

The fidelity of sequences of phosphorothioate oligonucleotides of the invention can be determined using the sensitivities of heteroduplexes to S1 nuclease.

The sequence of the phosphorothioate oligonucleotides can be further substatiated by labeling the 3'hydroxyls of phosphorothioate oligonucleotides with [alpha-$^{3}$P] cordycepin triphosphate, i.e. 3'-deoxyadenosine-5'-triphosphate. The resultant oligonucleotides may be subjected to enzymatic degradation.

The relative ability of phosphorothioate oligonucleotides having substantially chirally pure intersugar linkages, as compared to the identical racemic sequence, to bind to complementary strands is compared by determining the melting temperature of a hybridization complex of each oligonucleotide with the complementary strand. The melting temperature ($T_m$), a characteristic physical property of double helixes, denotes the temperature in degrees centigrade at which 50% helical versus coiled (unhybridized) forms are present. $T_m$ is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$. The higher the $T_m$, the greater the strength of the binding of the strands. Non Watson-Crick base pairing has a strong destabilizing effect on the $T_m$. Consequently, as close to optimal fidelity of base pairing as possible is desired to have optimal binding of an oligonucleotide to its targeted RNA.

Phosphorothioate oligonucleotides of the invention are also evaluated as to their resistance to the degradative ability of a variety of exonucleases and endonucleases. Phosphorothioate oligonucleotides are treated with nucleases and then analyzed, as for instance, by polyacrylamide gel electrophoresis (PAGE) followed by staining with a suitable stain such as Stains All™ (Sigma Chem. Co., St. Louis, Mo.). Degradation products are quantitated using laser densitometry.

The sensitivity of phosphorothioate oligonucleotide-RNA heteroduplexes to catalytic activity of RNase H is also easily assessed. A phosphorothioate oligonucleotide can be incubated with a radiolabeled target mRNA (synthesized as for instance via T7 RNA polymerase) at various temperatures for hybridization. Heteroduplexes can then be incubated at 37° C. with RNase H from E. coli according to the procedure of Minshull, J, and Hunt, T., Nuc. Acid Res., 1986. 6433–6451. Products are then assessed for RNase H activity by Northern Blot analysis wherein products are electrophoresed on a 1.2% agarose/formaldehyde gel and transferred to nitrocellulose. Filters are then probed using a random primer [$^{32}$P]-labeled cDNA complementary to target mRNA and quantitated by autoradiography. The effect of chirality on the relative ability of a heteroduplex to act as a substrate for RNase H is then calculated for various phosphorothiuoate analogs.

Comparisons of the susceptibility of heteroduplexes to the catalytic action of E. coli RNase H and mammalian RNAse H are performed. Heteroduplexes are incubated in rabbit reticulocyte lysates under conditions of translation and assayed via Northern blot analysis for catalytic cleavage of mRNA by endogenous RNase H. This allows for determination of the effects of chirality on mammalian RNAse H activity.

For therapeutic or pharmaceutical use, the compounds of the present invention may be taken up in pharmaceutically acceptable carriers such as, for example, solutions, suspensions, tablets, capsules, ointments, elixirs and injectable compositions. The dosage administered depends upon factors such as the nature and severity of the condition, the stage of the condition, and the condition of the patient. An effective amount of oligonucleotide may be from about 10 μg/kg body weight to about 1000 μg/kg body weight.

The oligomeric compounds of the present invention can be used in diagnostics, therapeutics and as research reagents and kits. The oligomeric compounds of the present invention can also be used in pharmaceutical compositions by including a suitable pharmaceutically acceptable diluent or cattier. These compounds can further be used for treating organisms having a disease characterized by the undesired production of a protein. For this purpose, the organism is contacted with an oligonucleotide having a sequence that is capable of specifically hybridizing with a strand of nucleic acid encoding the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single ails, cellular populations or organelles can also be included within the definition of organisms that can be treated with therapeutic or diagnostic oligonucleotides.

The formulation of therapeutic compositions and their subsequent administration is believed to be within the skill of those in the an. In general, for therapeutics, a patient in need of such therapy is administered an oligomer in accordance with the invention, commonly in a pharmaceutically acceptable carrier, in doses ranging from 0.01 μg to 100 g per kg of body weight depending on the age of the patient and the severity of the disease state being treated. Further, the treatment may be a single dose or may be a regimen that may last for a period of time which will vary depending upon the nature of the particular disease, its severity and the overall condition of the patient, and may extend from once daily to once every 20 years. Following treatment, the patient is monitored for changes in his/her condition and for alleviation of the symptoms of the disease state. The dosage of the oligomer may either be increased in the event the patient does not respond significantly to current dosage levels, or the dose may be decreased if an alleviation of the symptoms of the disease state is observed, or if the disease state has been ablated.

In some cases it may be more effective to treat a patient with an oligomer of the invention in conjunction with other traditional therapeutic modalities. For example, a patient being treated for AIDS may be administered an oligomer in conjunction with AZT, or a patient with atherosclerosis may be treated with an oligomer of the invention following angioplasty to prevent reocclusion of the treated arteries.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to several years.

Following successful treatment, it may be desirable to have the patient undergo maintenance therapy to prevent the recurrence of the disease state, wherein the oligomer is administered in maintenance doses, ranging from 0.01 μg to 100 g per kg of body weight, once or more daily, to once every several years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

Treatments of this type can be practiced on a variety of organisms, ranging from unicellular prokaryotic and eukaryotic organisms to multicellular eukaryotic organisms. Any organism that utilizes DNA-RNA transcription or RNA-protein translation as a fundamental pan of its hereditary, metabolic or cellular control is susceptible to therapeutic and/or prophylactic treatment in accordance with the present invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

Those skilled in the art will appreciate that numerous changes and modifications may be made to the preferred embodiments of the invention and that such changes and modifications may be made without departing from the spirit of the invention. It is, therefore, intended that the appended claims cover all such equivalent variations as fall within the true spirit and scope of the invention.

There are a many therapeutic indications and general uses for compounds of the present invention. Representative indications and uses include the following:

One therapeutic indication of particular interest is psoriasis. Psoriasis is a common chronic and recurrent disease characterized by dry, well-circumscribed, silvery, scaling papules and plaques of various sizes. The disease varies in severity from a few lesions to widespread dermatosis with disabling arthritis or exfoliation. The ultimate cause of psoriasis is not known, but the thick scaling that occurs is probably due to increased epidermal cell proliferation (The Merck Manual of Diagnosis and Therapy. 15th Ed., pp. 2283–2285, Berkow et al., eds., Rahway. N.J., 1987). Inhibitors of Protein Kinase C (PKC) have been shown to have both antiproliferative and anti-inflammatory effects in vitro. Some antipsoriasis drugs, such as cyclosporin A and anthralin, have been shown to inhibit PKC, and inhibition of PKC has been suggested as a therapeutic approach to the treatment of psoriasis (Hegemann, L. and G. Mahrle. Pharmacology of the Skin, H. Mukhtar, ed., pp. 357–368. CRC Press, Boca Raton. Fla., 1992). Antisense compounds targeted to Protein Kinase C (PKC) proteins are described in U.S. Pat. No. 5,620,963 to Cook et al, and U.S. Pat. No. 5,681,747 to Boggs et al.

Another type of therapeutic indication of interest is inflammatory disorders of the skin. These occur in a variety of forms including, for example, lichen planus, toxic epidermal necrolyis (TEN), ertythema multiforme and the like (The Merck Manual of Diagnosis and Therapy, 15th Ed., pp. 2286–2292, Berkow et al., eds., Rahway, N.J., 1987), Expression of ICAM-1 has been associated with a variety of inflammatory skin disorders such as allergic contact dermatitis, fixed drug eruption, lichen planus and psoriasis (Ho et al., J. Am. Acad Dermatol., 1990, 22, 64; Grifths et al., Am. J. Pathology, 1989, 135, 1045; Lisby et al., Br. J. Dermatol., 1989,120,479; Shiohara et al., Arch. Dermatol., 1989, 125, 1371; Regezi et al., Oral Surg. Oral Med. Oral Pathol., 1996, 81, 682). Moreover, intraperitoneal administration of a monoclonal antibody to ICAM-1 decreases ovalbumin-induced eosinophil infiltration into skin of mice (Hakugawa et al., J. Dermatol., 1997, 24, 73). Antisense compounds targeted to ICAM-1 are described in U.S. Pat. Nos. 5,514,788 and 5,591,623, and co-pending U.S. patent applications Ser. Nos. 09/009,490 and 09/062,416, Jan. 20, 1998 and Apr. 17, 1998, respectively, all to Bennett et al.

Other antisense targets for skin inflammatory disorders are VCAM-1 and PECAM-1, lntraperitoneal administration of a monoclonal antibody to VCAM-1 decreases ovalbumin-induced eosinophil infiltration into the skin of mice (Hakugawa et al., J. Dermarol., 1997, 24, 73). Antisense compounds targeted to VCAM-1 are described in U.S. Pat. Nos. 5,514,788 and 5,591,623. PECAM-1 proteins are glycoproteins which are expressed on the surfaces of a variety of cell types (for reviews, see Newman, J. Clin. Invest., 1997, 99, 3 and DeLisser et al., Immunol. Today, 1994, 15, 490). In addition to directly participating in cell-cell interactions, PECAM-1 apparently also regulates the activity and/or expression of other molecules involved in cellular interactions (Litwin et al., J. Cell Biol., 1997, 139, 219) and is thus a key mediator of several cell:cell interactions. Antisense compounds targeted to PECAM-1 are described in co-pending U.S. patent application Ser. No. 09/044,506, filed Mar, 19, 1998, by Bennett et al.

Another type of therapeutic indication of interest for oligonucleotides encompasses a variety of cancers of the skin. Representative skin cancers include benign tumors (warts, moles and the like) and malignant tumors such as, for example, basal cell carcinoma, squamous cell carcinoma, malignant melanoma, Pagers disease, Kaposi's sarcoma and the like (The Merci Manual of Diagnosis and Therapy, 15th Ed., pp. 2301–2310, Berkow et al., eds., Rahway, N.J., 1987). A number of molecular targets involved in tumorigenesis, maintenance of the hyperproliferative state and metastasis are targeted to prevent or inhibit skin cancers, or to prevent their spread to other tissues.

The ras oncogenes are guanine-binding proteins that have been implicated in cancer by, e.g., the fact that activated ras oncogenes have been found in about 30% of human tumors generally; this figure approached 100% in carcinomas of the exocrine pancreas (for a review, see Downward, Trends it Biol. Sci., 1990, 15, 469). Antisense compounds targeted to H-ras and K-ras are described in U.S. Pat. No. 5,582,972 to Lima et al., U.S. Pat. No. 5,582,986 to Monia et al, and U.S. Pat. No. 5,661,134 to Cook et al., and in published PCT application WO 94/08003.

Protein Kinase C (PKC) proteins have also been implicated in tumorigenesis. Antisense compounds targeted to Protein Kinase C (PKC) proteins are described in U.S. Pat. No. 5,620,963 to Cook et al, and U.S. Pat. No. 5,681,747 to Boggs et al.

Also of interest are AP-1 subunits and JNK proteins, particularly in regard to their roles in tumorigenesis and metastasis. The process of metastasis involves a sequence of events wherein (1) a cancer cell detaches from its extracellular matrices, (2) the detached cancer cell migrates to another portion of an animal's body, often via the circulatory system, and (3) attaches to a distal and inappropriate extracellular matrix, thereby created a focus from which a secondary tumor can arise. Normal cells do not possess the ability to invade or metastasize and/or undergo apoptosis (programmed cell death) if such events occur (Ruoslahti, Sci. Amen., 1996, 275, 72). However, many human tumors have elevated levels of activity of one or more matrix metalloproteinases (MMPs) (Stetler-Stevenson et al., Annu. Rev. Cell Biol., 1993, 9, 541; Bernhard et al., Proc. Natl. Acad. Sci. (U.S.A.), 1994, 91, 4293. The MMPs are a family of enzymes which have the ability to degrade components of the extracellular matrix (Birkedal-Hansen, Current Op. Biol., 1995, 7, 728). In particular, one member of this family, matrix metalloproteinase-9 (MMP-9), is often found to be expressed only in tumors and other diseased tissues (Himelstein et al., Invasion & Metastasis, 1994, 14, 246).

Several studies have shown that regulation of the MMP-9 gene may be controlled by the AP-1 transcription factor (Kerr et al., Science, 1988, 242, 1242; Kerr et al., Cell, 1990, 61, 267; Gum et al., J. Biol. Chem., 1996,271, 10672; Hua et al., Cancer Res., 1996,56,5279). Inhibition of AP-1 function has been shown to attenuate MMP-9 expression (U.S. Pat. No. 5,985,558). AP-1 is a heterodimeric protein having two subunits, the gene products of fos and jun. Antisense compounds targeted to c-fos and c-jun are described in Dean et al. U.S. Pat. No. 5,985,558.

Furthermore, AP-1 is itself activated in certain circumstances by phosphorylation of the Jun subunit at an amino-terminal position by Jun N-terminal kinases (JNKs). Thus, inhibition of one or more JNKs is expected to result in decreased AP-1 activity and, consequentially, reduced MMP expression. Antisense compounds targeted to JNKs are described in Dean et al. U.S. Pat. No. 5,877,309.

Infectious diseases of the skin are caused by viral, bacterial or fungal agents. In the case of Lyme disease, the tick home causative agent thereof, the spirochete Borrelia burgdorferi, up-regulates the expression of ICAM-1, VCAM-1 and ELAM-1 on endothelial cells in vitro (Boggemeyer et al., Cell Adhes. Comm., 1994, 2, 145). Furthermore, it has been proposed that the mediation of the disease by the anti-inflammatory agent prednisolone is due in part to mediation of this up-regulation of adhesion molecules (Hurtenbach et al., Int., J. Immunopharmac., 1996, 18, 281). Thus, potential targets for therapeutic mediation (or prevention) of Lyme disease include ICAM-1, VCAM-1 and ELAM-1 (supra).

Other infectious disease of the skin which are tractable to treatment using the compositions and methods of the invention include disorders resulting from infection by bacterial, viral or fungal agents (The Merck Manual of Diagnosis and Therapy, 15th Ed., pp. 2263–2277, Berkow et al., eds., Rahway. N.J., 1987).

With regards to infections of the skin caused by fungal agents, U.S. Pat. No. 5,691,461 provides antisense compounds for inhibiting the growth of Candida albicans.

With regards to infections of the skin caused by viral agents, U.S. Pat. Nos. 5,166,195, 5,523,389 and 5,591,600 provide oligonucleotide inhibitors of Human Immunodeficiency Virus (HIV). U.S. Pat. No. 5,004,810 provides oligomers capable of hybridizing to herpes simplex virus Vmw65 mRNA and inhibiting its replication. U.S. Pat. No. 5,194,428 and 5,580,767 provide antisense compounds having antiviral activity against influenzavirus. U.S. Pat. No. 4,806,463 provides antisense compounds and methods using them to inhibit HTLV III replication. U.S. Pat. Nos. 4,689, 320, 5,442,049, 5,591,720 and 5,607,923 are directed to antisense compounds as antiviral agents specific to cytomegalovirus (CMV). U.S. Pat. No. 5,242,906 provides antisense compounds useful in the treatment of latent Epstein-Barr virus (EBV) infections. U.S. Pat. Nos. 5,248,670, 5,514,577 and 5,658,891 provide antisense compounds useful in the treatment of herpesvirus infections. U.S. Pat. Nos. 5,457,189 and 5,681,944 provide antisense compounds useful in the treatment of papillomavirus infections. The antisense compounds disclosed in these patents, which are herein incorporated by reference, may be used with the compositions of the invention to effect prophylactic, palliative or therapeutic relief from diseases caused or exacerbated by the indicated pathogenic agents.

Antisense oligonucleotides employed in the compositions of the present invention may also be used to determine the nature, function and potential relationship of various genetic components of the body to disease or body states in animals. Heretofore, the function of a gene has been chiefly examined by the construction of loss-of-function mutations in the gene (i.e., "knock-out" mutations) in an animal (e.g., a transgenic mouse). Such tasks are difficult, time-consuming and cannot be accomplished for genes essential to animal development since the "knock-out" mutation would produce a lethal phenotype. Moreover, the loss-of-function phenotype cannot be transiently introduced during a particular part of the animal's life cycle or disease state: the "knock-out" mutation is always present. "Antisense knockouts," that is, the selective modulation of expression of a gene by antisense oligonucleotides, rather than by direct genetic manipulation, overcomes these limitations (see, for example, Albert et al., Trends in Pharmacological Sciences, 1994, 15, 250). In addition, some genes produce a variety of mRNA transcripts as a result of processes such as alternative splicing; a "knock-out" mutation typically removes all forms of mRNA transcripts produced from such genes and thus cannot be used to examine the biological role of a particular mRNA transcript. Antisense oligonucleotides have been systemically administered to rats in order to study the role of the N-methyl-D-aspartame receptor in neuronal death, to mice in order to investigate the biological role of protein kinase C-a, and to rats in order to examine the role of the neuropeptide Y1 receptor in anxiety (Wahlestedt et al., Nature, 1993, 363:260; Dean et al., Proc. Natl. Acad. Sci. U.S.A., 1994, 91:11762; and Wahlestedt et al., Science, 1993, 259:528, respectively). In instances where complex families of related proteins are being investigated. "antisense knockouts" (i.e., inhibition of a gene by systemic administration of antisense oligonucleotides) may represent the most accurate means for examining a specific member of the family (see, generally. Albert et al., Trends Pharmacol. Sci., 1994, 15:250). By providing compositions and methods for the simple non-parenteral delivery of oligonucleotides and other nucleic acids, the present invention overcomes these and other shortcomings.

The administration of therapeutic or pharmaceutical compositions comprising the oligonucleotides of the invention is believed to be within the skill of those in the art. In general, a patient in need of therapy or prophylaxis is administered a composition comprising a compound of the invention, commonly in a pharmaceutically acceptable carrier, in doses ranging from 0.01 μg to 100 g per kg of body weight depending on the age of the patient and the severity of the disorder or disease state being treated. Dosing is dependent on severity and responsiveness of the disease state to be treated, with the course of treatment lasting from several days to several months, or until a cure is effected or a diminution or prevention of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual antisense compounds, and can generally be estimated based on $EC_{50}$s found to be effective in in vitro and in vivo animal models.

In the context of the invention, the term "treatment regimen" is meant to encompass therapeutic, palliative and prophylactic modalities of administration of one or more compositions of the invention. A particular treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the composition may either be increased in the event the patient does not respond significantly to current dosage levels, or the dose may be decreased if an alleviation of the symptoms of the disorder or disease state is observed, or if the disorder or disease state has been ablated.

An optimal dosing schedule is used to deliver a therapeutically effective amount of the oligonucleotide of the invention. The term "therapeutically effective amount," for the purposes of the invention, refers to the amount of oligonucleotide-containing pharmaceutical composition which is effective to achieve an intended purpose without undesirable side effects (such as toxicity, irritation or allergic response). Although individual needs may vary, determination of optimal ranges for effective amounts of pharmaceutical compositions is within the skill of the art. Human doses can be extrapolated from animal studies (Katocs et al., Chapter 27 In: Remington's Pharmaceutical Sciences, 18th Ed., Gennaro, ed., Mack Publishing Co., Easton, Pa., 1990). Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s) (Nies et al., Chapter 3 In: Goodman & Gilman's The Pharmacological Basis of Therapeutics. 9th Ed., Hardman et al., eds., McGraw-Hill. New York. N.Y., 1996).

Following successful treatment, it may be desirable to have the patient undergo maintenance therapy to prevent the recurrence of the disease state, wherein the bioactive agent is administered in maintenance doses, ranging from 0.01 μg to 100 g per kg of body weight, once or more daily, to once every 20 years. For example, in the case of in individual known or suspected of being prone to an autoimmune or inflammatory condition, prophylactic effects may be achieved by administration of preventative doses, ranging from 0.01 μg to 100 g per kg of body weight, once or more daily, to once every 20 years. In like fashion, an individual may be made less susceptible to an inflammatory condition that is expected to occur as a result of some medical treatment, e.g., graft versus host disease resulting front the transplantation of cells, tissue or an organ into the individual.

Prophylactic modalities for high risk individuals are also encompassed by the invention. As used herein, the term "high risk individual" is meant to refer to an individual for whom it has been determined, via, e.g., individual or family history or genetic testing, that there is a significantly higher than normal probability of being susceptible to the onset or recurrence of a disease or disorder. For example, a subject animal could have a personal and/or family medical history that includes frequent occurrences of a particular disease or disorder. As another example, a subject animal could have had such a susceptibility determined by genetic screening according to techniques known in the art (see, e.g., U.S. Congress, Office of Technology Assessment. Chapter 5 In: Genetic Monitoring and Screening in the Workplace, OTA-BA-455, U.S. Government Printing Office, Washington, D.C., 1990, pages 75–99). As part of a treatment regimen for a high risk individual, the individual can be prophylactically treated to prevent the onset or recurrence of the disease or disorder. The term "prophylactically effective amount" is meant to refer to an amount of a pharmaceutical composition which produces an effect observed as the prevention of the onset or recurrence of a disease or disorder. Prophylactically effective amounts of a pharmaceutical composition are typically determined by the effect they have compared to the effect observed when a second pharmaceutical composition lacking the active agent is administered to a similarly situated individual.

For therapeutic use the oligonucleotide analog is administered to an animal suffering from a disease modulated by some protein. It is preferred to administer to patients suspected of suffering from such a disease an amount of oligonucleotide analog that is effective to reduce the symptomology of that disease. One skilled in the art can determine optimum dosages and treatment schedules for such treatment regimens.

It is preferred that the RNA or DNA portion which is to be modulated be preselected to comprise that portion of DNA or RNA which codes for the protein whose formation or activity is to be modulated. The targeting portion of the composition to be employed is, thus, selected to be complementary to the preselected portion of DNA or RNA, that is to be an antisense oligonucleotide for that portion.

In accordance with one preferred embodiment of this invention, the compounds of the invention hybridize to HIV mRNA encoding the tat protein, or to the TAR region of HIV mRNA. In another preferred embodiment, the compounds mimic the secondary structure of the TAR region of HIV mRNA, and by doing so bind the tat protein. Other preferred compounds complementary sequences for herpes, papilloma and other viruses.

It is generally preferred to administer the therapeutic agents in accordance with this invention internally such as orally, intravenously, or intramuscularly. Other forms of administration, such as transdermally, topically, or intralesionally may also be useful. Inclusion in suppositories may also be useful. Use of pharmacologically acceptable carriers is also preferred for some embodiments.

This invention is also directed to methods for the selective binding of RNA for research and diagnostic purposes. Such selective, strong binding is accomplished by interacting such RNA or DNA with compositions of the invention which are resistant to degradative nucleases and which hybridize more strongly and with greater fidelity than known oligonucleotides or oligonucleotide analogs.

EXAMPLES

General

Solvents were dried by distillation:

THF over sodium benzophenone ketyl; acetonitrile and triethylamine over calcium hydride; and pyridine over barium oxide. DBU is distilled under vacuum and then stored over 4 A Linde molecular sieves under argon. PCl, is first degassed by refluxing for 2 h under argon followed by fractional distillation and storage under argon. Water is HPLC grade obtained from Aldrich Chemical Co. Inc.

Example 1

Isomerically Pure R and S Isomers of 4-mercapto-4methyl-2-pentanol

R4-mercapto-4-methyl-2-pentanol and S-4-mercapto-4-methyl-2-pentanol are synthesized according to the procedure of Eliel and Morris-Natschke (Eliel, E. L., Morris-Natschke, S., J.Am.Chem.Soc, 1984, 106, 2937–2942).

Example 2

Rp Precursor, Compound 1

$PCl_3$ (1.3 mL, 15 mmol) is introduced via a syringe into a dry 100-mL round-bottomed flask containing 20 mL of dry THF that has been flushed with argon and sealed with a septum. The flask is cooled to −78° C. in a dry ice/acetone bath, and a solution of (R)-4-mercapto-4-methyl-2-pentanol (15 mmol) in THF (15 mL) containing triethylamine (6.9 mL, 50 mmol) is added via a syringe. The reaction mixture is stirred for 30 min at −78° C. and then warmed to 0° C. for 1 hour. The reaction mixture is partitioned between $CH_2Cl_2$ and saturated $NaHCO_3$ and washed with saturated NaCl and dried over anhydrous $Na_2SO_4$ to give the title compound.

Example 3

Compound 2

Compound 1 in hexane is treated with morpholine by careful dropwise addition at 0° C. The cold bath is removed, and the mixture is stirred at room temperature for an additional 1 hour. Morpholine hydrochloride is removed by filtration, and Compound 2 is purified by silica gel column chromatography.

Example 4

General Procedure for the Synthesis of Monomers Used for Synthesizing Rp Linkages, Structure 3

To a sample of 2'-deoxy-5'-O-DMT nucleoside (2'-O-deoxy, 5'-O-DMT6-N-benzoyl adenosine, 2'-Q-deoxy, 5'-O-DMT-4-N-benzoyl cytidine. 2'-O-deoxy-5'-O-DMT-2-N-isobutyl guanosine, 2'-O-deoxy-5'-O-DMT thymidine or a modified optionally protected 5-O-DMT-nucleoside) 10 mmol in dry $CH_2Cl_2$ at −78° C. is added 20 mL of a 15 mmol solution of 1H-tetrazole (11 mmol), in THF via syringe. The reaction mixture is stirred at −78° C. for 30 min, the cooling bath is removed, and the solution is warmed to room temperature. To this solution is added Compound 2 in THF (11 mmol) dropwise with stirring for 2–4 hours. The sulfurization reagent 3H-1,2-benzodithiole-3-one-1,1-dioxide (2% in $CH_3CN$), (Iyer et al. , J. Am. Chem. Soc, 1990, 112, 1253) is added with stirring for 1 hour. The solvent is evaporated and the nucleoside oxathiane intermediate is purified by silica gel column chromatography to afford the respective monomeric compound having Structure 3.

Example 5

Attachment of Thymidine to Solid Support (5'-HO-T-CPG)

Thymidine was attached to solid support following a literature procedure (Damha et al., Nucleic Acids Res., 1990, 18, 3813–3821). To a dry 6 mL Hypovial was added 5'-O-DMT thymidine (109 mg, 0.2 mmol). CPG with sarcosinyl-succinonyl linker (Brown et al., J. Chem. Soc. Chem. Comm. 1989, 891) (1.0 g), 4-DMAP (12 mg, 0.1 mmol), triethylamine (80 μL), DEC (384 mg. 2.0 mmol), and anhydrous pyridine (5 mL). The mixture was shaken at room temperature for 24 h. Pentachlorophenol (134 mg, 0.5 mmol) was added, and the mixture was shaken for an additional period of 16 h. The CPG was filtered off and washed successively with pyridine, $CH_2Cl_2$, and ether. The CPG was treated with reagent grade piperidine (5 mL), and the slurry was shaken for 10 min. The resulting CPG was filtered off, washed successively with $CH_2Cl_2$ and ether, and dried under vacuum. The dried CPG was mixed with equal parts of two solutions of 0.5 M acetic anhydride in THF and 0.5 M 4DMAP/2,4,6-trimethylpyridine in THF (4 mL each). The slurry was shaken for 2 hours and washed successively with pyridine, $CH_2Cl_2$, THF and ether. The loading amount was measured by' Trityl Analysis, 37.9 mol/g. Detritylation with 3% trichloroacetic acid in 1,2-dichloroethane afforded the immobilized thymidine.

Example 6

Solid Support Bound T- Rp-T Dimer, Compound 4

To a sintered glass funnel are added 5'-HO-TCPG (27 mg, 1 mol) and a solution of Structure 3, where the base is thymine, in acetonitrile (0.2 mL, 0.1 M) followed by 30 μL of DBU (0.2 mmol) added by syringe. After 15 minutes, the solid support is washed with acetonitrile (3×2 mL), and then Besucage's reagent (0.2 mL, 0.1 M in THF) is added. The solid support on washing with anhydrous $CH_3CN$ gives the title dimer.

Example 7

T-Rp-T Dimer, Compound 5

Compound 4 is treated with $NH_4OH$ (28%) at 50° C. For 2 h. The solution is evaporated to dryness, and the residue is dissolved in water (1 mL) and filtered. The resulting crude material which has been cleaved from the solid support, is purified and analyzed by HPLC to give Compound 5, a TT dimer having a chiral Rp internucleoside linkage.

Example 8

Compound 6

Compound 6 is prepared following the procedures used to prepare Compound 1, Example 2, S-4-mercapto-4-methyl-2-pentanol (15 mmol) is treated with $PCl_3$ (15 mmol l to give upon purification Compound 6.

Example 9

Compound 7

Compound 6 in hexane is treated with morpholine by careful dropwise addition at 0° C. The cold bath is removed, and the mixture is stiffed at room temperature for an additional 1 hour. Morpholine hydrochloride is removed by filtration, and Compound 7 is purified by silica gel column chromatography.

Example 10

Monomers used for Sp Linkages, Structure 8

Compound 7 is reacted with a 5'-O-DMT nucleoside in the presence of tetrazole followed by addition of sulfur (Beaucage reagent) to give the desired oxathiane phosphorous derivative compound 8. This procedure is illustrated for the Rp isomer in Example 4 above. Compound 8 is purified by silica gel column chromatography.

Example 11

Solid Support Bound T Sp-T Dimer, Compound 9

To a sintered glass funnel are added 5'-HO-T-CPG (Example 5) (27 mg, 1 mmol), a solution of compound 8 in acetonitrile (0.2 mL, 0.1 M), and 30 μL of DBU (0.2 mmol, via syringe). After 15 minutes, the solid support is washed with acetonitrile (3×2 mL), and then Beaucage's reagent (0.2 mL, 0.1M in THF) is added. The solid support on standing for 10 minutes followed by washing with anhydrous $CH_3CN$ gives the title dimer.

Example 12

T-Sp-T Dimer, Compound 10

Compound 9 is treated with $NH_4OH$ (28%) at 50° C. for 2 h. The solution is evaporated to dryness, and the residue is dissolved in water (1 mL) and filtered. Compound 10 is purified and analyzed using HPLC. The four membered thiane formation facilitates the formation of the product (Compound 10).

Example 13

5-methyl-2-(1-methyl-1-thioethyl) Cyclohexanol, Compound 11

Compound 11, is obtained from (+)-pulegone, readily available in enantiomerically pure form following a literature procedure (Lynch et al., Tetrahedron Lett., 1981, 22, 2855–2888 and Lynch et al., J. Am. Chem. Soc., 1984, 106, 2943–2948).

Example 14

Compound 12

Compound 11 and phosphorous trichloride are added in equimolar proportions to $CH_2Cl_2$, containing two equivalents of pyridine at −78. After stirring for 1 hour, pyridinium hydrochloride is filtered off, and the solution is concentrated and purified to give Compound 12.

Example 15

Compound 13

Compound 12 in hexane is treated with morpholine by careful dropwise addition at 0° C. The cold bath is removed, and the mixture is stirred at room temperature for an additional 1 hour. Morpholine hydrochloride is removed by filtration and Compound 13 is purified by silica gel column chromatography.

Example 16

Chiral Monomers Used for Rp Linkages, Structure 14

To a selected 2'-deoxy-5-O-DMT nucleoside (2'-O-deoxy-5'-O-DMT-6-N-benzoyl adenosine. 2'-O-deoxy-5'-O-DMT-4-N-benzoyl cytodine. 2'-O-deoxy-5'-O-DMT-2-N-butyryl guanosine, 2'-O-deoxy-5'-O-DMT-thymidine or modified optionally protected 5-O-DMT-nucleoside) 10 mmol in dry $CH_2Cl_2$, is added 1H tetrazole (11 mmol). Compound 13 (11 mmol) is added dropwise with stirring for 2–4 hours. The resulting intermediate is oxidized with Beaucage reagent as described above for Compound 3. The nucleoside oxathiane intermediate is purified by silica gel column chromatography, Example 17

General Procedure for Preparing Chiral Dimers Having Structure 15

Compound 14 is condensed with a 5'-HO-T-CPG (Example 5), or other solid support bound 5'-OH-nucleoside, using DBU to give a compound having Structure 15 as described above for Compound 4. Dimers having Structure 15 are treated as per the procedure of Example 7 to cleave the dimer from the CPG and to deblock the phosphorus thereby giving the free deblocked dimer having Structure 15a.

Example 18

Compound 16

Starting from (−)-pulegone, commercially available from Fluka, the isomer of (−)-5-methyl-2-(1-methyl-1-thioethyl) cyclohexanol is obtained following literature procedures (Lynch ibid). The compound (−)-5-methyl-2-(1-methyl-1-thioethyl) cyclohexanol is treated with $PCl_3$ in $CH_2Cl_2$ containing two equivalents of pyridine at −78° C. After stirring for 1 hour, pyridinium hydrochloride is filtered off, and the solution is concentrated and purified to give Compound 16.

Example 19

Compound 17

Compound 16 in hexane is treated with morpholine by careful dropwise addition at 0° C. The cold bath is removed, and the mixture is stirred at room temperature for an additional 1 hour. Morpholine hydrochloride is removed by filtration, and Compound 17 is purified by silica gel column chromatography.

Example 20

Synthesis of Monomers Having Structure 18

To a selected 2'-deoxy-5-O-DMT-nucleoside (2'-O-deoxy-5'-O-DMT-6-N-benzoyl adenosine, 2'-O-deoxy-5'-O-DMT-4-N-benzoyl cytodine, 2'-O-deoxy-5'-O-DMT-2-N-butyryl guanosine, 2'-O-deoxy-5'-O-DMT thymidine or modified optionally protected 5-O-DMT-nucleoside) 10 mmol in dry $CH_2Cl_2$ is added 1H tetrazole (11 mmol) followed by dropwise addition of Compound 17 (11 mmol) and stirring for 2–4 hours. The sulfurization reagent 3H-1,2-benzodithiole-3-one-1,1-dioxide (2% in $CH_3CN$, Iyer ibid), is added and stirred for 1 hour. Solvent is evaporated and the crude material is purified by silica gel column chromatography to give Compound 18.

Example 21

General Procedure for Preparing Sp Diners Using Compound 18

Compound 18 is condensed with a 5'-HO-T-CPG (Example 5), or other solid support bound 5'-OH-nucleoside, using DBU to give a compound having Structure 18 as described above for Compound 4. Diners prepared from Compound 18 are cleaved from the CPG and deblocked thereby giving the free deblocked Sp chiral dimer.

Example 22

5c-Methyl-2t [(1-methyl-1-methylamino) Ethyl]-cyclohexan-1r-ol

The title compound is synthesized according to a literature procedure using (+)-pulegone (He et al., J. Org. Chem., 1990, 55, 2114–2119) by first preparing 5c-Methyl-2t [(1-methyl-1-benzylamino) ethyl]-cyclohexan-1r-ol. This compound is subjected to hydrogenolysis by $Pd/H_2$ to give the corresponding amino alcohol (removal of benzyl group). The amino alcohol is then treated with 1 equivalent of HCHO followed by $NaCNBH_3$ reduction to give the title Compound.

Example 23

Compound 20

Compound 19 and phosphorous trichloride are added in equimolar proportions to $CH_2Cl_2$ containing two equivalents of pyridine at −78° C. After stirring for 1 hour, pyridinium hydrochloride is filtered off, and the solution is concentrated and purified to give a chloro-intermediate compound. The chloro-intermediate compound in hexane is treated with morpholine by careful dropwise addition at 0° C. The cold bath is removed, and the mixture is stirred at room temperature for an additional 1 hour. Morpholine hydrochloride is removed by filtration, and the morpholino compound is purified by silica gel column chromatography.

To a selected 2'-deoxy-5-O-DMT-nucleoside (2'-O-deoxy-5'-O-DMT-6-N-benzoyl adenosine, 2'-O-deoxy-5'-O-DMT-4-N-benzoyl cytodine, 2'-O-deoxy-5'-O-DMT-2-N-butyryl guanosine, 2'-O-deoxy-5'-O-DMT-thymidine or modified optionally protected 5-O-DMT-nucleoside) 10 mmol in dry $CH_2Cl_2$ is added 1H tetrazole (11 mmol) followed by dropwise addition of the morpholino compound (11 mmol) and stirring for 2–4 hours. The sulfurization reagent 3H-1,2-benzodithiole-3-one-1,1-dioxide (2% in $CH_3CN$, Iyer ibid), is added and stirred for 1 hour. Solvent is evaporated and the nucleoside oxathiane intermediate Compound 20 is purified by silica gel column chromatography.

Example 24

Compound 21

Compound 20 is condensed with a 5'-HO-T-CPG (Example 5), or other solid support bound 5'-OH-nucleoside, using DBU to give a compound having Structure 21 as described above for Compound 4. A capping step is added to cap the free amine formed.

Example 25

Generation of Rp Diner 21a From Compound 21

Compound 21 is treated with concentrated ammonium hydroxide for 16 hours to give the cleaved deblocked dimer as the Rp isomer and the chiral adjuvant derived products 22 and 23.

Example 26

Compound 24

From the naturally occuring (−)-pulegone (available from Fluka), compound 24 is obtained as a Chiral Adjuvant following a literature procedure (He et al., Tetrahedron, 1987, 43, 4979–4987). Following the procedures illustrated for compound 19, compound 24 is obtained.

Example 27

Monomer, Compound 20

Compound 19 is treated with $PCl_3$ (1 equivalent) with excess of Hunig base in THF solvent at −5° C. for 10 minutes. The resulting chloro compound is treated with a selected 2'-deoxy-5-O-DMT-nucleoside having a free 31-OH group (2'-O-deoxy-5'-O-DMT-6-N-benzoyl adenosine, 2'-O-deoxy-5'-O-DMT-4-N-benzoyl cytodine, 2'-O-deoxy-5'-O-DMT-2-N-butyryl guanosine, 2'-O-deoxy-5'-O-DMT thymidine or modified optionally protected 5-O-DMT-nucleoside). TLC and $^{13}C$ NMR analysis is used to reveal the formation of a single diastereomer. The crude material is washed with saturated sodium bicarbonate and dried over anhydrous sodium sulfate. The resulting material is purified either by crystallization or by silica gel column chromatography.

Example 28

Protected Dimer. Compound 21

Purified compound 20 is condensed with a 5'-HO-T-CPG (Example 5), or other solid support bound 5'-OH-nucleoside (such as 2'-O-deoxy-6-N-benzoyl adenosine, 2'-O-deoxy-4-N-benzoyl cytidine, 2'-O-deoxy-2-N-isobutyryl guanosine or other modified optionally protected 5'-OH'-3'-CPG-nucleoside), for 2 hours using tetrazole as the coupling agent. The resultant free amine is capped with acetic anhydride, and the dimer is oxidized with Beaucage reagent to give Compound 21. Compound 21 is cleaved from the solid support and deprotected by treatment with concentrated ammonium hydroxide (30%, 12 hours). The chiral auxiliary is removed as compound 22 or 23 and the oligomer is purified by HPLC. The nucleoside dimer is treated with 80% aqueous acetic acid to remove the 5'-triyl group. The Rp configuration is assigned as described below in the procedures.

Example 29

Sp Dimer, Compound 25

Compound 25 is synthesized from compound 24 as described for compound 20. Compound 25 on coupling with nucleoside-CPG and purification as previously described for the Rp isomer gives the Sp isomer.

Example 30

Synthesis of Chirally Pure 5'-$T_{Sp}T_{Rp}T_{Rp}T_{Rp}T_{Rp}T_{Sp}$T-3' Phosphorothioate Heptamer

50milligram (2 μmole of 5'-O-dimethoxytritylthymidine bound to CPG (controlled pore glass) through an ester linkage is taken up in a glass reactor, and a toluene solution of 39% dichloroacetic acid (v/v) is added to deprotect the 5'-hydroxyl group. The product is washed with acetonitrile and a 0.2 M solution of Compound 8 (B═T) in acetonitrile (25 fold excess) and a 0.5 M solution of DBU in acetonitrile (200 fold excess) is added and allowed to react at room temperature for 15 minutes. The product is washed with acetonitrile followed by the addition of a 0.2 M solution of Beaucage reagent in acetonitrile with reaction allowed to progress at room temperature for 5 minutes. This sulfurization step is repeated one more time for 5 minutes. The support is washed with acetonitrile, and then a solution of acetic anhydride/lutidine/THF (1:1:8), and N-methyl imidazole/THF is added to cap any unreacted 5'-hydroxyl groups. The product is washed with acetonitrile.

In the next cycle Compound 3 (B═T) is used as the incoming monomer and the cycle is repeated. This complete cycle is repeated four more times to introduce the Rp linkages. In the final cycle Compound 8 is used as the incoming monomer which introduces the terminal Sp linkage. The solid support containing the heptamer is treated with 30% aqueous ammonium hydroxide solution for 90 minutes at room temperature. The aqueous solution is filtered, and concentrated under reduced pressure to give the chirally pure phosphorothioate heptamer.

Example 31

Synthesis of Chirally Pure 5'-d($G_{Sp}A_{Rp}C_{Sp}$T)-3' Phosphorothioate Tetramer 50 milligram (2 μmole) of 5'-O-dimethoxytritylthymidine bound to CPG (controlled pore glass) through an ester linkage is taken up in a glass reactor, and a toluene solution of 3% dichloroacetic acid in toluene (volume/volume) is added to deprotect the 5'-hydroxyl group. The product is washed with acetonitrile, a 0.2 M solution of Compound 8 with B═$dC^{Bz}$ in acetonitrile (25 fold excess) and a 0.5 M solution of DBU in acetonitrile (200 fold excess) are added, and allowed to react at room temperature for 15 20 minutes. The product is washed with acetonitrile and a 0.2 M solution of Beaucage reagent in acetonitrile is added and allowed to react at room temperature for 5 minutes. This sulfurization step is repeated one more time for 5 minutes. The support is washed with acetonitrile, and then a solution of acetic anhydride/lutidine/THF (1:1:8), and N-methyl imidazole/THF is added to cap any unreacted 5'-hydroxyl groups followed by washing with acetonitrile.

In the next cycle Compound 3 (B═$dA^{Bz}$) is used as the incoming monomer and the cycle is repeated. Thus, a 0.2 30 M solution of Compound 3 with B═$dA^{Bz}$ in acetonitrile (25 fold excess) and a 0.5 M solution of DBU in acetonitrile (200 fold excess) is added and allowed to react at room temperature for 15 minutes. The product is washed with acetonitrile and a 0.2 M solution of Beaucage reagent in acetonitrile is added and allowed to react at room temperature for 5 minutes. This sulfurization step is repeated one more time for 5 minutes. The support is washed with acetonitrile, a solution of acetic anhydride/lutidine/THF (11:8) and a solution of N-methyl imidazole/THF are aided to cap any unreacted 5'-hydroxyl groups. The product is washed with acetonitrile. A solution of 3% dichloroacetic acid in toluene (v/v) is added to deprotect the 5'-hydroxyl groups and the product is washed with acetonitrile.

Compound 8 (0.2 M solution) with B═$dG^{iBu}$ in acetonitrile (25 fold excess) and a 0.5 M solution of DBU in acetonitrile (200 fold excess) are added and allowed to react at room temperature for 15 minutes. The product is washed with acetonitrile, and then a 0.2 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8) and a solution of N-methyl imidazole/THF are added to cap any unreacted 5'-hydroxyl groups. The product is washed with acetonitrile.

The desired tetamer is deblocked and cleaved from the solid support by treatment with a 30% aqueous solution of ammonium hydroxide for 90 minutes at room temperature followed by heating to 55° C. for 12 hours. The aqueous solution is filtered and concentrated under reduced pressure to give the title phosphorothioate tetramer of 5'-d$G_{Sp}$-d$A_{Rp}$d$C_{Sp}$T-3'.

Example 32

Oligonucleotide Synthesis: General Procedures

The oligonucleotides listed in Table 1 are synthesized by following the procedures described above. For generating chirally mixed (Rp and Sp) sites, commercial amidites (Perseptive Biosystems) are used and standard synthesis conditions are used.

For introducing Rp linkages with appropriate nucleobases monomers 3, 14 or 20 are used.

For introducing Sp linkages with appropriate nucleobases monomers 8, 18 or 25 are used.

The solid support employed is controlled pore glass CPG with sarcosinyl-succinonyl linker (Brown et al., J. Chem. Soc. Chem. Comm., 1989, 891).

The sulfurization reagent employed is 3H-1,2-benzodithiole-3-one-1.1-dioxide (2% in $CH_3CN$, Iyer ibid).

A solution of acetic anhydride/lutidine/THF (1:1:8), and N-methyl imidazole/THF is added mixture to cap any unreacted 5'-hydroxyl group.

The preferred reagents have been listed above for the synthesis of chirally pure oligonucleotides. Those skilled in the art will realize that many other reagents and materials are equally amenable to the present invention and that this list is not exclusive.

TABLE I

| Compound | Sequence | ISIS #/Target |
|---|---|---|
| I | GCCCAAGCTG GCATCCGTCA | (ISIS-2302)/Human ICAM-1 |
| II | $G_{Sp}$CCCAAGCTG GCATCCGTC5#A | |
| III | $G_{Sp}C_{Rp}C_{Rp}C_{Rp}A_{Rp}A_{Rp}G_{Rp}C_{Rp}T_{Rp}G_{Rp}G_{Rp}C_{Rp}A_{Rp}T_{Rp}C_{Rp}C_{Rp}G_{Rp}T_{Rp}C_{Sp}A$ | |
| IV | TCCGTCATCGCTCCTCAGGG | (ISIS-2503)/Human H-ras |
| V | $T_{Sp}$CCGTCATCGCTCCTCAGG$_{Sp}$G | |
| VI | $T_{Sp}C_{Rp}C_{Rp}G_{Rp}T_{Rp}C_{Rp}A_{Rp}T_{Rp}C_{Rp}G_{Rp}C_{Rp}T_{Rp}C_{Rp}C_{Rp}T_{Rp}C_{Rp}A_{Rp}G_{Rp}G_{Sp}G$ | |
| VII | GTTCTCGCTGGTGAGTTTCA | (ISIS-3521)/Human PKC-α |
| VIII | $G_{Sp}$TTCTCGCTGGTGAGTTTC$_{Sp}$A | |
| IX | $G_{Sp}T_{Rp}T_{Rp}C_{Rp}T_{Rp}C_{Rp}G_{Rp}C_{Rp}T_{Rp}G_{Rp}G_{Rp}T_{Rp}G_{Rp}A_{Rp}G_{Rp}T_{Rp}T_{Rp}T_{Rp}C_{Sp}A$ | |
| X | TCCCGCCTGTGACATGCATT | (ISIS-5312)/Human C-raf |
| XI | $T_{Sp}$CCCGCCTGTGACATGCAT$_{Sp}$T | |
| XII | $T_{Sp}C_{Rp}C_{Rp}C_{Rp}G_{Rp}C_{Rp}C_{Rp}T_{Rp}G_{Rp}T_{Rp}G_{Rp}A_{Rp}C_{Rp}A_{Rp}T_{Rp}G_{Rp}C_{Rp}A_{Rp}C_{Sp}T$ | |
| XIII | GTGCTCATGGTGCACGGTCT | (ISIS-14803)/Human HCV |
| XIV | $G_{Sp}$TGCTCATGGTGCACGGTC$_{Sp}$T | |
| XV | $G_{Sp}T_{Rp}G_{Rp}C_{Rp}T_{Rp}C_{Rp}A_{Rp}T_{Rp}G_{Rp}G_{Rp}T_{Rp}G_{Rp}C_{Rp}A_{Rp}C_{Rp}G_{Rp}G_{Rp}T_{Rp}C_{Sp}T$ | |
| XVI | TGCATCCCCCAGGCCACCAT | (ISIS-3082)/Murine ICAM-1 |
| XVII | $T_{Sp}$GCATCCCCCAGGCCACCA$_{Sp}$T | |
| XVIII | $T_{Sp}G_{Rp}C_{Rp}A_{Rp}T_{Rp}C_{Rp}C_{Rp}C_{Rp}C_{Rp}C_{Rp}A_{Rp}G_{Rp}G_{Rp}C_{Rp}C_{Rp}A_{Rp}C_{Rp}C_{Rp}A_{Sp}T$ | |

TABLE II

| SEQ ID NO: | Oligo # | Sequence | ISIS # |
|---|---|---|---|
| 1 | I | GCCCAAGCTG GCATCCGTCA | (ISIS-2302) |
| 2 | IV | TCCGTCATCG CTCCTCAGGG | (ISIS-2503) |
| 3 | VII | GTTCTCGCTG GTGAGTTTCA | (ISIS-3521) |
| 4 | X | TCCCGCCTGT GACATGCATT | (ISIS-5312) |
| 5 | XIII | GTGCTCATGG TGCACGGTCT | (ISIS-14803). |

Example 33

General Procedure for Oligonucleotide Purification

After the final monomer or blockmer has been added the solid support bound oligonucleotide is deprotected (trityl on) in 1–5 mL 28.0–30% ammonium hydroxide $NH_4OH$ for approximately 16 hours at 55° C. (small scale). For larger scale synthesis of oligonucleotides (20 μmol/synthesis) 20 mL of 28.0–30% ammonium hydroxide is used. In general, oligonucleotides are cleaved and deprotected in 5–20 mL 28.0–30% $NH_4OH$ at 55° C. for approximately 16 hours.

Following cleavage and deprotection the crude oligonucleotides are filtered from CPG using Gelman 0.45 μm nylon acrodisc syringe filters. Excess $NH_4OH$ is evaporated away in a Savant AS160 automatic speed vac. The crude yield is measured on a Hewlett Packard 8452A Diode Array Spectrophotometer at 260 nm. Crude samples are then analyzed by mass spectrometry (MS) on a Hewlett Packard electrospray mass spectrometer and by capillary gel electrophoresis (CGE) on a Beckmann P/ACE system 5000. Trityl-on oligonucleotides are purified by reverse phase preparative high performance liquid chromatography (HPLC). HPLC conditions are as follows: Waters 600E with 991 detector; Waters Delta Pak C4 column (7.8×300 mm); Solvent A: 50 mM triethylammonium acetate (TEA-Ac), pH 7.0; B: 100% acetonitrile; 2.5 mL/min flow rate; Gradient: 5% B for first five minutes with linear increase in B to 60% during the next 55 minutes. Larger oligo yields from the larger 20 μmol syntheses are purified on larger HPLC columns (Waters Bondapak HC18HA) and the flow rate is increased to 5.0 mL/min Appropriate fractions are collected and solvent is removed via speed vac. Oligonucleotides are detritylated in 80% acetic acid for approximately 45 minutes and lyophilized again. Free trityl and excess salt are removed by passing detritylated oligonucleotides through Sephadex G-25 (size exclusion chromatography) and collecting appropriate samples with a Pharmacia fraction collector. Concentration of selected fractions gives the purified oligonucleotides which are analyzed for purity by CGE, HPLC (flow rate: 1.5 mL/min Waters Delta Pak C4 column, 3.9×300 mm), and MS. The final yield is determined by spectrophotometer at 260 nm.

Procedure 1

Determination of Configuration of Chiral Thioates

The Rp and Sp configuration of chiral thioates are determined according to the reported procedure (Slim, G., Gait, M. J., Nucleic Acids Res., 1991 19, 1183–1188). The Rp isomer elutes in reverse phase column in HPLC as the "fast eluent. (Fraction I)" It is resistant to P1 nuclease but hydrolyzed by snake venom phosphodiesterase. On the other hand, the Sp isomer elutes in HPLC reverse phase column as the "slow" eluent (Fraction II). This stereochemistry gives protection from snake venom phosphodiesterase (SVPD), but this isomer gets hydrolyzed by PI nuclease.

Digestion by Snake Venom Phosphodiesterase

An aliquot (2 OD)of each P═S oligonucleotide dimer (both earlier and later eluting peaks by reversed-phase) HPLC is treated for 8 hours at 37° C. with snake venom phosphodiesterase (0.1 μg. Boehringer) and calf alkaline phosphatase (6.0 μg, Boehringer) in 0.1 M Tris. HCl (pH 8.5). 0.3 mM dithiothreotol (DTT), 0.3 mM $MgCl_2$ in a reaction volume of 150 μL. The products are analyzed by reverse phase HPLC. The Rp isomer (the earlier eluting peak) is hydrolyzed while the Sp isomer remains intact.

Digestion by Nuclease P1

An aliquot of each P═S oligonucleotide dimer (2 ODs) is digested with nuclease P1 (2.0 μg, Boehringer) in distilled water (120 μL) for 1 hour at 37° C. The solution is buffered with 16 μL. 0.1 M Tris HCl (pH 8.5) and digested with calf alkaline phosphatase (6.0 μg, Boehringer) for 1 hour at 37° C. The product is analyzed by reverse phase HPLC. In this case, the Sp isomer is degraded while the Rp isomer is resistant to nuclease.

Procedure 2

Evaluation of In Vivo Stability of Chimeric Chiral Oligonucleotides

Mouse Experiment Procedures

For each oligonucleotide tested 9 male BALE/c mice (Charles River, Wilmington, Mass.), weighing about 25 g are used (Crooke et al., J. Pharmacol. Exp. Ther, 1996, 277, 923). Following a 1-week acclimation, mice receive a single tail vein injection of oligonucleotide (5 mg/kg) administered in phosphate buffered saline (PBS), pH 7.0 One retro-orbital bleed (either 0.25. 0.5, 2 or 4 lv post dose) and a terminal bleed (either 1, 3, 8 or 24 h post dose) are collected from each group. The terminal bleed (approximately 0.6–0.8 ml) is collected by cardiac: puncture following ketamine/xylazine anesthesia. The blood is transferred to an EDTA-coated collection tube and centrifuged to obtain plasma. At termination, the liver and kidneys are collected from each mouse. Plasma and tissues homogenates are used for analysis for determination of intact oligonucleotide content by CGE. All samples are immediately frozen on dry ice after collection and stored at −80° C. until analysis.

Evaluation of In Vivo Stability of Chimeric Chiral Oligonucleotides

SEQ ID NO: 5 was used in a comparative study to determine the effect of chiral internucleotide linkages at predetermined positions compared to the same sequence having racemic linkages at each position. The capillary gel electrophoretic analysis indicated the relative nuclease resistance of Chiral 3'-Sp-capped oligomers compared to ISIS 3082 (XVI, uniform 2'-deoxy phosphorothioate). Because of the resistance of Sp linkage to nucleases, Compounds XVII and XVIII are found to be stable in plasma, kidney and liver while XVI (3082) is not. On the other hand, the data from 5',-3'-bis Sp capped oligomers show total exonucleolytic stability in plasma as well as in tissues (liver and kidney). Compounds are stable at various time points such as 1. 3, and 24 hours. The fact that no degradation is detected proved that 5'-exonucleases and 3'-exonuclease are prevalent in tissues and endonucleases are not active. Furthermore, a single Chiral linkage (Sp thioate linkage) is sufficient as a gatekeeper against nucleases at the termini.

Procedure 3

RNase H Studies With Chimeric Rp and Sp Modified Oligonucleotides $^{32}$P Labeling of Oligonucleotides The oligoribonucleotide (sense strand) is Y-end labeled with $^{32}$P using [$^{32}$P]ATP, T4 polynucleotide kinase, and standard procedures (Ausubel et al., Current Protocols in Molecular Biology, John Wiley, New York (1989)). The labeled RNA is purified by electrophoresis on 12% denaturing PAGE (Sambrook et al., Molecular Cloning: A Laboratory Manual, Cold Spring Harbor Laboratory Press. Plainview (1989)). The specific activity of the labeled oligonucleotide is approximately 6000 cpm/fmol.

Determination of RNase H Cleavage Patterns

Hybridization reactions were prepared in 120 μL of reaction buffer [20 mM Tris-HCl (pH 7.5), 20 mM KCl. 10 mM $MgCl_2$, 0.1 mM DTT] containing 750 nM antisense oligonucleotide, 500 nM sense oligoribonucleotide, and 100,000 cpm $^{32}$P-labeled sense oligoribonucleotide. Reactions were heated at 90° C. for 5 minutes and 1 unit of Inhibit-ACE is added. Samples were incubated overnight at 37° C. degrees. Hybridization reactions were incubated at 37° C. with $1.5\times10.8^{-8}$ mg of E. coli RNase H enzyme for initial rate determinations and then quenched at specific time points. Samples were analyzed by trichloroacetic acid (TCA) assay or by denaturing polyacrylamide gel electrophoresis as previously described [Crooke, S. T, Lemonidis, K. M., Neilson, L., Griffey, R., Lesnik. E. A., and Moria, B. P., Kinetic characteristics of Escherichia coli RNase H1; cleavage of various antisense oligonucleotide-RNA duplexes. Biochem J, 312, 599 (1995); Lima. W. F, and Crooke. S. T., Biochemistry 36, 390–398, 1997]. In these assays chirally pure Compounds of the type Sp-(Rp)n-Sp showed better Rnase H cleavage activity than diasteromeric mixture Compounds.

Hybridization reactions were prepared in 120 μL, of reaction buffer [20 mM Tris-HC (pH 7.5), 20 mM KCl, 10 mM $MgCl_2$, 0.1 mM DTT] containing 750 nM antisense oligonucleotide, 500 nM sense oligoribonucleotide, and 100,000 cpm 32P-labeled sense oligoribonucleotide. Reactions were heated at 90° C. for 5 min and 1 unit of Inhibit-ACE is added. Samples were incubated overnight at 37° C. degrees. Hybridization reactions were incubated at 37° C. with $1.5\times10.8^{-8}$ mg of E. coli RNase H enzyme for initial rate determinations and then quenched at specific time points. Samples were analyzed by trichloroacetic acid (TCA) assay or by denaturing polyacrylamide gel electrophoresis as previously described (Crooke et al., Biochem J., 1995, 312, 599; Lima, W. F, and Crooke, S. T., Biochemistry, 1997, 36, 390–398).

Procedure 4

Control of H-ras Gene Expression With Chirally Defined Phosphorothioate Oligomers H-ras targeted antisense oligonucleotides were tested for the ability to specifically reduce H-ras mRNA in T-24 cells (ATCC. Manassas, Va.). T-24 cells were routinely maintained in complete growth media. DMEM supplemented with 10% fetal calf serum and 100 units per milliliter penicillin and 100 micrograms per milliliter streptomycin (Lifetechnologies, Grand Island, N.Y.) in a humidified incubator at 37° C. For antisense experiments T-24 cells were plated in 6-well plates (Becton Dickinson Labware, Franklin Lakes, NJ.) at a density of $2\times10^5$ cells per well in complete growth medium and incubated as above. Twenty-four hours after plating the growth media is aspirated and the monolayer is washed once with serum free media (Optimem. Lifetechnologies, Grand Island. N.Y.). Oligonucleotides were formulated in serum free Optimem and Lipofectin (Lifetechnologies, Grand Island, N.Y) at a constant ratio of 3 micrograms per milliliter Lipofectin per 100 nanomolar oligonucleotide. For oligonucleotide treatment two milliliters of formulated oligonucleotide is added to each well and the cells were incubated for four hours at 37° C. Following incubation the formulated oligonucleotide is aspirated from the monolayer, replaced with growth media, and incubated overnight. Twenty-four hours after treatment total RNA is prepared using RNAzol (TEL-TEST, Inc., Friendswood, Tex.) following manufactures protocol. RNA is fractionated through 1.2% agarose-formaldehyde gels and transferred to nylon membranes (Amersham Pharmacia Biotech, Piscataway, N.J.) following standard protocols (Sambrook et al. Molecular Cloning a Laboratory Manual, 2nd edition. Cold Spring Harbor Laboratory Press, Cold Spring Harbor, N.Y. 1989). Nylon membranes were probed for H-ras (Oncogene Research Products, Cambridge, Mass.) using standard 32P random priming labeling and hybridization protocols (Sambrook et al. Molecular Cloning a Laboratory Manual, $_2$nd edition, Cold Spring Harbor Laboratory Press, Cold Spring Harbor, N.Y. 1989). Following hybridization membranes were imaged using a PhosphorImager (Molecular Dynamics, Sunnyvale, Calif.) and the images quantified using Image Quant 5.0 software (Molecular Dynamics, Sunnyvale, Calif.). Following image analysis membranes were striped of H-ras probe and reprobed for G3PDH (Clonetech, Palo Alto, Calif.) and analyzed as above. H-ras signal is normalized to G3PDH. The mean normalized percent control of triplicates and standard deviation for H-ras signal is calculated. Using this procedure Compounds IV, V and VI are tested. Compounds V and VI show faster efficient reduction of H-ras messages.

Procedure 5

Determination of ICAM-1 Expression

Oligonucleotide Treatment of HUVECs

Cells were washed three times with Opti-MEM (Lift Technologies, Inc.) prewarmed to 37° C. Oligonucleotide were premixed with 10 g/mL Lipofectin (Life Technologies Inc.) in Opti-MEM, serially diluted to the desired concentrations, and applied to washed cells. Basal and untreated (no oligonucleotide) control cells were also treated with Lipofectin. Cells were incubated for 4 hours at 37° C., at which time the medium is removed and replaced with standard growth medium with or without 5 mg/mL TNF-α (R & D Systems). Incubation at 37° C. is continued until the indicated times.

Quantitation of ICAM-1 Protein Expression by Fluorescence-activated Cell Sorter

Cells were removed from plate surfaces by brief trypsinization with 0.25% trypsin in PBS. Trypsin activity is quenched with a solution of 2% bovine serum albumin and 0.2% sodium azide in PBS (+Mg/Ca). Cells were pelleted by centrifugation (1000 rpm. Beckman GPR centrifuge), resuspended in PBS. and stained with 3 1/$10^5$ cells of the ICAM-1 specific antibody. CD54-PE (Pharmingin). Antibodies were incubated with the cells for 30 min at 4C in the dark, under gently agitation. Cells were washed by centrifugation procedures and then resuspended in 0.3 ml of FacsFlow buffer (Becton Dickinson) with 0.5% formaldehyde (Polysciences). Expression of cell surface ICAM-1 is then determined by flow cytometry using a Becton Dickinson FACScan. Percentage of the control ICAM-1 expression is calculated as follows: [(oligonucleotide-treated ICAM-1 value)—(basal ICAM-1 value)/(non-treated ICAM-1 value)—(basal ICAM-1 value)]. (Baker et al., The Journal of Biological Chemistry, 1997, 272, 11994–12000).

When ICAM-1 expression is tested with oligomers I. II and III, it is observed that the ICAM-1 expression data reveal that the oligomers II and III are more efficacious than oligomer I in HUVEC cells. The oligomers are presumably working by a improved nuclease resistance in case of oligomer II and enhanced RNaseH activity and improved nuclease resistance in the case of oligomer III.

Procedure 6

5-Lipoxygenase Analysis and Assays

A. Therapeutics For therapeutic use, an animal suspected of having a disease characterized by excessive or abnormal supply of 5-lipoxygenase is treated by administering the macromolecule of the invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents The oligonucleotides of this invention will also be useful as research reagents when used to cleave or otherwise modulate 5-lipoxygenase mRNA in crude cell lysates or in partially purified or wholly purified RNA preparations. This application of the invention is accomplished for example, by lysing cells by standard methods, optimally extracting the RNA and then treating it with a composition at concentrations ranging, for instance, from about 100 to about 500 ng per 10 Mg of total RNA in a buffer consisting, for example, of 50 mm phosphate, pH ranging from about 4–10 at a temperature from about 30° to about 50° C. The cleaved 5-lipoxygenase RNA can be analyzed by agarose gel electrophoresis and hybridization with radiolabeled DNA probes or by other standard methods.

C. Diagnostics The oligonucleotides of the invention will also be useful in diagnostic applications, particularly for the determination of the expression of specific mRNA species in various tissues or the expression of abnormal or mutant RNA species. In this example, while the macromolecules target a abnormal mRNA by being designed complementary to the abnormal sequence, they would not hybridize to normal mRNA.

Tissue samples can be homogenized, and RNA extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the mRNA would bind to the solid support. The 3' region of the abnormal RNA, which is cleaved, would not be bound to the support and therefore would be separated from the normal mRNA.

Targeted mRNA species for modulation relates to 5-lipoxygenase: however, persons of ordinary skill in the art will appreciate that the present invention is not so limited and it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays The cellular assays for 5-lipoxygenase preferably use the human promyelocytic leukemia cell line HL-60. These cells can be induced to differentiate into either a monocyte like cell or neutrophil like cell by various known agents. Treatment of the cells with 1.3% dimethyl sulfoxide, DMSO, is known to promote differentiation of the cells into neutrophils. It has now been found that basal HL-60 cells do not synthesize detectable levels of 5–6-lipoxygenase protein or secrete leukotrienes (a downstream product of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of oligonucleotides which interfere with 5-lipoxygenase synthesis in these cells.

A second test system for oligonucleotides makes use of the fact that 5-lipoxygenase is a "suicide" enzyme in that it inactivates itself upon reacting with substrate. Treatment of differentiated HL-60 or other cells expressing 5 lipoxygenase, with 10 μM A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene $B_4$. Macromolecules directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells.

A direct effect which oligonucleotides can exert on intact cells and which can be easily be quantitated is specific inhibition of 5-lipoxygenase protein synthesis. To perform this technique, cells can be labeled with $^{35}$S-methionine (50 μCi/mL) for 2 hours at 37° C. to label newly synthesizes protein. Cells are extracted to solubilize total cellular proteins and 5-lipoxygenase is immunoprecipitated with 5-lipoxygenase antibody .followed by elution from protein A Sepharose beads. The immunoprecipitated proteins an resolved by SDS-polyacrylamide gel electrophoresis and exposed for autoradiography. The amount of immunoprecipitated 5-lipoxygenase is quantitated by scanning densitometry.

A predicted result from these experiments would be a follows. The amount of 5-lipoxygenase protein immunoprecipitated from control cells would be normalized to 100% Treatment of the cells with 1 μM, 10 μM, and 30 μM of the macromolecules of the invention for 48 hours would reduce immunoprecipitated 5-lipoxygenase by 5%, 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10.000×g for 30 min and the supernatants analyzed for 5-lipoxygenase activity. Cytosolic proteins are incubated with 10 μM $^{14}$C-arachidonic acid, 2 mM ATP 50 μM free calcium, 100 μg/mL phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL-60 cells for 72 hours with effective the macromolecules of the invention at 1 μM, 10 μM, and 30 μM, would be as follows. Control cells oxidize 200 pmol arachidonic acid/5 min/$10^6$ cells. Cells treated with 1 μM, 10 μM, and 30 μM of an effective oligonucleotide would oxidize 195 pmol, 140 pmol, and 60 pmol of arachidonic acid/5 min/$10^6$ cells respectively.

A quantitative competitive enzyme linked immunosorbant assay (ELISA) for the measurement of total 5-lipoxygenase protein in cells has been developed. Human 5-lipoxygenase expressed in E. coli and purified by extraction. Q-Sepharose, hydroxyapatite, and reverse phase HPLC is used as a standard and as the primary antigen to coat microtiter plates. 25 ng of purified 5-lipoxygenase is bound to the microtiter plates overnight at 4° C. The wells are blocked for 90 min with 5% goat serum diluted in 20 mM Tris.HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 μL in the microtiter wells for 90 min. The antibodies are prepared by immunizing rabbits with purified human recombinant 5-lipoxygenase. The wells are washed with TBS containing 0.05% tween 20 (TBST), then incubated with 100 μL, of a 1:1000 dilution of peroxidase conjugated goat anti-rabbit IgG (Cappel Laboratories, Malvern, Pa.) for 60 min at 25° C. The wells are washed with TBST and the amount of peroxidase labeled second antibody determined by development with tetramethylbenzidine.

Predicted results from such an assay using a 30 mer oligonucleotide at 1 μM, 10 μM, and 30 μM, would be 30 ng, 18 ng and 5 ng of 5-lipoxygenase per $10^6$ cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore A23187. Leukotriene B4 released into the cell medium can be quantitated by radioimmunoassay using commercially available diagnostic kits (New England Nuclear, Boston, Mass.). Leukotriene B4 production can be detected in HL-60 cells 48 hours following addition of DMSO to differentiate the cells into a neutrophil-like cell. Cells ($2\times10^5$ cells/mL) will he treated with increasing concentrations of the macromolecule for 48–72 hours in the presence of 1.3% DMSO. The cells are washed and resuspended at a concentration of $2\times10^6$ cell/mL in Dulbecco's phosphate buffered saline containing 1% delipidated bovine serum albumin. Cells are stimulated with 10 μM, calcium ionophore A23187 for 15 min and the quantity of $LTB_4$ produced from $5\times10^5$ cell determined by radioimmunoassay as described by the manufacturer.

Using this assay the following results would likely be obtained with an oligonucleotide directed to the 5-LO mRNA. Cells will be treated for 72 hours with either 1 μM. 10 μM, or 30 μM, of the macromolecule in the presence of 1.3% DMSO. The quantity of $LTB_4$ produced from $5\times10^5$ cells would be expected to be about 75 μg, 50 μg, and 35 μg, respectively with untreated differentiated cells producing 75 pg $LTB_4$.

E. In Vivo Assay Inhibition of the production of 5-lipoxygenase in the mouse can be demonstrated in accordance with the following protocol. Topical application of arachidonic acid results in the rapid production of leukotriene $B_4$, leukotriene $C_4$ and prostaglandin $E_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene $B_4$ produced in biopsy specimens is performed as a direct measurement of 5-lipoxygenase activity in the tissue. Oligonucleotides will be applied topically to both ears 12 to 24 hours prior to administration of arachidonic acid to allow optimal activity of the compounds. Both ears are pretreated for 24 hours with either 0.1 μmol, 0.3 μmol, or 1.0 μmol of the macromolecule prior to challenge with arachidonic acid. Values are expressed as the mean for three animals per concentration. Inhibition of polymorphonuclear cell infiltration for 0.1 μmol. 0.3 μmol, and 1 μmol is expected to be about 10%, 75% and 92% of control activity, respectively. Inhibition of edema is expected to be about 3%, 58% and 90%, respectively while inhibition of leukotriene $B_4$ production would be expected to be about 15%, 79% and 99%, respectively.

It is intended that each of the patents, applications, printed publications, and other published documents mentioned or referred to in this specification be herein incorporated by reference in their entirety.

Those skilled in the art will appreciate that numerous changes and modifications can be made to the preferred embodiments of the invention and that such changes and modifications can be made without departing from the spirit of the invention. It is therefore intended that the appended claims cover all such equivalent variations as fall within the true spirit and scope of the invention.

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 1

gcccaagctg gcatccgtca                                                20


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 2

tccgtcatcg ctcctcaggg                                                20


<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 3

gttctcgctg gtgagtttca                                                20


<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 4

tcccgcctgt gacatgcatt                                                20
```

-continued

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 5

gtgctcatgg tgcacggtct                                                20


<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: antisense
      sequence

<400> SEQUENCE: 6

tgcatccccc aggccaccat                                                20
```

What is claimed is:

1. An oligomeric compound comprising a plurality of covalently-bound nucleosides; said compound having the formula:

$$5'\text{-}T_1\text{—}(Nu\text{—}Sp)_n\text{—}(Nu\text{—}Lp)_m\text{—}(NU\text{—}Sp)_p\text{—}Nu\text{—}T_2\text{-}3'$$

wherein:

$T_1$ and $T_2$ are each, independently, hydroxyl, a protected hydroxyl, a covalent attachment to a solid support, a nucleoside, an oligonucleoside, a nucleotide, an oligonucleotide, a conjugate group or a 5' or 3' substituent group;

each Sp is a chiral Sp phosphorothioate internucleoside linkage;

each Lp is, independently, a chiral Rp phosphorothioate internucleoside linkage, a racemic phosphorothioate internucleoside linkage or an internucleoside linkage other than a chiral phosphorothioate internucleoside linkage;

each n and m is, independently, from 1 to 100;

each p is from 0 to 100; where the sum of n, m and p is from 3 to about 200;

each Nu independently, has the formula:

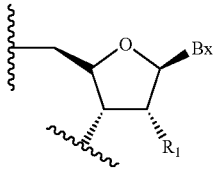

wherein:

Bx is a heterocyclic base moiety; and $R_1$ is H, hydroxyl, a protected hydroxyl, a 2'-substituent group or a protected 2'-substituent group.

2. The oligomeric compound of claim 1 wherein each R, is H or hydroxyl.

3. The oligomeric compound of claim 1 wherein $R_1$ is $C_1$–$C_{10}$ O-alkyl or $C_1$–$C_{10}$ substituted O-alkyl.

4. The oligomeric compound of claim 3 wherein $R_1$ is 2'-O-methoxyethyl or 2'-O-methyl.

5. The oligomeric compound of claim 1 wherein each Nu is, independently, adenosine, guanosine, uridine, 5-methyluridine, cytidine, 5-methylcytidine or thymine.

6. The oligomeric compound of claim 1 wherein the sum of n, m, and p is from 5 to about 50.

7. The oligomeric compound of claim 1 wherein the sum of n, m, and p is from 8 to about 30.

8. The oligomeric compound of claim 1 wherein the sum of n, m, and p is from 10 to about 25.

9. The oligomeric compound of claim 1 wherein p is 1 or 2.

10. The oligomeric compound of claim 1 wherein n and p are each 1 and m is from 3 to about 20.

11. The oligomeric compound of claim 1 wherein $T_1$ and $T_2$ are, independently, hydroxyl or a protected hydroxyl.

12. The oligomeric compound of claim 1 wherein each Lp is an Rp phosphorothioate internucleoside linkage.

13. The oligomeric Compound of claim 1 wherein at least one Lp is a racemic phosphorothioate internucleoside linkage.

14. The oligomeric Compound of claim 1 wherein at least one Lp is an internucleoside linkage other than a chiral phosphorothioate internucleoside linkage.

15. The oligomeric Compound of claim 1 wherein $R_1$ is a 2'-substituent group or a protected 2'-substituent group.

16. A pharmaceutical composition comprising a compound of claim 1 and an acceptable pharmaceutical carrier.

17. A nucleoside having the formula:

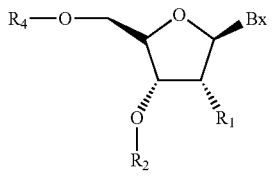

wherein:

Bx is a heterocyclic base moiety;

$R_4$ is a hydroxyl protecting group;

$R_1$ is H, hydroxyl, a protected hydroxyl, a 2'-substituent group or a protected 2'-substituent group; and $R_2$ is an Sp chiral auxiliary group.

18. The nucleoside of claim 17 wherein said chiral auxiliary group has one of formulas I, II, III, IV, V or VI:

I

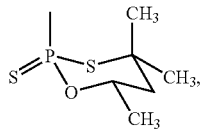

II

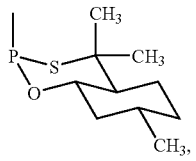

III

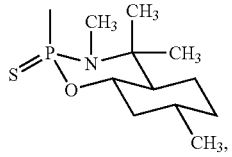

IV

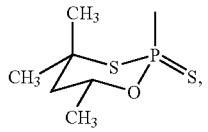

V

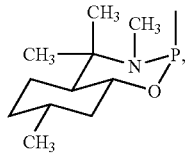

VI

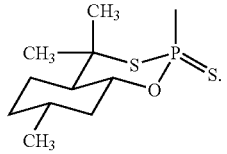

19. The nucleoside of claim 17 wherein Bx is adenosine, guanosine, uridine, 5-methyluridine, cytidine, 5-methylcytidine or thymine.

20. The nucleoside of claim 17 wherein each $R_1$ is H or hydroxyl.

21. The nucleoside of claim 17 wherein $R_1$ is $C_1$–$C_{10}$ alkyl or $C_1$–$C_{10}$ substituted alkyl.

22. The nucleoside of claim 21 wherein $R_1$ is 2'-O-methoxyethyl or 2'-O-methyl.

23. The nucleoside of claim 17 wherein at least one $R_1$ is 2'-O-methoxyethyl or 2'-O-methyl.

24. The nucleoside of claim 17 wherein $R_1$ is a 2'-substituent group or a protected 2'-substituent group.

25. A method of preparing an oligomeric compound of formula:

$$5'\text{-}T_1\text{—}(Nu\text{—}Sp)_n\text{—}(NU\text{—}Lp)_m\text{—}(NU\text{—}Sp)_p\text{—}Nu\text{—}T_2\text{-}3'$$

wherein:

each $T_1$ and $T_2$ is, independently, hydroxyl, a protected hydroxyl, a covalent attachment to a solid support, a nucleoside, an oligonucleotide, a nucleotide or an oligonucleotide, a conjugate group or a 5' or 3' substituent group;

each Sp is an Sp phosphorothioate internucleoside linkage;

each Lp is, independently, an Rp phosphorothioate internucleoside linkage, a racemic phosphorothioate internucleoside linkage or an internucleoside linkage other than a chiral Rp phosphorothioate internucleoside linkage;

each n and m is, independently, from 1 to 100;

each p is from 0 to 100 where the sum of n, m and p is from 3 to about 200:

each Nu, independently, has the formula:

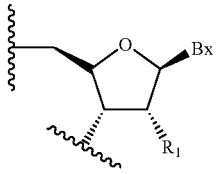

wherein

Bx is a heterocyclic base moiety; and $R_1$ is H, hydroxy, a protected hydroxyl, a 2'-substituent group or a protected 2'-substituent group;

comprising the steps of:

(a) providing a compound of formula:

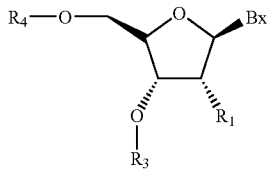

wherein:

$R_4$ is a labile hydroxyl protecting group;

$R_3$ is a covalent attachment to a solid support;

(b) deblocking said labile hydroxyl protecting group to form a deblocked hydroxyl group;

(c) optionally treating said deblocked hydroxyl group with a further compound having the formula:

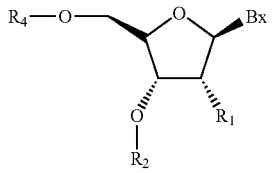

wherein:

$R_2$ is an Sp chiral auxiliary group;

and a condensing reagent to form an extended compound:

(d) optionally repeating steps (b) and (c);

(e) treating said deblocked hydroxyl group with a compound having the formula:

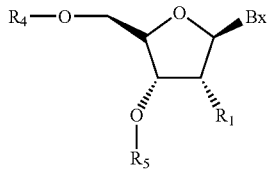

wherein:

$R_5$ is an Rp chiral auxiliary group or an activated phosphorus group;

and a condensing reagent to form a further extended compound;

(f) optionally repeating steps (e) and (f) to add further nucleosides;

(g) deblocking said labile hydroxyl protecting group to form a deblocked hydroxyl group;

(h) treating said deblocked hydroxyl group with a further compound having the formula:

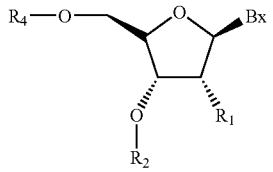

wherein:

$R_1$ is an Sp chiral auxiliary group;

and a condensing reagent to form a protected oligomeric compound; and (i) optionally repeating steps (h) and (i) to add at additional nucleosides thereby forming a further protected oligomeric compound.

26. The method of claim 25 further comprising the step of deblocking the product of step (i).

27. The method of claim 25 wherein said Sp chiral auxiliary group has one of formulas I, II or III:

I

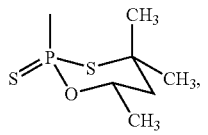

II

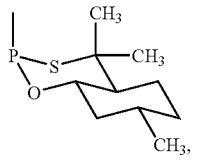

III

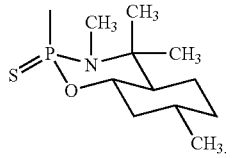

28. The method of claim 25 wherein said Rp chiral auxiliary group has one of formulas IV, V or VI:

IV

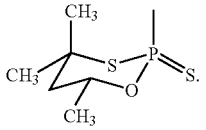

V

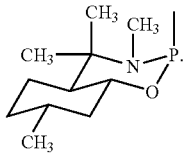

VI

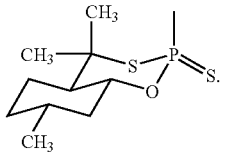

29. The method of claim 25 further comprising one or more capping steps after steps c, d, e, f, h, or i; said capping steps comprising treatment with a capping agent.

30. The method of claim 25 further comprising one or more oxidation steps; said oxidation steps comprising treatment with an oxidizing agent.

31. The method of claim 25 wherein said labile hydroxyl protecting group is dimethoxytrityl, monomethoxy trityl, trityl or 9-phenyl-xanthene.

32. The method of claim 25 wherein said heterocyclic base moiety is a purine or a pyrimidine.

33. The method of claim 32 wherein said purine or pyrimidine is, independently, adenosine, guanosine, uridine, 5-methyluridine, cytidine, 5-methylcytidine or thymine.

34. The method of claim 25 wherein the sum of n, m, and p is from 5 to about 50.

35. The method of claim 25 wherein the sum of n, m, and p is from 8 to about 30.

36. The method of claim 25 wherein the sum of n, m, and p is from 10 to about 25.

37. The method of claim 25 wherein $T_1$ and $T_2$ are, independently hydroxyl or a protected hydroxyl.

38. The method of claim 25 wherein each Lp is an Rp phosphorothioate internucleoside linkage.

39. The method of claim 25 wherein at least one Lp is a racemic phosphorothioate internucleoside linkage.

40. The method of claim 25 wherein n and p are each 1 and m is from 3 to about 20.

41. The method of claim 25 wherein n and p are each 2 and m is from 3 to about 20.

42. The method of claim 25 wherein p is 0.

43. The method of claim 25 wherein at least one $R_1$ is a 2'-substituent group or a protected 2'-substituent group.

44. The method of claim 25 wherein said activated phosphorus group is a phosphoramidite, an H-phosphonate or a phosphate triester.

45. The method of claim 25 wherein said covalent attachment to a solid support is a sarcosinyl-succinonyl linker.

46. A method of modulating the production or activity of a protein in an organism, comprising contacting said organism with a compound of claim 1, wherein said protein is protein kinase C, ICAM-1, VCAM-1, PECAM-1, ELAM-1, H-ras, K-ras, AP-1, a Jun N-terminal kinase, or a matrix metalloproteinase.

47. A method of treating an organism having a disease characterized by the undesired production of a protein, comprising contacting said organism with a compound of claim 1, wherein said disease is psoriasis, an inflammatory disorder of the skin, an infectious disease of the skin, or skin cancer.

48. The oligomeric compound of claim 47 wherein $R_1$ is 2'-O-methoxyethyl or 2'-O-methyl.

49. A compound of formula:

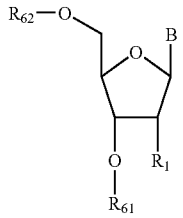

wherein:

$R_{62}$ is H or a hydroxyl protecting group;

$R_1$ is H, hydroxyl, a protected hydroxyl, a 2'-substituent group or a protected 2'-substituent group;

B is a heterocyclic base moiety; and $R_{61}$ is a chiral auxiliary selected from formulas I–VI:

I

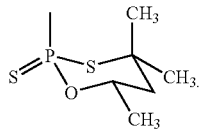

II

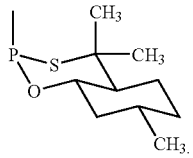

III

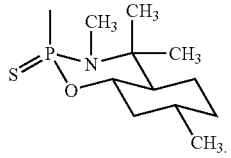

IV

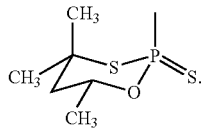

V

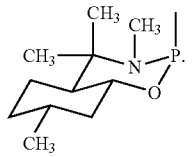

VI

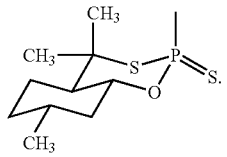

50. The oligomeric compound of claim 49 wherein each $R_1$ is H or hydroxyl.

51. The oligomeric compound of claim 49 wherein $R_1$ is $C_1$–$C_{10}$ O-alkyl or $C_1$–$C_{10}$ substituted O-alkyl.

52. The oligomeric compound of claim 51 wherein $R_1$ is 2'-O-methoxyethyl or 2'-O-methyl.

53. The oligomeric compound of claim 49 wherein each Nu is, independently, adenosine, guanosine, uridine, 5-methyluridine, cytidine, 5-methylcytidine or thymine.

[54. A compound having the formula:

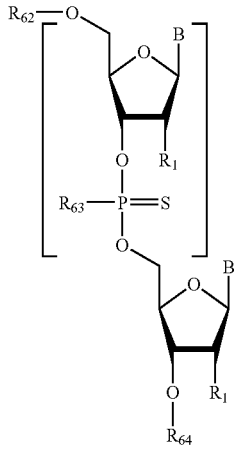

wherein:

B is a heterocyclic base moiety;

q is 0 to about 50;

$R_{62}$ is H or a hydroxyl protecting group;

$R_1$ is H, hydroxyl, a protected hydroxyl, a 2'-substituent group or a protected) 2'-substituent group;

$R_{64}$ is H, a hydroxyl protecting group, or a linker to a solid support;

$R_{63}$ is a radical selected from the group consisting of

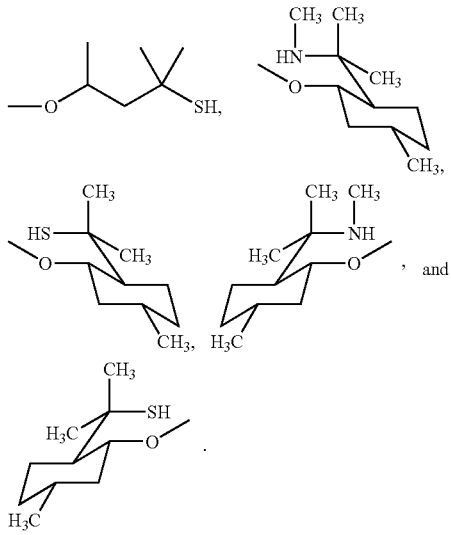

]

55. The [oligomeric] compound of claim 54 wherein each $R_1$ is H or hydroxyl.

56. The [oligomeric] compound of claim 54 wherein $R_1$ is $C_1$–$C_{10}$ O-alkyl or $C_1$–$C_{10}$ substituted O-alkyl.

57. The [oligomeric] compound of claim 54 wherein $R_1$ is 2'-O-methoxyethyl or 2'-O-methyl.

58. The [oligomeric] compound of claim 54 wherein each Nu is, independently, adenosine, guanosine, uridine. 5-methyluridine, cytidine 5-methylcytidine or thymine.

59. The [oligomeric] compound of claim 54 wherein q is 5 to about 50.

60. The [oligomeric] compound of claim 54 wherein q is from 8 to about 30.

61. The [oligomeric] compound of claim 54 wherein q is from 10 to about 25.

62. The [oligomeric] compound of claim 54 wherein q is 1.

[63. The oligomeric compound of claim 54 wherein q is 0.]

*64. A compound having the formula:*

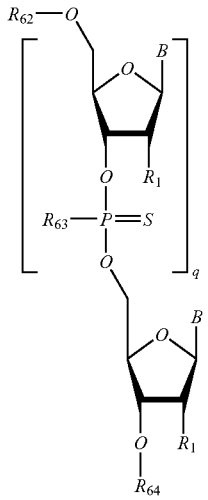

*wherein:*

*B is a heterocyclic base moiety;*

*q is 1 to about 50;*

*$R_{62}$ is H or a hydroxyl protecting group;*

*$R_1$ is H, hydroxyl, a protected hydroxyl, a 2'-substituent group or a protected 2'-substituent group;*

*$R_{64}$ is H, a hydroxyl protecting group, or a linker to a solid support;*

*$R_{63}$ is a radical selected from the group consisting of*

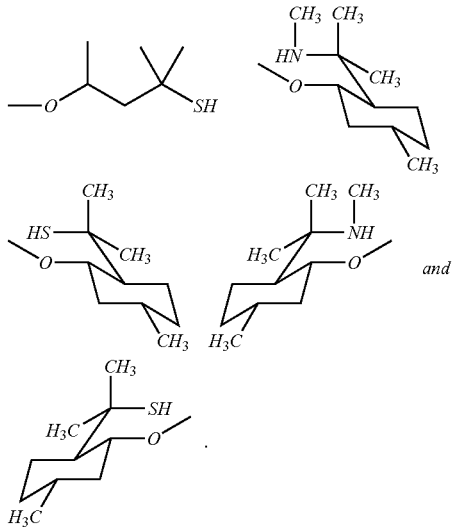

* * * * *

UNITED STATES PATENT AND TRADEMARK OFFICE

CERTIFICATE OF CORRECTION

PATENT NO. : RE 39,464 E 
APPLICATION NO. : 10/925348
DATED : January 9, 2007
INVENTOR(S) : Phillip Dan Cook and Muthiah Manoharan It is certified that error appears in the above-identified patent and that said Letters Patent is hereby corrected as shown below:

On the title page item (54), and col. 1, line 1, delete "OLIGONUCLEOLOTIDES" and insert therefor --OLIGONUCLEOTIDES--;

Title page Item [56], References Cited, OTHER PUBLICATIONS, line 4, "Berkow" reference, delete "," after "Merck";

Title page item (56), line 14, "Boggemeyer" reference, delete "E-selecin. P-Selectin." and insert therefor --E-selectin, P-selectin,--;

Title page item (56), line 27, "Dean" reference, delete "C-αexpression" and insert therefor --C-α expression--;

Title page item (56), line 28, "Dean" reference, delete "posphorthioate" and insert therefor --phosphorthioate--;

Title page item (56), line 28, "Dean" reference, delete "oligodeoxynucledotides" and insert therefor --oligodeoxynucleotides--;

Column 53, Claim 1, line 32, delete "5'$T_1$-(Nu-Sp)$_n$-(Nu-Lp)$_m$-(NU-Sp)$_p$-Nu-$T_2$-3'" and insert therefor --5'$T_1$-(Nu-Sp)$_n$-(Nu-Lp)$_m$-(Nu-Sp)$_p$-Nu-$T_2$-3'--;

Column 53, Claim 2, line 64, delete "R," and insert therefor --$R_1$--;

Column 55, Claim 25, line 67, delete "5'$T_1$-(Nu-Sp)$_n$-(NU-Lp)$_m$-(NU-Sp)$_p$-Nu-$T_2$-3'" and insert therefor --5'$T_1$-(Nu-Sp)$_n$-(Nu-Lp)$_m$-(Nu-Sp)$_p$-Nu-$T_2$-3'--;

Column 56, Claim 25, line 64, delete ":" and insert therefor --;--;

Column 57, Claim 25, line 34, delete "$R_1$" and insert therefor --$R_2$--;

Column 59, Claim 49, delete "

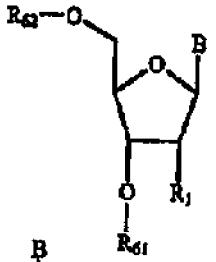

"

and insert therefor --

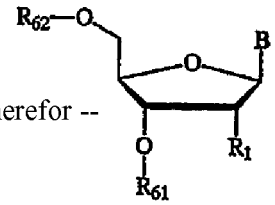

--;

UNITED STATES PATENT AND TRADEMARK OFFICE

CERTIFICATE OF CORRECTION

PATENT NO. : RE 39,464 E
APPLICATION NO. : 10/925348
DATED : January 9, 2007
INVENTOR(S) : Phillip Dan Cook and Muthiah Manoharan It is certified that error appears in the above-identified patent and that said Letters Patent is hereby corrected as shown below:

Column 60, Claim 55, line 62, delete "54" and insert therefor --[54] 64--;

Column 60, Claim 56, line 64, delete "54" and insert therefor --[54] 64--;

Column 60, Claim 57, line 66, delete "54" and insert therefor --[54] 64--;

Column 61, Claim 58, line 1, delete "54" and insert therefor --[54] 64--;

Column 61, Claim 59, line 4, delete "54" and insert therefor --[54] 64--;

Column 61, Claim 60, line 6, delete "54" and insert therefor --[54] 64--;

Column 61, Claim 61, line 8, delete "54" and insert therefor --[54] 64--;

Column 61, Claim 62, line 10, delete "54" and insert therefor --[54] 64--.

Signed and Sealed this

Sixth Day of March, 2007

JON W. DUDAS
*Director of the United States Patent and Trademark Office*